(12) United States Patent
Murata et al.

(10) Patent No.: US 9,725,474 B2
(45) Date of Patent: Aug. 8, 2017

(54) MODIFIED NUCLEIC ACID

(71) Applicant: TAKEDA PHARMACEUTICAL COMPANY LIMITED, Osaka-shi, Osaka (JP)

(72) Inventors: Shumpei Murata, Fujisawa (JP); Shinichi Masada, Fujisawa (JP); Naoki Miyamoto, Fujisawa (JP); Tadashi Umemoto, Fujisawa (JP)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

(21) Appl. No.: 14/439,460

(22) PCT Filed: Oct. 30, 2013

(86) PCT No.: PCT/JP2013/079389
§ 371 (c)(1),
(2) Date: Apr. 29, 2015

(87) PCT Pub. No.: WO2014/069520
PCT Pub. Date: May 8, 2014

(65) Prior Publication Data
US 2016/0016983 A1    Jan. 21, 2016

(30) Foreign Application Priority Data
Oct. 31, 2012 (JP) .................................. 2012-241286

(51) Int. Cl.
| | | |
|---|---|---|
| C07F 9/6561 | (2006.01) | |
| C07H 21/02 | (2006.01) | |
| C07F 9/6558 | (2006.01) | |
| C07H 21/00 | (2006.01) | |
| C07D 239/54 | (2006.01) | |
| C07D 473/34 | (2006.01) | |
| C07F 9/6512 | (2006.01) | |

(52) U.S. Cl.
CPC ........ *C07F 9/65616* (2013.01); *C07D 239/54* (2013.01); *C07D 473/34* (2013.01); *C07F 9/65121* (2013.01); *C07F 9/65583* (2013.01); *C07F 9/65586* (2013.01); *C07H 21/00* (2013.01); *C07H 21/02* (2013.01)

(58) Field of Classification Search
CPC .................................................. C07D 400/12
See application file for complete search history.

(56) References Cited

U.S. PATENT DOCUMENTS

| | | |
|---|---|---|
| 5,681,940 A | 10/1997 | Wang et al. |
| 5,712,378 A | 1/1998 | Wang |
| 6,191,266 B1 | 2/2001 | Wang |
| 6,743,902 B1 | 6/2004 | Wang |

FOREIGN PATENT DOCUMENTS

| | | |
|---|---|---|
| JP | 10-506915 | 7/1998 |
| JP | 2007-197376 | 8/2007 |
| WO | WO 2011/139710 A1 | 11/2011 |

OTHER PUBLICATIONS

A. Pasternak et al., "Unlocked nucleic acid—an RNA modification with broad potential", Organic & Biomolecular Chemistry, vol. 9, pp. 3591-3597 (2011).
Y. Kuroiwa et al., "Chemoselective Reduction of Aldehydes over Ketones with Sodium Tris (hexafluroisopropoxy)borohydride", Synlett, No. 16, pp. 2523-2525 (2008).
International Search Report from the Japanese Patent Office for international Application No. PCT/JP2013/079389 mailed Jan. 23, 2014.

*Primary Examiner* — Paul V Ward
(74) *Attorney, Agent, or Firm* — Finnegan, Henderson, Farabow, Garrett & Dunner, LLP

(57) ABSTRACT

Provided is an oligonucleic acid analog which contains, as at least one structural unit thereof, a modified nucleic acid monomer compound which is a ring-open nucleoside having a cleaved carbon-carbon bond between the 2' and 3' positions and a substituent hydroxymethyl group at the 4' position. When used as siRNA, the oligonucleic acid analog exhibits superior biological stability and target gene expression inhibiting activity. The oligonucleic acid analog can be used in antisense methods, ribozyme methods, and decoy methods, etc., can be used as a nucleic acid aptamer, and can also be used as a nucleic acid probe or molecular beacon, etc., or in genetic diagnostics, etc.

8 Claims, No Drawings

SEQUENCE LISTING

<160> NUMBER OF SEQ ID NOS: 9

<210> SEQ ID NO 1
<211> LENGTH: 21
<212> TYPE: DNA
<213> ORGANISM: Artificial Sequence
<220> FEATURE:

<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide
<220> FEATURE:
<221> NAME/KEY: modified_base
<222> LOCATION: (1)..(1)
<223> OTHER INFORMATION: 2F-O-methylcytidine
<220> FEATURE:
<221> NAME/KEY: modified_base
<222> LOCATION: (2)..(2)
<223> OTHER INFORMATION: 2F-O-methyluridine
<220> FEATURE:
<221> NAME/KEY: modified_base
<222> LOCATION: (3)..(3)
<223> OTHER INFORMATION: 2F-O-methyluridine
<220> FEATURE:
<221> NAME/KEY: modified_base
<222> LOCATION: (5)..(5)
<223> OTHER INFORMATION: 2F-O-methylcytidine
<220> FEATURE:
<221> NAME/KEY: modified_base
<222> LOCATION: (7)..(7)
<223> OTHER INFORMATION: 2F-O-methylcytidine
<220> FEATURE:
<221> NAME/KEY: modified_base
<222> LOCATION: (8)..(8)
<223> OTHER INFORMATION: 2F-O-methyluridine
<220> FEATURE:
<221> NAME/KEY: modified_base
<222> LOCATION: (12)..(12)
<223> OTHER INFORMATION: 2F-O-methyluridine
<220> FEATURE:
<221> NAME/KEY: modified_base
<222> LOCATION: (14)..(14)
<223> OTHER INFORMATION: 2F-O-methylcytidine
<220> FEATURE:
<221> NAME/KEY: modified_base
<222> LOCATION: (15)..(15)
<223> OTHER INFORMATION: 2F-O-methyluridine
<220> FEATURE:
<221> NAME/KEY: modified_base
<222> LOCATION: (16)..(16)
<223> OTHER INFORMATION: 2F-O-methyluridine
<220> FEATURE:
<221> NAME/KEY: modified_base
<222> LOCATION: (17)..(17)
<223> OTHER INFORMATION: 2F-O-methylcytidine

<400> SEQUENCE: 1
cuuacgcuga guacuucgat t                                               21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide
<220> FEATURE:
<221> NAME/KEY: modified_base
<222> LOCATION: (7)..(7)
<223> OTHER INFORMATION: Nucleotide unit
<220> FEATURE:
<221> NAME/KEY: modified_base
<222> LOCATION: (11)..(11)
<223> OTHER INFORMATION: 2F-O-methylcytidine
<220> FEATURE:
<221> NAME/KEY: modified_base
<222> LOCATION: (16)..(16)
<223> OTHER INFORMATION: 2F-O-methyluridine
<220> FEATURE:
<223> OTHER INFORMATION: See specification as filed for detailed description of substitutions and preferred embodiments

<400> SEQUENCE: 2
ucgaaguacu cagcguaagt t                                                21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (7)..(7)
<223> OTHER INFORMATION: Nucleotide unit
<220> FEATURE:
<221> NAME/KEY: modified_base
<222> LOCATION: (11)..(11)
<223> OTHER INFORMATION: 2F-O-methylcytidine
<220> FEATURE:
<221> NAME/KEY: modified_base
<222> LOCATION: (16)..(16)
<223> OTHER INFORMATION: 2F-O-methyluridine
<220> FEATURE:
<223> OTHER INFORMATION: See specification as filed for detailed
      description of substitutions and preferred embodiments

<400> SEQUENCE: 3
ucgaaguacu cagcguaagt t                                                21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2F-O-methylcytidine
<220> FEATURE:
<221> NAME/KEY: modified_base
<222> LOCATION: (2)..(2)
<223> OTHER INFORMATION: 2F-O-methyluridine
<220> FEATURE:
<221> NAME/KEY: modified_base
<222> LOCATION: (3)..(3)
<223> OTHER INFORMATION: 2F-O-methyluridine
<220> FEATURE:
<221> NAME/KEY: modified_base
<222> LOCATION: (5)..(5)
<223> OTHER INFORMATION: 2F-O-methylcytidine
<220> FEATURE:
<221> NAME/KEY: modified_base
<222> LOCATION: (7)..(7)
<223> OTHER INFORMATION: 2F-O-methylcytidine
<220> FEATURE:
<221> NAME/KEY: modified_base
<222> LOCATION: (8)..(8)
<223> OTHER INFORMATION: 2F-O-methyluridine
<220> FEATURE:
<221> NAME/KEY: modified_base
<222> LOCATION: (12)..(12)
<223> OTHER INFORMATION: 2F-O-methyluridine
<220> FEATURE:
<221> NAME/KEY: modified_base
<222> LOCATION: (14)..(14)

-continued

```
<223> OTHER INFORMATION: 2F-O-methylcytidine
<220> FEATURE:
<221> NAME/KEY: modified_base
<222> LOCATION: (15)..(15)
<223> OTHER INFORMATION: 2F-O-methyluridine
<220> FEATURE:
<221> NAME/KEY: modified_base
<222> LOCATION: (16)..(16)
<223> OTHER INFORMATION: 2F-O-methyluridine
<220> FEATURE:
<221> NAME/KEY: modified_base
<222> LOCATION: (17)..(17)
<223> OTHER INFORMATION: 2F-O-methylcytidine
<220> FEATURE:
<221> NAME/KEY: MISC_FEATURE
<222> LOCATION: (20)..(21)
<223> OTHER INFORMATION: Phosphorothioate binding

<400> SEQUENCE: 4
cuuacgcuga guacuucgat t                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (7)..(7)
<223> OTHER INFORMATION: 2F-O-methyluridine
<220> FEATURE:
<221> NAME/KEY: modified_base
<222> LOCATION: (11)..(11)
<223> OTHER INFORMATION: 2F-O-methylcytidine
<220> FEATURE:
<221> NAME/KEY: modified_base
<222> LOCATION: (16)..(16)
<223> OTHER INFORMATION: 2F-O-methyluridine
<220> FEATURE:
<221> NAME/KEY: misc_feature
<222> LOCATION: (20)..(21)
<223> OTHER INFORMATION: Phosphorothioate linkage

<400> SEQUENCE: 5
ucgaaguacu cagcguaagt t                                              21

<210> SEQ ID NO 6
<211> LENGTH: 52
<212> TYPE: DNA
<213> ORGANISM: Artificial Sequence
<220> FEATURE:
<223> OTHER INFORMATION: Description of Artificial Sequence: Synthetic
      sense chain oligonucleotide in vector OFF#085
<220> FEATURE:
<223> OTHER INFORMATION: Description of Combined DNA/RNA Molecule:
      Synthetic sense chain oligonucleotide in vector OFF#085

<400> SEQUENCE: 6
tcgaggtgga catcacttac gctgagtact tcgaaatgtc cgttgctagc gc            52

<210> SEQ ID NO 7
<211> LENGTH: 52
<212> TYPE: DNA
<213> ORGANISM: Artificial Sequence
<220> FEATURE:
<223> OTHER INFORMATION: Description of Artificial Sequence: Synthetic
      antisense chain oligonucleotide in vector OFF#085
<220> FEATURE:
```

```
<223> OTHER INFORMATION: Description of Combined DNA/RNA Molecule:
      Synthetic antisense chain oligonucleotide in vector OFF#085

<400> SEQUENCE: 7
ggccgcgcta gcaacggaca tttcgaagta ctcagcgtaa gtgatgtcca cc          52

<210> SEQ ID NO 8
<211> LENGTH: 52
<212> TYPE: DNA
<213> ORGANISM: Artificial Sequence
<220> FEATURE:
<223> OTHER INFORMATION: Description of Artificial Sequence: Synthetic
      sense chain oligonucleotide in vector OFF#086
<220> FEATURE:
<223> OTHER INFORMATION: Description of Combined DNA/RNA Molecule:
      Synthetic sense chain oligonucleotide in vector OFF#086

<400> SEQUENCE: 8
tcgagaacgg acatttcgaa gtactcagcg taagtgatgt ccacgctagc gc          52

<210> SEQ ID NO 9
<211> LENGTH: 52
<212> TYPE: DNA
<213> ORGANISM: Artificial Sequence
<220> FEATURE:
<223> OTHER INFORMATION: Description of Artificial Sequence: Synthetic
      antisense chain oligonucleotide in vector OFF#086
<220> FEATURE:
<223> OTHER INFORMATION: Description of Combined DNA/RNA Molecule:
      Synthetic antisense chain oligonucleotide in vector OFF#086

<400> SEQUENCE: 9
ggccgcgcta gcgtggacat cacttacgct gagtacttcg aaatgtccgt tc          52
```

MODIFIED NUCLEIC ACID

SEQUENCE LISTING

The instant application contains a Sequence Listing which has been submitted electronically in ASCII format and is hereby incorporated by reference in its entirety. Said ASCII copy, created on Sep. 30, 2015, is named 01197.0336_SL.txt and is 6,241 bytes in size.

TECHNICAL FIELD

The present invention relates to an open circular modified nucleic acid monomer compound and an oligonucleic acid analog containing the monomer compound. More specifically, the present invention relates to an open circular modified nucleic acid monomer compound that has a carbon-carbon bond cleaved at the 2'- and 3'-positions of a nucleoside and has a substituted hydroxymethyl group at the 4'-position, and an oligonucleic acid analog containing the monomer compound as at least one constituent unit.

BACKGROUND OF INVENTION

The atom numbering of the sugar moiety of a nucleic acid monomer shown herein follows atom numbering routinely used on the basis of naturally occurring ribonucleotides (adenosine, cytidine, guanosine, uridine, etc.) (see chemical structural formulas given below). Also, the atom numbering of a naturally occurring nucleobase follows atom numbering routinely used for each of pyrimidine bases (thymine, uracil, and cytosine) and purine bases (adenine, guanine, and hypoxanthine) (see chemical structural formulas given below). The same holds true for substitution products derived therefrom. However, the atom numbering of a heterocyclic ring that is not derived therefrom follows atom numbering generally used.

[Formula 1]

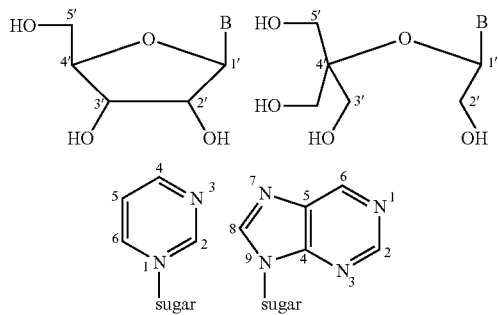

With rapid progress or development of leading-edge research on biotechnology including genomic drug discovery; genetic diagnosis, genetic therapy; etc, various oligonucleic acids such as DNA and RNA have been increasingly used in treatment, diagnosis, and the like in recent years.

The use of oligonucleic acids in treatment includes the inhibition of the expression of a target gene related to a disease or the inhibition of the functions of a target protein. Promising treatment methods are, for example: an antisense method which involves forming double-stranded DNA/mRNA or RNA/mRNA through Watson-Crick hydrogen bonding from single-stranded DNA or RNA complementary to target mRNA to inhibit the translation process of the mRNA into a target protein; an antigene method which involves forming a triplex using an artificial nucleic acid for double-stranded DNA principally constituting a target gene to suppress the expression of the target gene at the transcription level, a decoy method which involves designing double-stranded DNA having a sequence common to a gene recognized by a transcription factor, which is a protein that recognizes a particular double-stranded DNA sequence on the chromosome and regulates gene expression, and administering this double-stranded DNA into cells, thereby suppressing the transcription through the inhibition of the binding of the transcription factor to the target gene; and nucleic acid aptamers that inhibit the functions of a protein through specific binding to a target protein molecule on the basis of the three-dimensional structure of a nucleic acid; and a ribozyrne method which involves inhibiting the translation of mRNA into a target protein through hydrolysis with nuclease such as RNase or DNase.

The use of oligonucleic acids in diagnosis includes, for example, a method which involves constructing an artificial nucleic acid having a sequence specifically binding to a target gene related to a disease, and using this artificial nucleic acid as a probe to diagnose the disease. Another method employs, as a DNA probe, a molecular beacon that has a stem-loop structure and contains a fluorescent substance and a fluorescence emission-inhibiting substance (quencher) in Its structure so as to emit fluorescence upon binding to target RNA.

RNA interference (RNAi) is basically a phenomenon where a double-stranded RNA of approximately 100 base pairs homologous to a particular region in a target gene to be functionally inhibited is transferred into cells and degraded by the action of dicer in the cytoplasm into double-stranded RNAs of approximately 20 to 25 base pairs, which then form RNA/protein complexes (RISC: RNA-induced silencing complex) with a plurality of proteins so that this complex binds to the homologous site of mRNA produced from the target gene to strongly suppress the expression of the target gene (Non Patent Literature 1). Recently, it has been revealed that use of an artificially synthesized short double-stranded RNA of 20 to 24 bases (small interfering RNA: siRNA) also causes a similar phenomenon. A method suppressing the expression of a target gene by use of such siRNA has received attention not only as a useful research approach but as application to pharmaceutical use. This RNAi method is reportedly effective for suppressing gene expression at a very low concentration, for example, when compared with the antisense method, and is expected as a potent method for treating diseases caused by various viruses and genetic diseases, which have previously been considered to be difficult to cure.

A naturally occurring DNA oligomer or RNA oligomer, when used in the antisense method or the RNAi method described above, is very unstable biologically, because the oligomer undergoes rapid hydrolysis by various nucleases in blood. In order to solve such a problem, a modified nucleic acid in which a phosphate binding site in the nucleic acid is converted to a methyl phosphorate bond, a modified nucleic acid in which a phosphate binding site is converted to a phosphorothioate bond, or the like is well known.

Also, it has been reported that as an open circular modified nucleic acid having a carbon-carbon bond cleaved at the 2'- and 3'-positions, an UNA (unlocked nucleic acid: 2',3'-seco-RNA) monomer represented by the following formula:

[Formula 2]

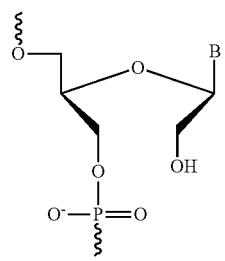

wherein B represents a nucleobase can be introduced to siRNA to thereby enhance the stability of the siRNA in blood, increase its degrading activity against a target gene, and suppress an off-targeting effect (Non Patent Literature 2). Alternatively, Patent Literature 1 has proposed the Introduction of an UNA monomer represented by the following formula:

[Formula 3]

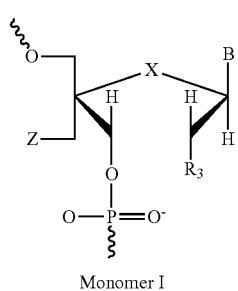

Monomer I

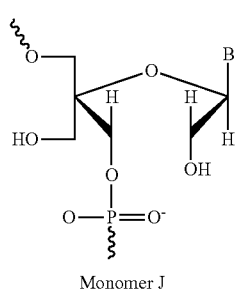

Monomer J

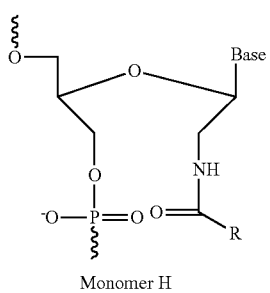

Monomer H

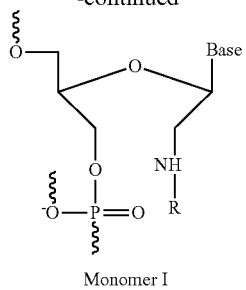

Monomer I wherein Z represents H, OH, CH$_2$OH, CH$_3$, or a C$_{2\text{-}22}$ alkyl strand into siRNA.

CITATION LIST

Patent Literature

Patent Literature 1: International Publication No. WO2011/139710

Non Patent Literature

Non Patent Literature 1: Fire et al., Nature, 391, 806-811 (1998)
Non Patent Literature 2: Pasternak et al., Org. Biomol. Chem., 9, 3591-3597, 2011

SUMMARY OF INVENTION

Technical Problem

Many modified nucleic acids have been proposed so far in order to improve biological stability and enhance suppressive activity against the expression of a target gene. Unfortunately, none of these modified nucleic acids are found sufficient under the present circumstances.

Thus, an object of the present invention is to provide an open circular modified nucleic acid monomer compound that can yield an oligonucleic acid analog excellent in biological stability (e.g., stability in blood) and suppressive activity against the expression of a target gene, and an oligonucleic acid analog containing the monomer compound as a constituent unit.

Solution to Problem

The present inventors have conducted diligent studies to attain the object and consequently found that: when an open circular nucleoside that has a carbon-carbon bond cleaved at the 2'- and 3'-positions and has a substituted hydroxymethyl group at the 4'-position is used as a modified nucleic acid monomer compound and an oligonucleic acid analog containing the modified nucleic acid monomer compound as at least one constituent unit is used as, for example, siRNA, the resulting siRNA has improved biological stability and enhanced suppressive activity against the expression of a target gene; such an oligonucleic acid analog can be applied to the antisense method, the ribozyme method, the decoy method, etc.; the oligonucleic acid analog can also be used as a nucleic acid aptamer or the like; and the oligonucleic acid analog can be applied as a nucleic acid probe, a molecular beacon, or the like to genetic diagnosis, etc. On the basis of these findings, the present invention has been completed.

Thus, the present invention relates to:

[1] a compound represented by the following formula (I):

[Formula 4]

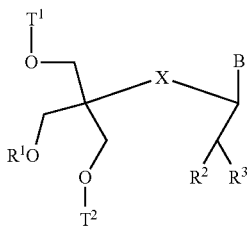

(I)

wherein

B represents an optionally substituted heterocyclic group;

T¹ represents a protective group for a hydroxy group, or a hydrogen atom;

T² represents a phosphorus-containing functional group, a protective group for a hydroxy group, or a hydrogen atom;

X represents an oxygen atom, a sulfur atom, —C(E¹)(E²)—, —C(=O)—, —C(=S)—, —C(=C(E¹)(E²))—, —N(E³)—, or —C(=NE³)—;

E¹ and E² each independently represent a hydrogen atom, a halogen atom, an optionally substituted hydroxy group, an optionally substituted $C_{1-6}$ alkyl group, an optionally substituted $C_{2-6}$ alkenyl group, or an optionally substituted amino group;

E³ represents a hydrogen atom, an optionally substituted $C_{1-6}$ alkyl group, or an optionally substituted $C_{2-6}$ alkenyl group;

R¹ represents an optionally substituted $C_{1-6}$ alkyl group, an optionally substituted $C_{2-6}$ alkenyl group, or an optionally substituted amino group;

R² represents an optionally substituted hydroxy group, an optionally substituted amino group, a hydrogen atom, an optionally substituted $C_{1-6}$ alkyl group, an optionally substituted $C_{2-6}$ alkenyl group, an optionally substituted $C_{2-6}$ alkynyl group, or a halogen atom; and R³ represents a hydrogen atom, an optionally substituted hydroxy group, an optionally substituted amino group, a hydrogen atom, an optionally substituted $C_{1-6}$ alkyl group, an optionally substituted $C_{2-6}$ alkenyl group, an optionally substituted $C_{2-6}$ alkynyl group, or a halogen atom, or a salt thereof;

[2] an oligonucleic acid analog comprising one or more partial structures each represented by the following formula (II):

[Formula 5]

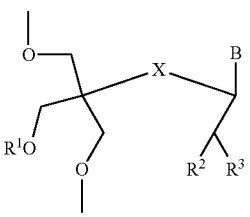

(II)

wherein

B represents an optionally substituted heterocyclic group;

X represents an oxygen atom, a sulfur atom, —C(E¹)(E²)—, —C(=O)—, —C(=S)—, —C(=C(E¹)(E²))—, —N(E³)—, or —C(=NE³)—;

E¹ and E² each independently represent a hydrogen atom, a halogen atom, an optionally substituted hydroxy group, an optionally substituted $C_{1-6}$ alkyl group, an optionally substituted $C_{2-6}$ alkenyl group, or an optionally substituted amino group;

E³ represents a hydrogen atom, an optionally substituted $C_{1-6}$ alkyl group, or an optionally substituted $C_{2-6}$ alkenyl group;

R¹ represents an optionally substituted $C_{1-6}$ alkyl group, an optionally substituted $C_{2-6}$ alkenyl group, or an optionally substituted amino group;

R² represents an optionally substituted hydroxy group, an optionally substituted amino group, a hydrogen atom, an optionally substituted $C_{1-6}$ alkyl group, an optionally substituted $C_{2-6}$ alkenyl group, an optionally substituted $C_{2-6}$ alkynyl group, or a halogen atom; and R³ represents a hydrogen atom, an optionally substituted hydroxy group, an optionally substituted amino group, a hydrogen atom, an optionally substituted $C_{1-6}$ alkyl group, an optionally substituted $C_{2-6}$ alkenyl group, an optionally substituted $C_{2-6}$ alkynyl group, or a halogen atom, or a salt thereof, provided that when the oligonucleic acid analog or the salt thereof comprises two or more of the partial structures, B, R¹, R², and R³ may each be the same or different between or among the partial structures:

[3] a compound represented by the following formula (III):

[Formula 6]

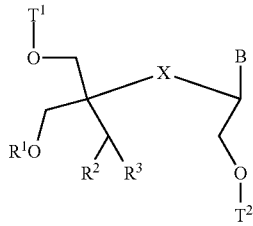

(III)

wherein

B represents an optionally substituted heterocyclic group;

T¹ represents a protective group for a hydroxy group, or a hydrogen atom;

T² represents a phosphorus-containing functional group, a protective group for a hydroxy group, or a hydrogen atom;

X represents an oxygen atom, a sulfur atom, —C(E¹)(E²)—, —C(=O)—, —C(=S)—, —C(=C(E¹)(E²))—, —N(E³)—, or —C(=NE³)—;

E¹ and E² each independently represent a hydrogen atom, a halogen atom, an optionally substituted hydroxy group, an optionally substituted $C_{1-6}$ alkyl group, an optionally substituted $C_{2-6}$ alkenyl group, or an optionally substituted amino group;

E³ represents a hydrogen atom, an optionally substituted $C_{1-6}$ alkyl group, or an optionally substituted $C_{2-6}$ alkenyl group;

R¹ represents an optionally substituted $C_{1-6}$ alkyl group, an optionally substituted $C_{2-6}$ alkenyl group, or an optionally substituted amino group;

$R^2$ represents an optionally substituted hydroxy group, an optionally substituted amino group, a hydrogen atom, an optionally substituted $C_{1-6}$ alkyl group, an optionally substituted $C_{2-6}$ alkenyl group, an optionally substituted $C_{2-6}$ alkynyl group, or a halogen atom; and $R^3$ represents a hydrogen atom, an optionally substituted hydroxy group, an optionally substituted amino group, a hydrogen atom, an optionally substituted $C_{1-6}$ alkyl group, an optionally substituted $C_{2-6}$ alkenyl group, an optionally substituted $C_{2-6}$ alkynyl group, or a halogen atom,
or a salt thereof;

[4] an oligonucleic acid analog comprising one or more partial structures each represented by the following formula (IV):

[Formula 7]

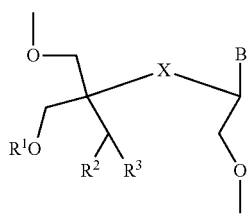

(IV)

wherein

B represents an optionally substituted heterocyclic group;

X represents an oxygen atom, a sulfur atom, —C($E^1$)($E^2$)—, —C(=O)—, —C(=S)—, —C(=C($E^1$)($E^2$))—, —N($E^3$)—, or —C(=N$E^3$)—;

$E^1$ and $E^2$ each independently represent a hydrogen atom, a halogen atom, an optionally substituted hydroxy group, an optionally substituted $C_{1-6}$ alkyl group, an optionally substituted $C_{2-6}$ alkenyl group, or an optionally substituted amino group;

$E^3$ represents a hydrogen atom, an optionally substituted $C_{1-6}$ alkyl group, or an optionally substituted $C_{2-6}$ alkenyl group;

$R^1$ represents an optionally substituted $C_{1-6}$ alkyl group, an optionally substituted $C_{2-6}$ alkenyl group, or an optionally substituted amino group;

$R^2$ represents an optionally substituted hydroxy group, an optionally substituted amino group, a hydrogen atom, an optionally substituted $C_{1-6}$ alkyl group, an optionally substituted $C_{2-6}$ alkenyl group, an optionally substituted $C_{2-6}$ alkynyl group, or a halogen atom; and $R^3$ represents a hydrogen atom, an optionally substituted hydroxy group, an optionally substituted amino group, a hydrogen atom, an optionally substituted $C_{1-6}$ alkyl group, an optionally substituted $C_{2-6}$ alkenyl group, an optionally substituted $C_{2-6}$ alkynyl group, or a halogen atom,
or a salt thereof,
provided that when the oligonucleic acid analog or the salt thereof comprises two or more of the partial structures, B, $R^1$, $R^2$, and $R^3$ may each be the same or different between or among the partial structures;

[5] the compound according to [1] or [3], wherein B is an adenine-derived group or a guanine-derived group, or a salt thereof;

[6] the compound according to [1] or [3], wherein $R^1$ is a $C_{1-6}$ alkyl group, or a salt thereof;

[7] the oligonucleic acid analog according to [2] or [4], wherein B is an adenine-derived group or a guanine-derived group, or a salt thereof; and

[8] the oligonucleic acid analog according to [2] or [4], wherein $R_3$ is a $C_{1-6}$ alkyl group, or a salt thereof.

Advantageous Effects of Invention

When an oligonucleic acid analog containing the open circular modified nucleic acid monomer compound of the present invention as at least one partial structure is used as, for example, siRNA, the resulting siRNA is excellent in biological stability (e.g., stability in blood) and suppressive activity against the expression of a target gene. In addition, such an oligonucleic acid analog can also be used as antisense RNA, antisense DNA, a decoy nucleic acid, a nucleic acid aptamer, a ribozyme, or the like. The oligonucleic acid analog may be further used as a genetic analysis tool such as an RNA probe, a DNA probe, or a molecular beacon.

DESCRIPTION OF EMBODIMENTS

Hereinafter, the terms, etc, described herein will be defined, and the present invention will be described in detail.

In the present specification, the halogen atom refers to, for example, a fluorine atom, a chlorine atom, a bromine atom, or an iodine atom.

The $C_{1-6}$ alkyl group refers to, for example, methyl, ethyl, n-propyl, isopropyl, n-butyl, isobutyl, t-butyl, n-pentyl, isopentyl, neopentyl, n-hexyl, 1-methylpropyl, 1,2-dimethylpropyl, 1-ethylpropyl, 1-methyl-2-ethylpropyl, 1-ethyl-2-methylpropyl, 1,1,2-trimethylpropyl, 1-methylbutyl, 2-methylbutyl, 1,1-dimethylbutyl, 2,2-dimethylbutyl, 2-ethylbutyl, 1,3-dimethylbutyl, 2-methylpentyl, or 3-methylpentyl. Among them, methyl is preferred.

The $C_{2-6}$ alkenyl group refers to, for example, vinyl, allyl, 1-propenyl, isopropenyl, 1-buten-1-yl, 1-buten-2-yl, 1-buten-3-yl, 2-buten-1-yl, or 2-buten-2-yl.

The $C_{2-6}$ alkynyl group refers to, for example, ethynyl, 1-propynyl, 2-propynyl, butynyl, pentynyl, or hexynyl.

The $C_{1-6}$ alkoxy group refers to, for example, methoxy, ethoxy, n-propoxy, isopropoxy, n-butoxy, isobutoxy, sec-butoxy, t-butoxy, n-pentoxy, isopentoxy, sec-pentoxy, t-pentoxy, n-hexoxy, isohexoxy, 1,2-ditmethylpropoxy, 2-ethylpropoxy, 1-methyl-2-ethylpropoxy, 1-ethyl-2-methylpropoxy, 1,1,2-trimethylpropoxy, 1-dimethylbutoxy, 2,2-dimethylbutoxy, 2-ethylbutoxy, 1,3-dimethylbutoxy, 2-methylpentoxy, 3-methylpentoxy, or hexyloxy.

The $C_{1-6}$ alkylthio group refers to, for example, methylthio, ethylthio, n-propylthio, isopropylthio, n-butylthio, isobutylthio, t-butylthio, n-pentylthio, isopentylthio, neopentylthio, n-hexylthio, or 1-methylpropylthio.

The $C_{1-6}$ alkylsulfonyl group refers to, for example, methylsulfonyl, ethylsulfonyl, n-propylsulfonyl, isopropylsulfonyl, n-butylsulfonyl, isobutylsulfonyl, t-butylsulfonyl, n-pentylsulfonyl, isopentylsulfonyl, neopentylsulfonyl, n-hexylsulfonyl, or 1-methylpropylsulfonyl.

The $C_{1-6}$ alkyl-carbonyl group refers to acetyl, propionyl, or butyryl.

The $C_{6-14}$ aryloxy-carbonyl group refers to, for example, phenyloxycarbonyl, naphthyloxycarbonyl, or anthryloxycarbonyl.

The $C_{6-14}$ aryl-carbonyl group refers to, for example, benzoyl or naphthoyl. Among them, benzoyl is preferred.

The $C_{6-14}$ arylsulfonyl group refers to, for example, benzenesulfonyl or naphthylsulfonyl.

The mono-$C_{1-6}$ alkylamino group refers to, for example, monomethylamino, monoethylamino, mono-n-propylamino, monoisopropylamino, mono-n-butylamino, monoisobutylanimo, mono-t-butylanmino, mono-n-pentylamino, monoisopentylamino, or mononeopentylamino.

The di-$C_{1-6}$ alkylamino group refers to, for example, dimethylamino, diethylamino, di-n-propylamino, diisopropylamino, di-n-butylamino, diisobutylamino, di-t-butylamino, di-n-pentylamino, diisopentylamino, or dineopentylamino.

In the present specification, the chemical structural formula of a compound represents isomers. The present invention includes all isomers generated in terms of the structure of the compound, such as geometric isomers, optical isomers based on asymmetric carbon, stereoisomers, and tautomers, and mixtures of these isomers. Such a compound is not limited by the description of the chemical structural formula and may be any one of the isomers or may be any isomeric mixture. Thus, optically active forms and racemates having asymmetric carbon atoms in their molecules may be present. However, the present invention includes, but not limbed to, any of these forms.

Hereinafter, the open circular modified nucleic acid monomer compound of the present invention and an oligonucleic acid analog containing the monomer compound as at least one constituent unit will be described in detail.

1. Open Circular Modified Nucleic Acid Monomer Compound

The open circular modified nucleic acid monomer compound of the present invention is represented by the following formula (I) or (III):

[Formula 8]

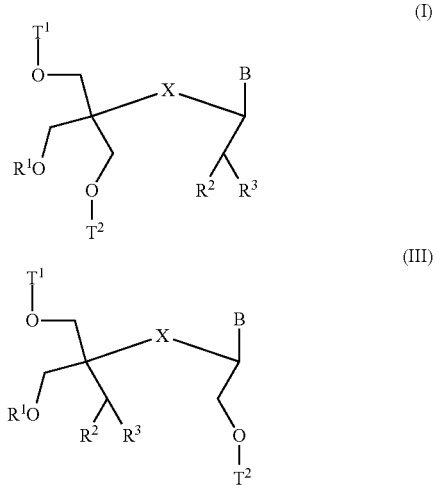

The open circular modified nucleic acid monomer compound of the formula (I) can be used in the production of an oligonucleic acid derivative having bonds at the 3'- and 5'-positions by the involvement of —O-$T^2$ at the 3'-position and —O-$T^1$ at the 5'-position in binding to nucleotides constituting the oligonucleic acid analog. The open circular modified nucleic acid monomer compound of the formula (III) can be used in the production of an oligonucleic acid derivative having bonds at the 2'- and 5'-positions by the involvement of —O-$T^2$ at the 2'-position and —O-$T^1$ at the 5'-position in binding to nucleotides constituting the oligonucleic acid analog. The common features of the open circular modified nucleic acid monomer compound of the formula (I) and the open circular modified nucleic acid monomer compound of the formula (III) are to have a carbon-carbon bond cleaved at the 2'- and 3'-positions and have a substituted hydroxymethyl group at the deposition.

In the formulas (I) and (III), B represents an optionally substituted heterocyclic group. The heterocyclic group in the optionally substituted heterocyclic group includes (1) a base of a naturally occurring nucleoside (e.g., adenine, cytosine, guanine, thymine, or uracil) (in the present specification, also referred to as a "naturally occurring base"), (2) a base different from the naturally occurring base, and (3) other heterocyclic groups.

Examples of the base (2) different from the naturally occurring base include (i) a base added to each of nebularine, isoguanosine, isocytidine, and tubercidin, and (ii) a base having the same structure as that of the naturally occurring base, but differing therefrom in the binding (substitution) site with a sugar (e.g., pseudouridine).

Examples of other heterocyclic groups (3) described above include $C_{5-10}$ heterocyclic groups such as piperidinyl, pyrrolidinyl, piperazinyl, morpholinyl, thiomorpholinyl, pyrrolyl, imidazolyl, pyrazolyl, pyridinyl, pyridazinyl, pyrimidinyl, pyrazinyl, triazolyl, tetrazolyl, isoxazolyl, oxazolyl, oxadiazolyl, isothiazolyl, thiazolyl, thiadiazolyl, furyl, thienyl, quinolinyl, isoquinolinyl, benzofuryl, benzopyranyl, benzimidazolyl, benzotriazolyl, benzisothiazolyl, indolinyl, isoindolinyl chromanyl, isochromanyl, 1,3-dioxaindanyl, and 1,4-dioxatetralinyl, and chemically synthesized nucleobases. The chemically synthesized nucleobases may be those generally called universal bases in a broad sense. For these nucleobases, see literatures such as Loakes, Nucleic Acids Research, Vol. 29, pp. 2437-2447, 2001; and Englisch and Gauss, Angew. Chem. Int. Ed., Vol. 30, pp. 613-722, 1991.

Examples of substituents for the optionally substituted heterocyclic group include 1 to 3 substituents selected from a halogen atom, a $C_{1-6}$ alkyl group, a $C_{1-6}$ alkoxy group, a $C_{2-6}$ alkenyl group, a $C_{2-6}$ alkynyl group, a $C_{1-6}$ alkylcarbonyl group, a $C_{1-6}$ alkylthio group, a $C_{1-6}$ alkylsulfonyl group, a $C_{6-14}$ aryloxy-carbonyl group, a $C_{6-14}$ aryl-carbonyl group, a $C_{6-14}$ arylsulfonyl group, an amino group, a mono-$C_{1-6}$ alkylamino group, a di-$C_{1-6}$ alkylamino group, a nitro group, a hydroxy group, a cyano group, and a carboxy group. Of these substituents, the $C_{1-6}$ alkyl group, the $C_{1-6}$ alkoxy group, the $C_{2-6}$ alkenyl group, the $C_{2-6}$ alkynyl group, the $C_{1-6}$ alkyl-carbonyl group, the $C_{1-6}$ alkylthio group, the $C_{1-6}$ alkylsulfonyl group, the $C_{6-14}$ aryloxy-carbonyl group, the $C_{6-14}$ aryl-carbonyl group, the $C_{6-14}$ arylsulfonyl group, and the like may each be further substituted by 1 to 3 substituents selected from a halogen atom, an amino group, a mono-$C_{1-6}$ alkylamino group, and a di-$C_{1-6}$ alkylamino group.

These optional substituents in the heterocyclic group may be protective groups. If each substituent described above is capable of functioning as a protective group in itself, this substituent may be used as a protective group. Examples of the protective groups include protective groups for amino groups, protective groups for hydroxy groups, and protective groups for carboxy groups.

Examples of the protective groups for amino groups include: carbamate protective groups such as t-butoxycarbonyl, benzyloxycaxbonyl 9-fluorenylmethyloxycarbonyl, 2,2,2-trichloroethoxycarbonyl, and allyloxycarbonyl; acyl protective groups such as acetyl, chloroacetyl, dichioroacetyl, trichloroacetyl, fluoroacetyl, difluoroacetyl, trifluoroacetyl, benzoyl, and 2-nitrobenzoyl; imide protective groups such as phthaloyl; sulfonyl protective groups such as tosyl and 2-nitrobenzenesulfonyl, phenyl protective groups such as 4-methoxyphenyl; and benzyl protective groups such as benzyl, 4-methoxybenzyl, and 3,4-dimethoxybenzyl.

Examples of the protective groups for hydroxy groups can include the same protective groups as those exemplified later as a protective group for a hydroxy group represented by $T^1$.

Examples of the protective groups for carboxy groups can include ester protective groups such as methyl ester, ethyl ester, t-butyl ester, and benzyl ester.

Specific examples of B as the optionally substituted heterocyclic group in the formulas (I) and (III) include: adenine-derived groups such as adenine, 2-fluoroadenine, 2-methyladenine, 2-propyladenine, 2-aminoadenine, 2-aminomethyladenine, 2-aminopropyladenine, 2-methylthio-$N^6$-isopentenyladenine, $N^6$-propyladenine, $N^6$-methyladenine, 7-deazaadenine, 8-aza-7-deazaadenine, 8-vinyladenine, 8-methyladenine, 8-ethynyladenine, 8-phenyladenine, 8-aminoadenine, 8-fluoroadenine, 8-hydroxyladenine, 8-methoxyadenine, 8-methylthioadenine, 8-mercaptoadenine, $N^6$-isopentyladenine, and $N^6,N^6$-dimethyadenine; guanine-derived groups such as guanine, 2-methylguanine, 2-propylguanine, $O^6$-methylguanine, $O^6$-ethylguanine, 7-methylguanine, 7-ethylguanine, 7-deazaguanine, 8-methylguanine, 8-vinylguanine, 8-ethynylguanine, 8-phenylguanine, 8-aminoguanine, 8-fluoroguanine, 8-hydroxylguanine, 8-methoxyguanine, 8-methylthioguanine, 8-mercaptoguanine, and $N^2$-methylguanine; cytosine-derived groups such as cytosine, 2-thiocytosine, 3-deaza-5-azacytosine, 3-methylcytosine, 3-ethylcytosine, 5-methylcytosine, 5-vinylcytosine, 5-ethynylcytosine, 5-fluorocytosine, 5-methylcytosine, 5-propenylcytosine, 5-ethynylcytosine, 5-trifluoromethylcytosine, 6-azacytosine, and $N^4$-acetylcytosine; uracil-derived groups such as uracil, 3-(3-amino-carboxypropyl)uracil, 2-thiouracil, 5-methyl-2-thiouracil, 5-methylaminomethyl-2-thiouracil, 4-thiouracil, 5-methyl-4-thiouracil, 5-methylaminomethyl-4-thiouracil, 5-methyl-2,4-dithiouracil, 5-methylaminomethyl-2,4-dithiouracil, 5-(2-aminopropyl)uracil, 5-guanidinoalkyluracil, 5-(1,3-diazo-1-yl-alkyl)uracil, 5-cyanomethyluracil, 5-dimethylaminoethyluracil, 5-dimethylaminoethyluracil, 5-fluorouracil, 5-methoxyuracil, uracil-5-oxyacetic acid, 5-methoxycarbonylmethyl-2-thiouracil, 5-methoxycarbonylmethyluracil, 5-propynyluracil, 5-propynyluracil, 5-ethynyluracil, 5-trifluoromethyluracil, 6-azauracil, 5,6-dihydrouracil, $N^3$-methyluracil, uracil-5-yl (pseudouracil), 2-thiopseudouracil, 4-thiopseudouracil, 2,4-dithiopseudouracil, 1-methylpseudouracil, 1-methylpseudouracil, 1-methyl-2-thiopseudouracil, 1-methyl-4-thiopseudouracil, 1-methyl-2,4-dithiopseudouracil, 1-ethyl-2-thiopseudouracil, 1-ethyl-4-thiopseudouracil, 1-ethyl-2,4-dithiopseudouracil, 1-aminocarbonylethylenyl-2-thiopseudouracil, 1-aminocarbonylethylenyl-4-thiopseudouracil, and 1-aminocarbonylethylenyhl-2,4-dithiopseudouracil; phenoxazine-derived groups such as 1,3-diaza-2-oxophenoxazin-1-yl, 1-aza-2-thio-3-azaphenoxazin-1-yl, 7-aminomethylhydroxy-1,3-diaza-2-thiophenoxazin-1-yl, 7-aminomethylhydroxyl-1,3-diaza-2-oxophenoxazin-1-yl, 7-guanidiummethylhydroxy-1,3-diaza-2-oxophenoxazin-1-yl, and 7-guanidiummethylhydroxy-1,3-diaza-2-thiophenoxazin-1-yl; phenothiazine-derived groups such as 1,3-diaza-2-oxophenothiazin-1-yl, 1-aza-2-thio-3-azaphenothiazin-1-yl, 7-aminoalkylhydroxy-1,3-diaza-2-thiophenothiazine; naphthalene-derived groups such as 1,3,5-triaza-2,6-dioxanaphthalene; xanthine-derived groups such as xanthine and hypoxanthine; inosinyls such as inosinyl, 2-azainosinyl, and 7-deazainosinyl; imidazolyl-derived groups such as nitromidazolyl and nitrobenzimidazolyl; indazolyl-derived groups such as nitropyrazolylnitroindazolyl; indolyl-derived groups such as aminoindolyl, 7-azaindolyl, 6-methyl-7-azaindolyl, and 4,6-dimethylindolyl; pyrimidinyl-derived groups such as pyrrolopyrimidinyl and 9-methyl-imidazopyrimidinyl; pyridinyl-derived groups such as pyrrolopyridinyl; carbostyril-derived groups such as 3-methylisocarbostyril, 5-methylisocarbostyril, 3-methyl-7-propynylisocarbostyril, isocarbostyril, 7-propynylisocarbostyril, 3-methylisocarbostyril, 5-methylisocarbostyril, and 3-methyl-7-propynylisocarbostyril; pyridnyl-derived groups such as imidazopyridinyl and pyrrolopyridinyl, indolyls such as propynyl-7-azaindolyl, 4-methylindolyl, 4,6-dimethylindolyl, 7-azaindolyl, 6-methyl-7-azaindolyl, and propynyl-7-azaindolyl; imidazolyl-derived groups such as 4-fluoro-6-methylbenzimidazolyl and 4-methylbenzimidazolyl; thymine-derived groups such as 6-azothyymine; pyridinone-derived groups such as 2-pyridinone; indole-derived groups such as 5-nitroindole; pyrrole-derived groups such as 3-nitropyrrole; pyrimidine-derived groups such as 6-azapyrimidine, pyrrolopyrimidin-2-on-3-yl, 6-phenyl-pyrrolopyrimidin-2-on-3-yl, p-fluoro-6-phenyl-pyrrolopyrimidin-2-on-3-yl, o-fluoro-6-phenyl-pyrrolopyrimidin-2-on-3-yl, bis-o-fluoro-6-phenyl-pyrrolopyrimidin-2-on-3-yl, p-aminoalkylhydroxy-6-phenyl-pyrrolopyrimidin-2-on-3-yl, o-aminoalkylhydroxy-6-phenyl-pyrrolopyrimidin-2-on-3-yl, bis-o-di-aminoalkylhydroxy-6-phenyl-pyrrolopyrimidin-2-on-3-yl, pyridopyrimidin-3-yl, 2-oxo-7-aminopyridopyrimidin-3-yl, and 2-oxo-pyridopyrimidin-3-yl; and purine-derived groups such as 2-aminopurine and 2,6-diaminopurine.

B as the optionally substituted heterocyclic group in the formulas (I) and (III) is preferably a base of a naturally occurring nucleoside, more preferably uracil. According to another preferred embodiment, B is preferably an adenine-derived group or a guanine-derived group, more preferably an adenine-derived group.

In the formulas (I) and (III), $T^1$ represents a protective group for a hydroxy group, or a hydrogen atom. The protective group for a hydroxy group can be any protective group usually used as a protective group for hydroxy groups in nucleic acids. Examples of such protective groups include: silyl-type protective groups such as trimethylsilyl (TMS), triethylsilyl, triisopropylsilyl, isopropyldimethylsilyl, t-butyldimethylsilyl (TBS), (triphenylmethyl)dimethylsilyl, t-butyldiphenylsilyl, methyldiisopropylsilyl, methyldit-butylsilyl, tribenzylsilyl, tri-p-xylylsilyl, triisopropylsilyl, and triphenylsilyl; trityl-type protective groups such as trityl, 4-monomethoxytrityl, 4,4'-dimethoxytrityl (DMTr), and trimethoxytrityl; heterocycle-type protective groups such as tetrahydropyranyl, 3-bromotetrahydropyranyl, tetrahydrothiopyranyl, 4-methoxytetrahydropyranyl, 4-methoxytetrahydrothiopyranyl, 4-methoxytetrahydrothiopyranyl S,S-dioxide, tetrahydrofuranyl, and tetrahydrothiofuranyl; benzyl-type protective groups such as benzyl 4-methoxybenzyl, 2-nitrobenzyl, 4-nitrobenzyl, and 4-cyanobenzyl; aliphatic acyl-type protective groups such as acetyl chloroacetyl, trichloroacetyl, trifluoroacetyl, phenoxyacetyl, butyryl, propionyl, pivaloyl, levulinyl, pentanoyl, valeryl, and octanoyl; aromatic acyl-type protective groups such as benzoyl, 2-fluorobenzoyl, 4-phenylbenzoyl, 2,6-dichlorobenzoyl, 2-toluoyl, 4-methoxybenzoyl, and 2,4,6-trimethylbenzoyl; ether-type protective groups such as butyl, t-butoxymethyl, methoxymethyl, 1-ethoxyethyl, 1-(2-chloroethoxy)ethyl, 2-trimethylsilylethyl, 2-(cyanoethoxy) ethyl (CEE), cyanoethoxymethyl (CEM), 2-naphthylmethyl, diphenylmethyl, 4-chlorophenyl, and 2,4-dinitrophenyl; carbamoyl-type protective groups such as dimethylcarbamoyl and diphenylcarbamoyl; sulfonyl-type protective groups such as mesyl, tosyl, and trifluoromethanesulfonyl, alkoxycarbonyl-type protective groups such as 9-fluorenylmethoxycarbonyl; and xanthine-type protective groups such as 9-phenylxanthin-9-yl (pixyl) and 9-(4-methoxyphenyl)xanthin-9-yl (MOX).

For these protective groups for the hydroxy group, see literatures such as Beaucage et al, Tetrahedron, Vol. 48, pp. 2223-2311, 1992: Greene and Wuts, Protecting Groups in Organic Synthesis, Chapter 2, 2nd Ed., John Wiley & Sons, New York, 1991; and Ekstein et al., Oligonucleotides And Analogures A Practical Approach, IRL Press, N.Y. 1991.

$T^1$ in the formulas (I) and (III) is preferably a protective group for a hydroxy group, more preferably DMTr.

In the formulas I and (III), $T^2$ represents a phosphorus-containing functional group, a protective group for a hydroxy group, or a hydrogen atom. In this context, examples of the protective group for a hydroxy group can include the same protective groups as those exemplified above as the protective group for a hydroxy group represented by $T^1$.

Examples of the phosphorus-containing functional group can include phosphorus-containing functional groups serving as phosphoric acid reactive groups for the production of the oligonucleic acid analog of the formula (II) or (IV) by a known nucleic acid synthesis method such as a triester method, a phosphoramidite method, a method using a dichlorophosphine derivative, or an H-phosphonate method using the open circular modified nucleic acid monomer compound of the formula (I) or (III).

Examples of the phosphorus-containing functional group serving as a phosphoric acid reactive group for the production by the triester method include a phosphorus-containing functional group represented by the following formula (a):

[Formula 9]

(a)

wherein $Y^1$ represents a protective group for the phosphoric acid, and $Z^1$ represents a hydrogen atom or a protective group for the phosphoric acid.

It is preferred for synthesizing the oligonucleic acid analog of the formula (II) or (IV) using the open circular modified nucleic acid monomer compound of the formula (I) or (III) that the protective group for the phosphoric acid represented by $Y^1$ and the protective group for the phosphoric acid represented by $Z^1$ should be different from each other. In this context, examples of the protective group for the phosphoric acid include: protective groups removable by β elimination, such as 2-cyanoethyl, 2-(phenylsulfonyl)ethyl, 2-(4-nitrophenyl)ethyl, 2,2,2-trichloroethyl (TCE), 2,2,2-tribromoethyl, and 2,2,2-trichloro-1,1-dimethylethyl; protective groups removal using fluoride ions (tetrabutylammonium fluoride (TBAF), etc), such as 2-trimethylsilylethyl (TMSE) and 2-(diphenylmethylsilyl)ethyl (DPSE); protective groups removable by cyclization reaction, such as 4-[N-methyl-N-(trifluoroacetyl)amino]butyl (TFAB), 2-[(1-naphthyl)carbamoyloxy]ethyl (NCE), and 4-oxopentyl; protective groups removable by nucleophilic substitution reaction on carbon atoms, such as methyl and 2,4-dinitrobenzyl, protective groups removable by hydrogenolysis, such as benzyl; protective groups removable by substitution reaction using palladium catalysts, such as allyl; and protective groups removable using oximate ions, such as phenyl, 2-chlorophenyl, 8-chloroquinolyl, and phenylthio.

Examples of the phosphorus-containing functional group serving as a phosphoric acid reactive group for the production by the phosphoramidite method include a phosphorus-containing functional group represented by the following formula (b):

[Formula 10]

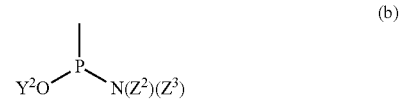

(b)

wherein $Y^2$ represents a protective group for the phosphoric acid, and $Z^2$ and $Z^3$ are the same or different and each represent a $C_{1-6}$ alkyl group, or $Z^2$ and $Z^3$ together form a 5- to 7-membered nitrogen-containing heterocyclic ring optionally further containing a heteroatom, together with the nitrogen atom bonded thereto.

Examples of the protective group for the phosphoric acid represented by $Y^2$ can include the same protective groups as those exemplified above as the protective group for the phosphoric acid represented by $Y^1$ and $Z^1$ in the formula (a). Among others, a protective group for the phosphoric acid routinely used in the phosphoramidite method, such as methyl 2-cyanoethyl, or 2-trimethylsilylethyl is preferred, and 2-cyanoethyl is particularly preferred. Examples of —$NZ^2Z^3$ in the formula (b) can include dimethylamino, diethylamino, di-n-propylamino, diisopropylamino, di-n-butylamino, diisobutylamino, di-t-butylamino, di-n-pentylamino, diisopentylamino, and dineopentylamino. Examples of the 5- to 7-membered nitrogen-containing heterocyclic ring optionally further containing a heteroatom, formed together by $Z^2$ and $Z^3$ together with the nitrogen atom bonded thereto can include morpholin-1-yl and piperidin-1-yl. In this context, examples of the heteroatom include a nitrogen atom, an oxygen atom, and a sulfur atom. Among them, a group routinely used in the phosphoramidite method, such as diisopropylamino or dimethylamino is preferred, and diisopropylamino is particularly preferred.

Examples of the phosphorus-containing functional group serving as a phosphoric acid reactive group for the production by the method using a dichlorophosphine derivative include a phosphorus-containing functional group represented by the following formula (c):

[Formula 11]

(c)

wherein $Y^3$ represents an optionally substituted $C_{1-6}$ alkoxy group, an optionally substituted $C_{6-12}$ aryloxy group, or an allyloxy group, and $Z^4$ represents a halogen atom.

In this context, examples of the optionally substituted $C_{1-6}$ alkoxy group can include methoxy and $C_{1-6}$ alkoxy groups substituted by a halogen atom, such as trichloromethoxy and 2,2,2-trichloro-1,1-dimethylethyloxy. Examples of the optionally substituted $C_{6-12}$ aryloxy group can include $C_{6-12}$ aryloxy groups substituted by a halogen atom, such as 2-chlorophenyloxy. Preferred examples of the halogen atom represented by $Z^4$ include a chlorine atom.

Examples of the phosphorus-containing functional group serving as a phosphoric acid reactive group for the production by the H-phosphonate method include a phosphorus-containing functional group represented by the following formula (d):

[Formula 12]

(d)

wherein $Z^+$ represents a cation.

Examples of the cation represented by $Z^+$ can include: mono-$C_{1-6}$ alkylammonium ions such as methylamino, ethylamino, and isobutylamino; di-$C_{1-6}$ alkylammonium ions such as dimethylammonium ions, diethylammonium ions, and diisobutylammonium ions, and metal ions such as potassium ions and lithium ions.

$T^2$ in the formulas (I) and (III) is preferably a phosphoric acid reactive group for the production by the phosphoramidite method, more preferably a phosphoramidite group (a group represented by the formula (b) wherein $Y^2$ is 2-cyanoethyl, and —$NZ^2Z^3$ is diisopropylamino).

In the formulas (I) and (III), X represents an oxygen atom, a sulfur atom, —$C(E^1)(E^2)$—, —$C(=O)$—, —$C(=S)$—, —$C(=C(E^1)(E^2))$—, —$N(E^3)$—, or —$C(=NE^3)$—; $E^1$ and $E^2$ each independently represent a hydrogen atom, a halogen atom, an optionally substituted hydroxy group, an optionally substituted $C_{1-6}$ alkyl group, an optionally substituted $C_{2-6}$ alkenyl group, or an optionally substituted amino group; and $E^3$ represents a hydrogen atom, an optionally substituted $C_{1-6}$ alkyl group, or an optionally substituted $C_{2-6}$ alkenyl group.

In this context, examples of substituents for the optionally substituted hydroxy group represented by $E^1$ and $E^2$ include a $C_{1-6}$ alkyl group, a $C_{2-6}$ alkenyl group, a $C_{2-6}$ alkynyl group, a $C_{1-6}$ alkyl-carbonyl group, a $C_{1-6}$ alkylsulfonyl group, a $C_{6-14}$ aryloxy-carbonyl group, a $C_{6-14}$ aryl-carbonyl group, and a $C_{6-14}$ arylsulfonyl group. These substituents may each be further substituted by 1 to 3 substituents selected from a halogen atom, an amino group, a mono-$C_{1-6}$ alkylamino group, and a di-$C_{1-6}$ alkylamino group. These substituents in the hydroxy group may be protective groups. If each substituent described above is capable of functioning as a protective group in itself, this substituent may be used as a protective group. Examples of such protective groups can include the same protective groups as those exemplified above as the protective group for a hydroxy group represented by $T^1$.

Examples of substituents for the optionally substituted $C_{1-6}$ alkyl group and the optionally substituted $C_{2-6}$ alkenyl group represented by $E^1$ and $E^2$ include 1 to 3 substituents selected from a halogen atom, a $C_{1-6}$ alkoxy group, a $C_{1-6}$ alkyl-carbonyl group, a $C_{1-6}$ alkylthio group, a $C_{1-6}$ alkylsulfonyl group, a $C_{6-14}$ aryloxy-carbonyl group, a $C_{6-14}$ aryl-carbonyl group, a $C_{6-14}$ arylsulfonyl group, amino group, a mono-$C_{1-6}$ alkylamino group, a di-$C_{1-6}$ alkylamino group, a nitro group, a hydroxyl group, a cyano group, and a carboxyl group. Of these substituents, the $C_{1-6}$ alkoxy group, the $C_{1-6}$ alkyl-carbonyl group, the $C_{1-6}$ alkylthio group, the $C_{1-6}$ alkylsulfonyl group, the $C_{6-14}$ aryloxy-carbonyl group, the $C_{6-14}$ aryl-carbonyl group, and the $C_{6-14}$ arylsulfonyl group may each be further substituted by 1 to 3 substituents selected from a halogen atom, an amino group, a mono-$C_{1-6}$ alkylamino group, and a di-$C_{1-6}$ alkylamino group.

Examples of substituents for the optionally substituted amino group represented by $E^1$ and $E^2$ include 1 or 2 substituents selected from a $C_{1-6}$ alkyl group, a $C_{2-6}$ alkenyl group, a $C_{2-6}$ alkynyl group, a $C_{1-6}$ alkyl-carbonyl group, a $C_{1-6}$ alkylsulfonyl group, a $C_{6-14}$ aryloxy-carbonyl group, a $C_{6-14}$ aryl-carbonyl group, and a $C_{6-14}$ arylsulfonyl group. These substituents may each be further substituted by 1 to 3 substituents selected from a halogen atom, an amino group, a mono-$C_{1-6}$ alkylamino group, and a di-$C_{1-6}$ alkylamino group.

Examples of substituents for the optionally substituted $C_{1-6}$ alkyl group and the optionally substituted $C_{2-6}$ alkenyl group represented by $E^3$ can include the same substituents as those exemplified above as the substituents for the optionally substituted $C_{1-6}$ alkyl group and the optionally substituted $C_{2-6}$ alkenyl group represented by $E^1$ and $E^2$.

X in the formulas (I) and (III) is preferably an oxygen atom.

In the formulas (I) and (III), $R^1$ represents an optionally substituted $C_{1-6}$ alkyl group, an optionally substituted $C_{2-6}$ alkenyl group, or an optionally substituted amino group. Examples of substituents for the optionally substituted $C_{1-6}$ alkyl group and the optionally substituted $C_{2-6}$ alkenyl group represented by $R^1$ can include the same substituents as those exemplified above as the substituents for the optionally substituted $C_{1-6}$ alkyl group and the optionally substituted $C_{2-6}$ alkenyl group represented by $E^1$ and $E^2$. Examples of substituents for the optionally substituted amino group represented by $R^1$ can include the same substituents as those exemplified above as the substituents for the optionally substituted amino group represented by $E^1$ and $E^2$.

$R^1$ in the formulas (I) and (III) is preferably a $C_{1-6}$ alkyl group, more preferably a methyl group.

In the formulas (I) and (III), $R^2$ represents an optionally substituted hydroxy group, an optionally substituted amino group, a hydrogen atom, an optionally substituted $C_{1-6}$ alkyl group, an optionally substituted $C_{2-6}$ alkenyl group, an optionally substituted $C_{2-6}$ alkynyl group, or a halogen atom, and $R^3$ represents a hydrogen atom, as optionally substituted hydroxy group, an optionally substituted amino group, a hydrogen atom, an optionally substituted $C_{1-6}$ alkyl group, an optionally substituted $C_{2-6}$ alkenyl group, an optionally substituted $C_{2-6}$ alkynyl group, or a halogen atom. Examples of substituents for the optionally substituted hydroxy group represented by $R^2$ and $R^3$ can include the same substituents as those exemplified above as the substituents for the optionally substituted hydroxy group represented by $E^1$ and $E^2$. Examples of substituents for the optionally substituted $C_{1-6}$ alkyl group and the optionally substituted $C_{2-6}$ alkenyl group represented by $R^2$ and $R^3$ can include the same substituents as those exemplified above as the substituents for the optionally substituted $C_{1-6}$ alkyl group and the optionally substituted $C_{2-6}$ alkenyl group represented by $E^1$ and $E^2$. Examples of substituents for the optionally substituted amino group represented by $R^2$ and $R^3$ can include those exemplified above as the substituents for the optionally substituted amino group represented by $E^1$ and $E^2$.

Preferred examples of $R^2$ and $R^3$ in the formulas (I) and (III) include the case where one of $R^2$ and $R^3$ is a hydrogen atom, and the other moiety is an optionally substituted hydroxy group. More preferably, one of $R^2$ and $R^3$ is a hydrogen atom, and the other moiety is a hydroxy group optionally substituted by a $C_{6-14}$ arylcarbonyl group. Further preferably, one of $R^2$ and $R^3$ is a hydrogen atom, and the other moiety is a hydroxy group optionally substituted by benzoyl. Also, further preferably, one of $R^2$ and $R^3$ is a hydrogen atom, and the other moiety is a hydroxy group optionally substituted by tert-butyldimethylsilyl (TBS).

Alternative preferred examples of $R^2$ and $R^3$ include the case where one of $R^2$ and $R^3$ is a hydrogen atom, and the other moiety is an optionally substituted amino group (preferably, an amino group substituted by a $C_{1-6}$ alkyl-carbonyl group optionally substituted by 1 to 3 halogen atoms; more preferably a trifluoroacetylamino group).

The open circular modified nucleic acid monomer compounds of the formulas (I) and (III) of the present invention may each be in the form of a salt thereof. Examples of such salts include: inorganic acid salts such as sulfate, nitrate, perchlorate, phosphate, carbonate, bicarbonate, hydrofluoride, hydrochloride, hydrobromide, and hydroiodide; organic carboxylic acid salts such as acetate, oxalate, maleate, tartrate, fumarate, and citrate; organic sulfonic acid salts such as methanesulfonate, trifluoromethanesulfonate, ethanesulfonate, benzenesulfonate, toluenesulfonate, and camphor sulfonate; amino acid salts such as aspartate and glutamate; quaternary amine salts; alkali metal salts such as sodium salt and potassium salt; and alkaline earth metal salts such as magnesium salt and calcium salt.

2. Production of Open Circular Modified Nucleic Acid Monomer Compound

Hereinafter, methods for producing the open circular modified nucleic acid monomer compounds of the formulas (I) and (III) of the present invention will be described.

Starting materials or production intermediates for reactions given below may each be a salt. Examples of such salts include those exemplified above as the salts of the open circular modified nucleic acid monomer compounds of the formulas (I) and (III).

Products of reactions given below may each be used in the next reaction as a reaction solution or a crude product. Alternatively, each product may be isolated from the reaction mixture using separation means known per se in the art (e.g., recrystallization, distillation, and chromatography) and used in the next reaction.

The compound of the formula (I) (hereinafter also referred to as compound (I)) and the compound of the formula (III) (hereinafter, also referred to as compound (III)) can be produced, for example, by steps shown in the following reaction scheme 1:

Reaction scheme 1

[Formula 13]

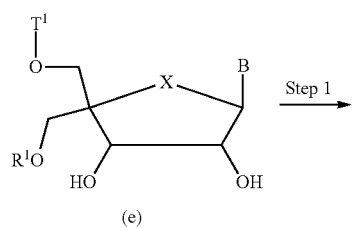

(e)

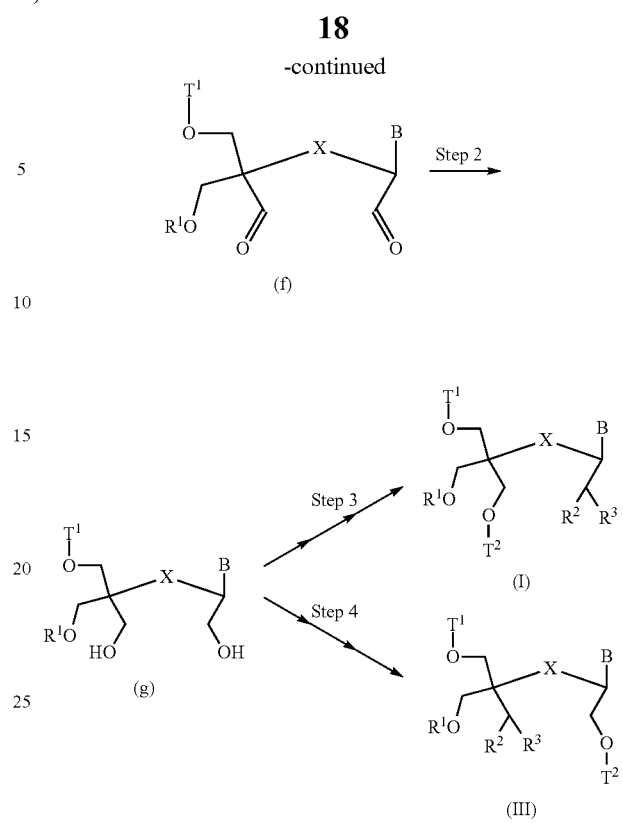

wherein B, $T^1$, $T^2$, X, $R^1$, $R^2$, and $R^3$ are as defined above.

Steps 1 and 2:

In step 1, a 1,2-diol compound represented by the formula (e) (hereinafter, referred to as compound (e)) is subjected to oxidative cleavage reaction to produce a dialdehyde compound represented by the formula (f) (hereinafter, referred to as compound (f)). In subsequent step 2, a diol compound represented by the formula (g) (hereinafter, referred to as compound (g)) is produced through reduction reaction.

In the compound (e), $T^1$ is preferably a protective group for a hydroxy group, and when X, $R^1$ and B have a reactive group such as a hydroxy group, an amino group, or a carboxy group as a substituent, these reactive groups are preferably protected with their respective protective groups described above. Compound (e) wherein X is an oxygen atom can be produced by a method described in, for example, Examples in the present specification, Compound (e) wherein X is a sulfur atom can be produced with reference to a method described in, for example, WO2003/026675 (Gosselin, G.; Imbach, J.-L.; Sammadossi, J.-P. 2003 PCT Int. Appl) or WO2003/026589 (Gosselin, G.; Imbach, J.-L.; Sammadossi, J.-P. 2003 PCT Int. Appl). Compound (e) wherein X is —C($E^1$)($E^2$)—, —C(=O)—, —C(=S)—, —C(=C($E^1$)($E^2$))—, or —C(=$NE^3$)— can be produced with reference to a method described in, for example, Kim, S.-A et al. Synlett 2007, (7) 1055-1058. Compound (e) wherein X is —N($E^3$)— can be produced with reference to a method described in, for example, Varaprasad, C. V, et al. Tetrahedron 1999, 55, 13345-13368.

The oxidative cleavage reaction in step 1 is a reaction that cleaves the carbon-carbon bond to form the corresponding dialdehyde compound. This reaction can be carried out by a periodic acid method using a periodic acid salt such as sodium periodate (Bull. Soc, Chim. France [4] 43, 683 (1928); and J. Am. Soc. Chem. Soc., 59, 2049 (1937)), a Criegee method using lead(IV) tetraacetate (Chem. Ber. 64, 260 (1931); and Tetrahedron: Asymmetry. 8. 451 (1997)), etc. The step 1 can be carried out, for example, by stirring at room temperature (1 to 30° C., hereinafter, the term "room temperature" described herein also means 1 to 30° C.) for 5 minutes to 24 hours in the presence of a periodic acid salt or lead(IV) tetraacetate in an organic solvent that does not inhibit the reaction, such as tetrahydrofuran, N,N-dimethylformamide, acetone, chloroform, dioxane, 1,4-dioxane, acetonitrile, benzene, or toluene, or in a mixed solvent of any of these organic solvents with water.

The reduction reaction in step 2 can be carried out by a method using metal hydride such as sodium borohydride ($NaBH_4$), diborane ($B_2H_6$), diisobutyl aluminum hydride (DIBAL-H), sodium cyanoborohydride ($NaBH_3CN$), or lithium triethylborohydride ($LiBH(C_2H_5)_3$), or any of other hydrides, or a complex compound thereof as a reducing agent. This method can be carried out, for example, by stirring at room temperature for 5 minutes to 24 hours in the presence of the reducing agent described above in an organic solvent that does not inhibit the reaction, such as tetrahydrofuran, diethyl ether, acetone, dichloromethane, chloroform, 1,4-dioxane, acetonitrile, benzene, or toluene.

Alternatively, in step 2, an organic compound such as 1,1,1,3,3,3-hexafluoroisopropanol may be used as a reducing agent. In this case, this organic compound reducing agent may be used in combination with the hydride reducing agent described above. A compound obtained through the reaction between the organic compound reducing agent and the hydride reducing agent can also be used as a reducing agent. For example, $NaBH(HFIP)_3$ obtained through the reaction between 1,1,1,3,3,3-hexafluoroisopropanol (HFIP) and sodium borohydride ($NaBH_4$) can be used as a reducing agent. Such a method can be carried out by stirring at room temperature or at 30 to 70° C., preferably 40 to 60° C., more preferably 45 to 55° C., further preferably 50° C., for 5 minutes to 24 hours, in the presence of the reducing agent in the organic solvent that does not inhibit the reaction. A salt such as lithium chloride may be added for this reaction. These methods are effective for the synthesis of a nucleic acid that is difficult to synthesize by a reduction method using a hydride reducing agent, and is particularly effective for the synthesis of compounds (I) and (III) wherein B is an adenine-derived group or a guanine-derived group.

The compound (g) thus obtained corresponds to compound (I) or (III) wherein $T^2$ is a hydrogen atom, one of $R^2$ and $R^3$ is a hydrogen atom, and the other moiety is a hydroxy group. The compound (g) is also the open circular modified nucleic acid monomer compound of the formula (I) or (III) of the present invention.

Steps 3 and 4:

In step 3, compound (I) having —O-$T^2$ at the 3'-position and —$R^2$ and —$R^3$ at the 2'-position is produced from the compound (g). In step 4, compound (III) having —O-$T^2$ at the 2'-position and —$R^2$ and —$R^3$ at the 3'-position is produced from the compound (g). Hereinafter, these steps 3 and 4 will be described in detail.

For example, as shown in the following reaction scheme 2:

Reaction scheme 2

[Formula 14]

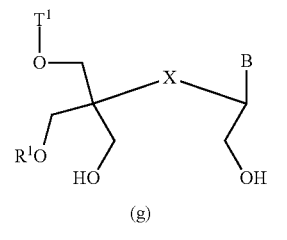

(g)

↓ Protection reaction

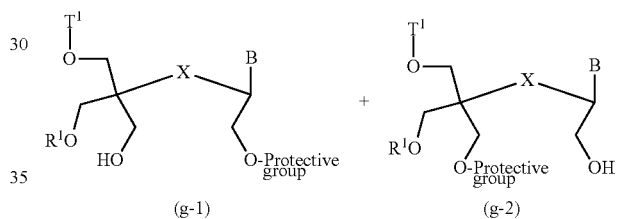

wherein X, $T^1$, B, and $R^1$ are as defined above, and examples of the protective group include those exemplified as the protective group for a hydroxy group represented by $T^1$ first, the hydroxy group of the compound (g) is subjected to ordinary protection reaction. After the ordinary protection reaction, compound (g-1) in which only —OH at the 2'-position is protected and compound (g-2) in which only —OH at the 3'-position is protected are produced by a separation and purification method such as column chromatography. A compound that can also be obtained by this separation and purification in which —OH at the 2'-position and —OH at the 3'-position are both protected corresponds to compound (I) or (III) wherein $T^2$ is a protective group for a hydroxy group, one of $R^2$ and $R^3$ is a hydrogen atom, and the other moiety is a hydroxy group substituted by a protective group, and is also the open circular modified nucleic acid monomer compound of the formula (I) or (III) of the present invention.

Subsequently, as shown in the following reaction schemes 3 and 4:

Reaction scheme 3
[Formula 15]
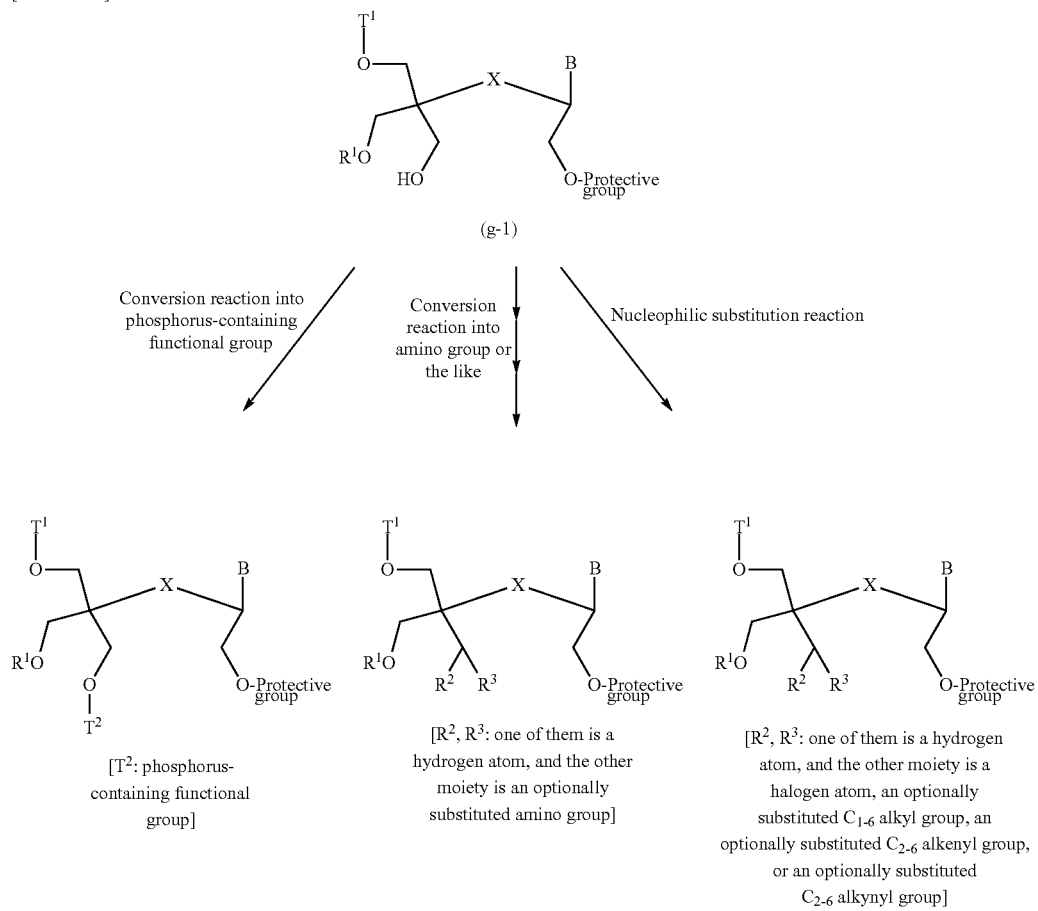
wherein X, $T^1$, $T^2$, B, $R^1$, $R^2$, and $R^3$ are as defined above, and examples of the protective group include those exemplified as the protective group for a hydroxy group represented by $T^1$
Reaction scheme 4
[Formula 16]
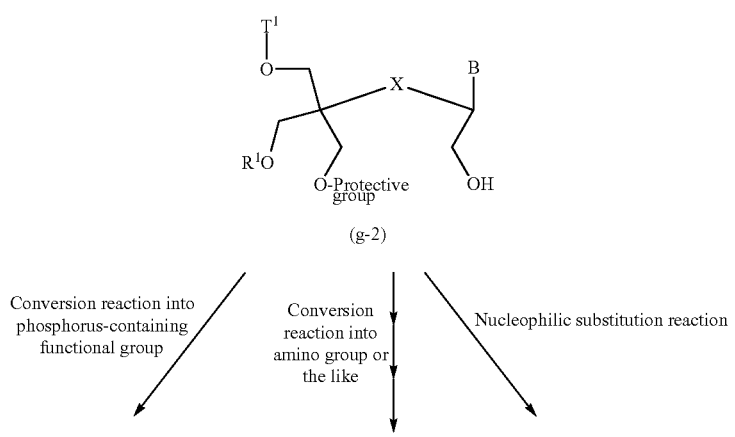

-continued

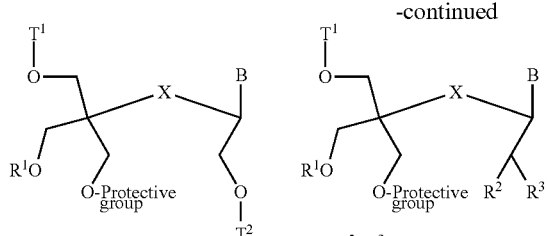

[T²: phosphorus-containing functional group]

[R², R³: one of them is a hydrogen atom, and the other moiety is an optionally substituted amino group]

[R², R³: one of them is a hydrogen atom, and the other moiety is a halogen atom, an optionally substituted $C_{1-6}$ alkyl group, an optionally substituted $C_{2-6}$ alkenyl group, or an optionally substituted $C_{2-6}$ alkynyl group]

wherein X, $T^1$, $T^2$, B, $R^1$, $R^2$, and $R^3$ are as defined above, and examples of the protective group include those exemplified as the protective group for a hydroxy group represented by $T^1$ the compound (g-1) can be subjected to, for example, a reaction that converts —OH at the 3'-position into a phosphorus-containing functional group to produce compound (I) wherein $T^2$ is a phosphorus-containing functional group. Likewise, the compound (g-2) can be subjected to a reaction that converts —OH at the 2'-position into a phosphorus-containing functional group to produce compound (III) wherein $T^2$ is a phosphorus-containing functional group.

In the conversion reaction into a phosphorus-containing functional group, conversion into the phosphorus-containing functional group of the formula (a), (b), or (c) as the phosphorus-containing functional group represented by $T^2$ can be performed, for example, by the reaction of its corresponding phosphorylating reagent represented by the following formula (a'), (b'), or (c'):

[Formula 17]

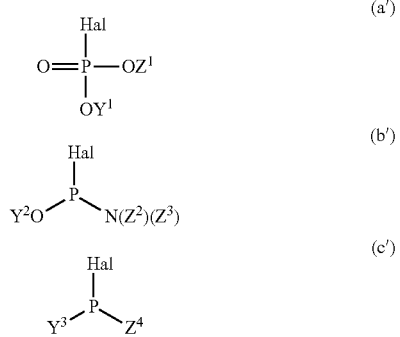

wherein Hal represents a halogen atom, and $Y^1$, $Z^1$, $Y^2$, $Z^2$, $Z^3$, $Y^3$, and $Z^4$ are as defined above with the compound (g-1) or the compound (g-2). These reactions can be carried out, for example, by dissolution in a solvent that does not inhibit the reaction, such as tetrahydrofuran, N,N-dimethylformamide, acetone, chloroform, dioxane, 1,4-dioxane, acetonitrile, benzene, or toluene, and stirring at room temperature for 5 minutes to 24 hours, if necessary, in the presence of, for example, triethylamine, tributylamine, collidine, or 2,6-lutidine.

Conversion into the phosphorus-containing functional group of the formula (d) as the phosphorus-containing functional group represented by $T^2$ can be performed by the reaction of the compound (g-1) or the compound (g-2) with a salt such as triethylammonium salt of p-toluyl-H-phosphonate at a low temperature in the presence of an accelerator such as pivaloyl chloride in pyridine. Alternatively, this conversion can be performed by the phosphitylation of the compound (g-1) or the compound (g-2) through its reaction with a phosphitylating agent such as di(t-butyl) N,N-diethylphosphoramidite, di(tribenzylmethyl) N,N-diethylphosphoramidite, or di(2-trimethylsilyl-1,1-dimethylethyl) N,N-diethylphosphoramidite and subsequent treatment with triethylamine, tributylamine, or the like.

As shown above in the reaction schemes 3 and 4, the compound (g-1) can be subjected to, for example, the conversion reaction of —OH at the 3'-position into an amino group or the like to produce compound (III) wherein one of $R^2$ and $R^3$ is a hydrogen atom, and the other moiety is an optionally substituted amino group. Likewise, the compound (g-2) can be subjected to the conversion reaction of —OH at the 2'-position into an amino group or the like to produce compound (I) wherein one of $R^2$ and $R^3$ is a hydrogen atom, and the other moiety is an optionally substituted amino group.

In the conversion reaction into an amino group or the like, for example, —OH at the 3'-position of the compound (g-1) is first alkylsulfonylated with mesyl chloride or the like. Subsequently, the resulting compound can be azidated with sodium aside or the like and further reduced (Staudinger reduction) with triphenylphosphine or the like in an aqueous solvent to produce compound (III) wherein one of $R^2$ and $R^1$ is a hydrogen atom, and the other moiety is an amino group. The obtained compound is further reacted with an alkyl halide compound such as methyl iodide or ethyl bromide or treated with formaldehyde, alkylaldehyde, or the like, and the resulting Schiff base can be reduced using metal hydride such as sodium borohydride ($NaBH_4$), diborane ($B_2H_6$), diisobutyl aluminum hydride (DIBAL-H), sodium cyanoborohydride ($NaBH_3CN$), or lithium triethylborohydride ($LiBH(C_2H_5)_3$), or any of other hydrides, or a complex compound thereof to produce compound (III) wherein one of $R^2$ and $R^3$ is a hydrogen atom, and the other moiety is a substituted amino group. Likewise, —OH at the 2'-position of the compound (g-2) can be subjected to similar reaction to produce compound (I) wherein one of $R^2$ and $R^3$ is a hydrogen atom, and the other moiety is an amino group and compound (I) wherein one of $R^2$ and $R^3$ is a hydrogen atom, and the other moiety is a substituted amino group. The aforementioned reaction with an alkyl halide compound can be carried out, for example, by stirring at room temperature for 1 hour to 30 hours in the presence of, for example, sodium hydride, 1,8-diazabicyclo[5.4.0]undec-7-ene (DBU), triethylamine, tributylamine, pyridine, or 4-dimethylaminopyridine, in a solvent that does not inhibit the reaction, such as anhydrous methanol, anhydrous ethanol, tetrahydrofuran, N,N-dimethylformamide, acetone, dichloromethane, chloroform, dioxane, 1,4-dioxane, acetonitrile, benzene, or toluene.

As shown above in the reaction schemes 3 and 4, —OH at the 3'-position of the compound (g-1) can be subjected to nucleophilic substitution reaction with a halogenating reagent, a $C_{1-6}$ alkyl halide compound, a $C_{2-6}$ alkenyl halide compound, a $C_{2-6}$ alkynyl halide compound, or the like to produce compound (III) wherein one of $R^2$ and $R^3$ is a hydrogen atom, and the other moiety is a halogen atom, an optionally substituted $C_{1-6}$ alkyl group, an optionally substituted $C_{2-6}$ alkenyl group, or an optionally substituted $C_{2-6}$ alkenyl group. Likewise, —OH at the 2-position of the compound (g-2) can be subjected to nucleophilic substitution reaction to produce compound (I) wherein one of $R^2$ and $R^3$ is a hydrogen atom, and the other moiety is a halogen atom, an optionally substituted $C_{1-6}$ alkyl group, an optionally substituted $C_{2-6}$ alkenyl group, or an optionally substituted $C_{2-6}$ alkenyl group.

These nucleophilic substitution reactions can be carried out using a halogenating reagent (e.g., thionyl chloride or N,N-diethylaminosulfur trifluoride), a $C_{1-6}$ alkyl halide compound (e.g., methyl iodide or ethyl bromide), a $C_{2-6}$ alkenyl halide compound (e.g., ethenyl bromide or butenyl bromide), or a $C_{2-6}$ alkynyl halide compound (e.g., acetylene bromide), for example, by dissolution in a solvent that does not inhibit the reaction, such as anhydrous methanol, anhydrous ethanol, tetrahydrofuran, N,N-dimethylformamide, acetone, chloroform, dioxane, 1,4-dioxane, acetonitrile, benzene, or toluene and stirring at room temperature for 1 hour to 30 hours in the presence of for example, triethylamine, tributylamine, pyridine, or 4-dimethylaminopyridine.

The compound (I) and the compound (III) can be produced by the methods described above. Other compounds (I) and compounds (III) can also be produced by various combinations of methods similar to the methods described above according to the compound of interest to be produced and, if necessary further combinations with methods known in the art.

The compound (I) and the compound (III) can each be isolated and purified by various combinations of methods generally used, such as column chromatography separation and recrystallization, and, if necessary, further combinations with methods known in the art.

The compound (I) and the compound (III) may each be labeled with an isotope (e.g., $^3H$, $^{11}C$, $^{14}C$, $^{18}F$, $^{35}S$, or $^{125}I$) or the like. Such compounds labeled with an isotope or the like are also included in the compound (I) and the compound (III).

In the compound (I) and the compound (III), $^1H$ may be converted to $^2H(D)$. Such deuterium conversion forms in which $^1H$ is converted to $^2H(D)$ are also included in the compound (I) and the compound (III).

The compound (I) and the compound (III) may be solvates (e.g., hydrates) or may be non-solvates. All of these solvates and non-solvates are also included in the compound (I) and the compound (III).

3. Wide Range of Open Circular Modified Nucleic Acid Monomer Compounds

The present invention also provides a wider range of open circular modified nucleic acid monomer compounds and specifically provides, as a wider range of compounds including the compound of the formula (I), open circular nucleic acid monomer compounds each represented by the following formula (I'):

[Formula 18]

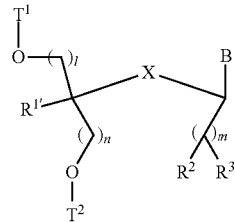

(I')

wherein
B, $T^1$, $T^2$, X, $R^2$, and $R^3$ are as defined above;
$R^{1'}$ represents —$CH_2$—X-$E^4$, —$C(F^1)(F^2)$—X-$E^4$, or —$C(=G)$-X-$E^4$,
$E^4$ represents a halogen atom, an optionally substituted hydroxy group, an optionally substituted $C_{1-6}$ alkyl group, an optionally substituted $C_{2-6}$ alkenyl group, or an optionally substituted amino group;
$F^1$ and $F^2$ each independently represent a hydrogen atom, a halogen atom, an optionally substituted hydroxy group, an optionally substituted $C_{1-6}$ alkyl group, an optionally substituted $C_{2-6}$ alkenyl group, or an optionally substituted amino group;
l represents 1 or 2;
m represents 0 or 1; and
n represents 1 or 2,
or a salt thereof. In the formula (I'), $E^4$ represents a halogen atom, an optionally substituted hydroxy group, an optionally substituted $C_{1-6}$ alkyl group, an optionally substituted $C_{2-6}$ alkenyl group, or an optionally substituted amino group. In the formula (I'), $F^1$ and $F^2$ each independently represent a hydrogen atom, a halogen atom, an optionally substituted hydroxy group, an optionally substituted $C_{1-6}$ alkyl group, an optionally substituted $C_{2-6}$ alkenyl group, or an optionally substituted amino group. Examples of substituents for the optionally substituted hydroxy group represented by $E^4$, $F^1$, and $F^2$ can include the same substituents as those exemplified above as the substituents for the optionally substituted hydroxy group represented by $E^1$ and $E^2$. Examples of substituents for the optionally substituted $C_{1-6}$ alkyl group and the optionally substituted $C_{2-6}$ alkenyl group represented by $E^4$, $F^1$ and $F^2$ can include the same substituents as those exemplified above as the substituents for the optionally substituted $C_{1-6}$ alkyl group and the optionally substituted $C_{2-6}$ alkenyl group represented by $E^1$ and $E^2$. Examples of substituents for the optionally substituted amino group represented by $E^4$, $F^1$ and $F^2$ can include the same substituents as those exemplified above as the substituents for the optionally substituted amino group represented by $E^1$ and $E^2$.

The compound of the formula (I'), as with the compound of the formula (I), has a carbon-carbon bond cleaved at the 2'- and 3'-positions and has a substituted methyl group such as a substituted hydroxymethyl group at the 4'-deposition.

This compound can be produced by the combination of methods known per se in the art from a compound generally known to those skilled in the art. Examples of the salt thereof include the same salts as those exemplified above as the salts of the open circular nucleic acid monomer compounds of the formulas (I) and (III).

4. Oligonucleic Acid Analog

The oligonucleic acid analog of the present invention is an oligonucleic acid analog containing one or more partial structures each represented by the following formula (II) or (IV):

[Formula 19]

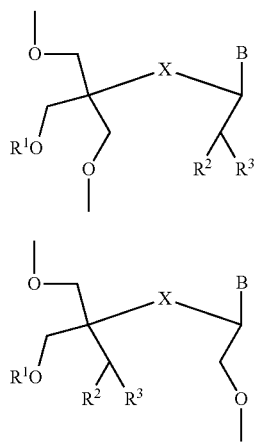

or a salt thereof, provided that when the oligonucleic acid analog or the salt thereof contains two or more of the partial structures, B, $R^1$, $R^2$, and $R^3$ may each be the same or different between or among the partial structures.

B, $R^1$, $R^2$, and $R^3$ each have the same meaning between the formula (II) or (IV) and the formula (I) or (III). The oligonucleic acid analog of the present invention is an oligonucleic acid analog containing one or more partial structures of the formula (II) or (IV) corresponding to the open circular modified nucleic acid monomer compound of the formula (I) or (III).

The oligonucleic acid analog of the present invention contains one or more partial structures of the formula (II) or (IV) and further contains nucleoside subunits other than the formula (II) or (IV).

The nucleoside subunits other than the partial structures of the formula (II) or (IV) can be any of ribonucleosides and deoxyribonucleosides. Their base moieties may be any of thymine, adenine, guanine, cytosine, and uracil or may be modified forms thereof. Examples of the modified forms of the base moieties include modified forms generally known to those skilled in the art in which a base moiety is substituted by a halogen atom, a $C_{1-6}$ alkyl group, a $C_{1-6}$ alkoxy group, a $C_{2-6}$ alkenyl group, a $C_{2-6}$ alkynyl group, a $C_{1-6}$ alkyl-carbonyl group, a $C_{1-6}$ alkylthio group, a $C_{1-6}$ alkylsulfonyl group, a $C_{6-14}$ aryloxy-carbonyl group, a $C_{6-14}$ aryl-carbonyl group, a $C_{6-14}$ arylsulfonyl group, an amino group, a mono-$C_{1-6}$ alkylamino group, a di-$C_{1-6}$ alkylamino group, a nitro group, a hydroxy group, a cyano group, a carboxy group, or the like. Also, the sugar moiety of the ribonucleoside or the deoxyribonucleoside may be a modified form of ribose or deoxyribose. Examples of the modified form of the sugar moiety can include modified forms generally known to those skilled in the art, such as 2'-amino forms (Verheyden, J. P. H. et al. J. Org. Chem. 1971, 36, 250-254; Wolfrom; Winkley M. W. J. Org. Chem. 1967, 32, 1823; Smith, L. M.; Fung, S., U.S. Pat. No. 4,849,513, 1989, and Aurup, H. et al., Nucleic Acids Res. 1994, 22, 20-24), 2'-O-methoxyethyl forms (Crook, P. D. et al. PCT Int. Appl. 1996, WO9627606), 2'-fluoro forms (Ikehara, M.; Miki, H., Chem. Pharm. Bull. 1978, 26, 2449-2453; Schmidt, S. et al, Biochim. Biophys. Acta 1992, 1130, 41-46, and Kawasaki, A. M. et al., J. Med. Chem. 1993, 36, 831-841), and 2'-O-methyl forms (Inoue, H. et al., FEBS Lett. 1987, 215, 327-330; and Inoue, H. et al., Nucleic Acids Res. 1987, 15, 6131-6148).

The number of nucleoside subunits constituting the oligonucleic acid analog of the present invention is usually preferably 4 to 100. The number of nucleoside subunits constituting, for example, DNA as the oligonucleic acid analog is preferably 4 to 100, more preferably 4 to 30. The number of nucleoside subunits constituting RNA as the oligonucleic acid analog is preferably 4 to 50, more preferably 4 to 30. The oligonucleic acid analog contains preferably 1 to 15, more preferably 1 to 10 partial structures of the formula (II) or (IV) as subunits. These partial structures may be contained at any position, and their positions can be arbitrarily determined according to the use purpose. Also, one oligonucleic acid analog may contain one or more partial structures of the formula (II) and one or more partial structures of the formula (IV).

The nucleoside subunits in the oligonucleic acid analog are bound to one another through phosphodiester bonds. Examples of the binding pattern include a naturally occurring binding pattern represented by the following formula (h) as well as various binding patterns represented by the following formulas (h1) to (h9):

[Formula 20]

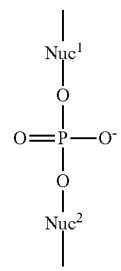

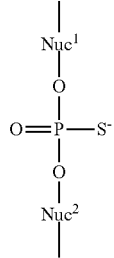

(h2)
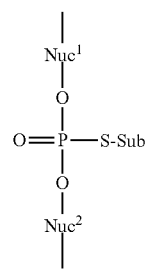

(h3)
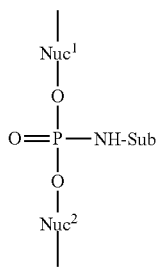

(h4)
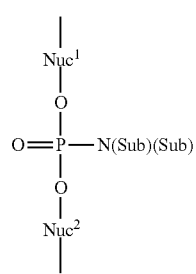

(h5)
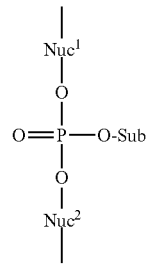

(h6)
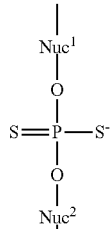

(h7)
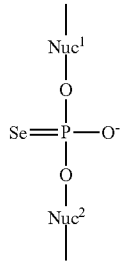

(h8)
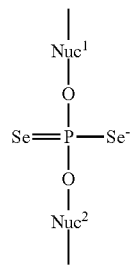

(h9)
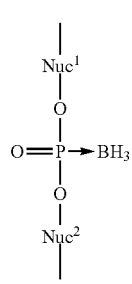

wherein $Nuc^1$ and $Nuc^2$ each represent a nucleoside subunit, Sub represents a $C_{1-6}$ alkyl group, a $C_{2-6}$ alkenyl group, a $C_{2-6}$ alkynyl group, a $C_{1-6}$ alkyl-carbonyl group, or a $C_{6-14}$ aryl-carbonyl group, and two Sub moieties in the formula (h4) may be the same or different.

Two or more of these blading patterns may be present in combination in one oligonucleic acid analog.

The oligonucleic acid analog of the present invention may be in the form of a salt thereof. Examples of such salts can include those exemplified above as the salts of the open circular modified nucleic acid monomer compounds of the formulas (I) and (III) of the present invention.

The oligonucleic acid analog of the present invention is more specifically, for example, an oligonucleic acid analog represented by the following formula (X):

[Formula 21]

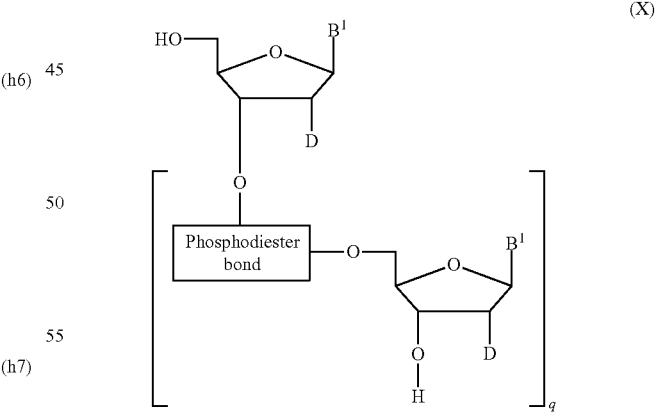

wherein the phosphodiester bond represents a binding pattern represented by any of the formulas (h) to (h9), $B^1$ represents an optionally substituted heterocyclic group. D represents a hydrogen atom, a hydroxy group, a methoxy group, a halogen atom, or an amino group, and q represents an integer of 1 or larger, provided that the phosphodiester bond, $B^1$ and D may each be the same or different between or among the constituent units, the oligonucleic acid analog containing one or more partial structures selected from the formulas (II) and (IV) instead of one or more structural units at the arbitrary positions. Examples of the optionally substituted heterocyclic group represented by $B^1$ in the formula (X) include the same as those exemplified above as the optionally substituted heterocyclic group represented by B. q is preferably an integer of 3 to 100, more preferably an integer of 4 to 40 or 50.

The oligonucleic acid analog of the present invention can be used, as described above, as, for example, siRNA, antisense RNA antisense DNA, a decoy nucleic acid, a nucleic acid aptamer, or ribozyme. The oligonucleic acid analog of the present invention can be further used as a genetic analysis tool such as an RNA probe, a DNA probe, or a molecular beacon.

Thus, the oligonucleic acid analog of the present invention may be a single-stranded oligonucleotide, a double-stranded oligonucleotide, or the like according to such usage or may be single-stranded DNA, double-stranded DNA, single-stranded RNA, double-stranded RNA a DNA/RNA chimera, or a DNA/RNA hybrid.

When the oligonucleic acid analog of the present invention is used as, for example, siRNA double-stranded RNA comprising sense and antisense strands of a target gene or their variants is preferred. The partial structure of the formula (II) or (IV) of the present invention can be contained in any one of the sense and antisense strands or their variants, or both. In this context, examples of the variants include strands containing the modified forms of the base moiety of the nucleoside described above, the modified forms of the sugar moiety, or various phosphodiester bonds other than naturally occurring ones. The siRNA may be a duplex formed by the hybridization of its sense and antisense strands so as to have a dangling end comprising approximately 2 to 5 ribonucleotides or deoxyribonucleotides at both 3' ends or modified nucleotides known in the art.

When the oligonucleic acid analog of the present invention is used as, for example, antisense RNA, antisense DNA, an RNA probe, a DNA probe, or the like, a single-stranded oligonucleotide having a sequence complementary to a target gene is preferred. When the oligonucleic acid analog of the present invention is used as a decoy nucleic acid, double-stranded DNA is preferred. When the oligonucleic acid analog of the present invention is used as a nucleic acid aptamer, ribozyme, or the like, a single-stranded oligonucleotide or a double-stranded oligonucleotide is preferred. When the oligonucleic acid analog of the present invention is used as a molecular beacon, for example, an oligonucleotide that has a stem-loop structure and has a sequence complementary to target RNA is preferred.

5. Production of Oligonucleic Acid Analog

The oligonucleic acid analog of the present invention can be produced by a solid-phase method or a liquid-phase method according to the triester method, the phosphoramidite method, the method using a dichlorophosphine derivative, the H-phosphonate method, or the like known per se in the art as a nucleic acid synthesis method using the open circular modified nucleic acid monomer compound of the formula (I) or (III). This production can also be performed using an automatic nucleic acid synthesizer. Hereinafter, these production methods will be described. For example, the oligonucleotide synthesized by solid-phase synthesis according to the most general phosphorauhdite method is excised from the solid phase and deprotected by base treatment typified by ammonia or methylamine treatment. When the oligonucleotide has a protective group (e.g., tert-butyldimethylsilyl group) that is not deprotected by the base treatment (e.g., when the oligonucleotide contains RNA), the deprotection is performed by fluorine treatment known in the art using hydrogen trifluoride/triethylamine or the like. A crude oligonucleotide product can be isolated and purified by a method known in the art, such as reverse-phase or ion-exchange chromatography. Similarly, the deprotection and the purification may be performed, if necessary, by further combinations with methods known in the art.

(1) Production of Oligonucleic Acid Analog by Triester Method

The production of the oligonucleic acid analog by the triester method can be carried out, for example, by a method represented by the following reaction scheme 5:

Reaction scheme 5

[Formula 22]

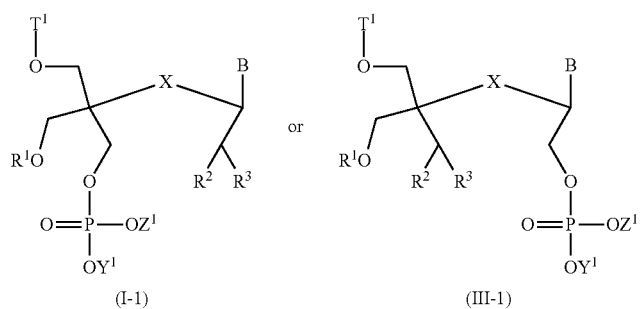

+

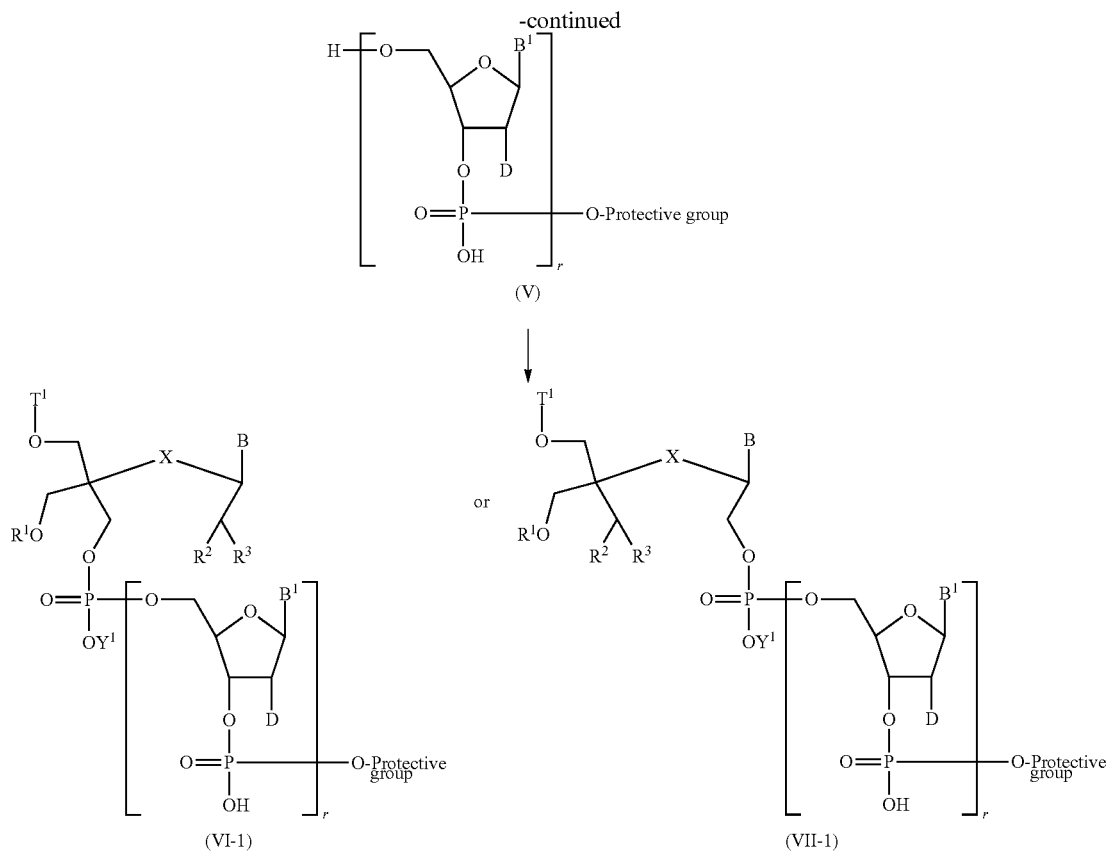

wherein $Z^1$ represents a hydrogen atom, $Y^1$ represents a protective group for the phosphoric acid, r represents an integer of 1 or larger, preferably an integer of 1 to 40 or 50, and $B^1$, D, X, $T^1$, $T^2$, B, $R^1$, $R^2$, and $R^3$ are as defined above, provided that $B^1$ and D may each be the same or different between or among the constituent units; and examples of the protective group include those exemplified as the protective group for a hydroxy group represented by $T^1$ or a method equivalent thereto. Specifically, a nucleotide unit of the formula (I-1) or (III-1) having the phosphorus-containing functional group represented by the formula (a) as $T^2$ of the compound (I) or (III) can be condensed with an oligonucleotide block of the formula (V) through reaction in the presence of a condensing agent to incorporate the partial structure of the formula (II) or (IV) as one of the subunits into the oligonucleic acid analog of the present invention. By repetitions of similar reaction, two or more partial structures of the formula (II) or (IV) can be incorporated as the subunits of the oligonucleic acid analog. The oligonucleic acid analog of the present invention of interest can be produced by repetitions of similar condensation reaction using various nucleotide units or oligonucleotide blocks and, if necessary, the addition of other methods such as the phosphoramidite method, the method using a dichlorophosphine derivative, and the H-phosphonate method described below.

The condensation reaction can be typically carried out by stirring at room temperature for 5 minutes to 24 hours in the presence of a condensing agent such as 1-(2-mesitylenesulfonyl)-3-nitro-1,2-4-triazole, 2,4,6-trimethylbenzenesulfonyltetrazole, or 1-(2,4,6-triisopropylbenzenesulfonyl)-3-nitro-1,2,4-triazole in a solvent that does not inhibit the reaction, for example, tetrahydrofuran, N,N-dimethylformamide, acetone, chloroform, dioxane, 1,4-dioxane, acetonitrile, benzene, or toluene.

If necessary, deprotection reaction can be performed in order to obtain the oligonucleic acid analog of interest after the condensation reaction or, for example, after the production of each oligonucleotide block. Deprotection reaction used in usual nucleic acid synthesis can be adopted as the deprotection reaction. The deprotection reaction can be carried out, for example, by a method using a mixed solution of an alkaline aqueous solution such as concentrated ammonia water or as aqueous sodium hydroxide solution and an organic solvent such as methanol or ethanol; a method using a solution containing an organic base such as methylamine, triethylamine, or N,N-diisopropylamine dissolved in an organic solvent such as methanol or ethanol; or a method using a solution containing tetrabutylammonium fluoride, tetrabutylammonium fluoride-acetic acid, triethylamine-hydrogen trifluoride, trifluoroacetic acid, dichloroacetic acid, trichloroacetic acid, or the like dissolved in an organic solvent such as dichloromethane or chloroform.

A commercially available product can be used as the oligonucleotide block of the formula (V). Alternatively, the oligonucleotide block of the formula (V) may be synthesized by a method known per se in the art.

(2) Production of Oligonucleic Acid Analog by Phosphoramidite Method

The production of the oligonucleic acid analog by the phosphoramidite method will be described below with reference to a typical method as an example. For example, this production can be carried out by a method represented by the following reaction scheme 6:

Reaction scheme 6
[Formula 23]
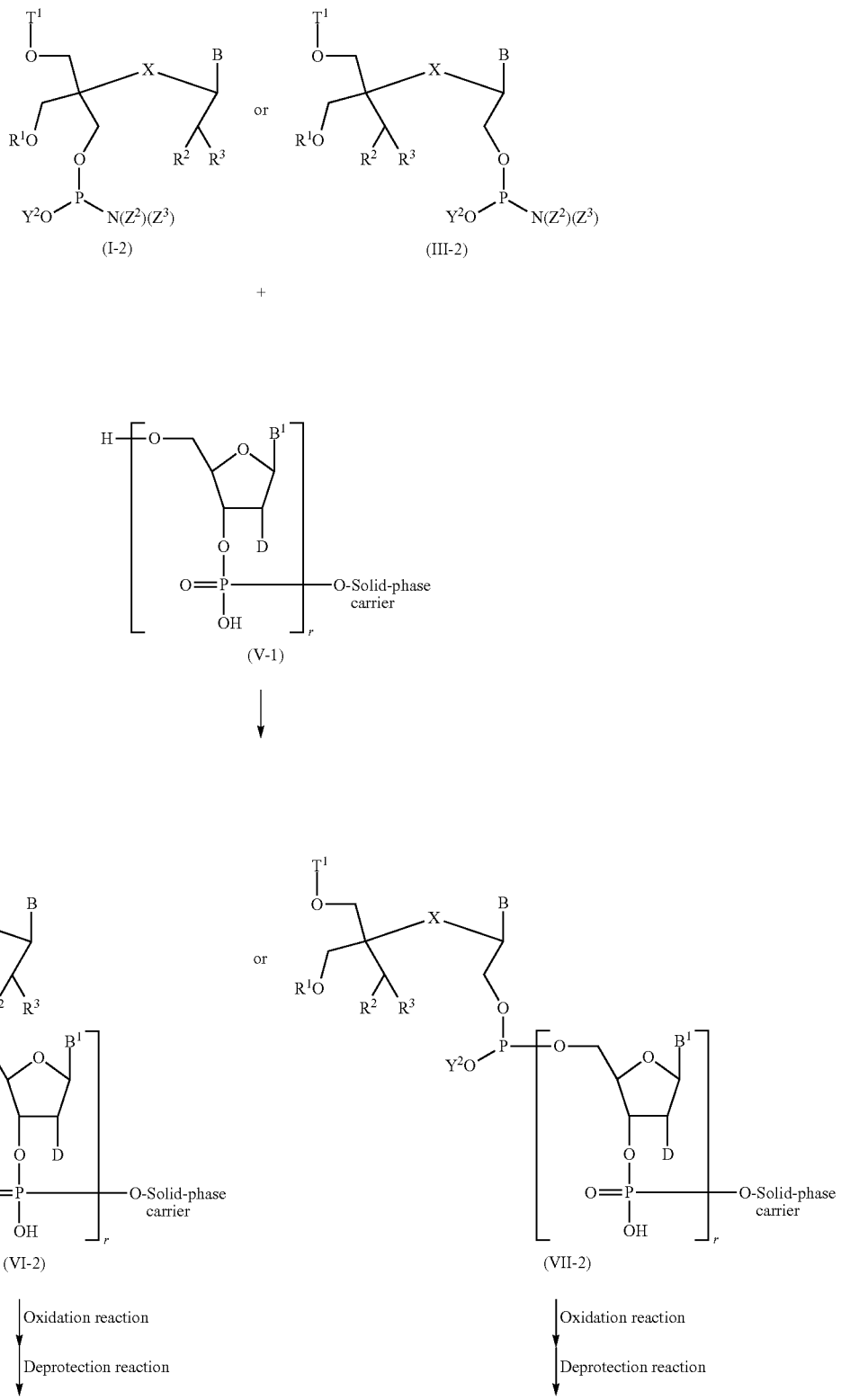

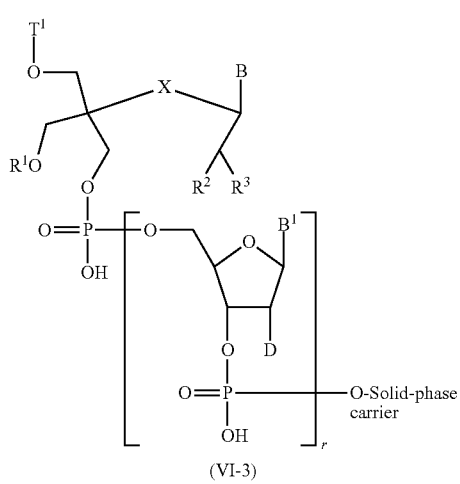
(VI-3)

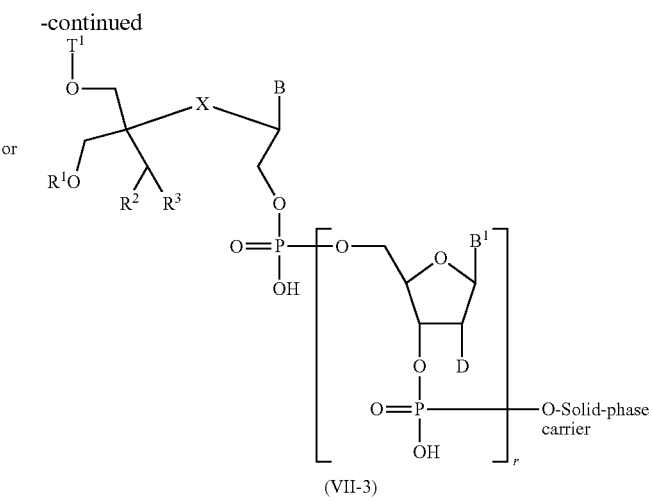
(VII-3)

wherein $Y^2$, $Z^2$, $Z^3$, $B^1$, D, r, X, $T^1$, B, $R^1$, $R^2$, and $R^3$ are as defined above or a method equivalent thereto. Specifically, a nucleotide unit of the formula (I-2) or (III-2) having the phosphorus-containing functional group represented by the formula (b) as $T^2$ of the compound (I) or (III) is bound through reaction to an oligonucleotide block of the formula (V-1) supported by a solid-phase carrier to prepare an oligonucleotide of the formula (VI-2) or (VII-2), which can then be converted to an oligonucleotide of the formula (VI-3) or (VII-3) through oxidation reaction and deprotection reaction to incorporate the partial structure of the formula (II) or (IV) as one of the subunits into the oligonucleic acid analog of the present invention. By repetitions of similar reaction, two or more partial structures of the formula (II) or (IV) can be incorporated as the subunits of the oligonucleic acid analog. The oligonucleic acid analog of the present invention of interest can be produced by repetitions of similar reaction using various nucleotide units or oligonucleotide blocks and, if necessary, the addition of other methods such as the triester method, the method using a dichlorophosphine derivative, and the H-phosphonate method.

For example, a polymer carrier such as CPG (controlled pore glass) or HCP (highly cross-linked polystyrene) is used as the solid-phase carrier to support the oligonucleotide block of the formula (V-1). Alternatively, the polymer carrier bound with a linker (e.g., a succinic acid ester linker) may be used as the solid-phase carrier. The oligonucleotide block of the formula (V-1) is supported by the solid-phase carrier by a method known per se in the art. In this context, when the oligonucleotide block of the formula (V-1) is supported by the carrier bound with the linker, the oligonucleotide block is bound to the carrier via the linker. The reaction of the nucleotide unit of the formula (I-2) or (III-2) with the oligonucleotide block of the formula (V-1) supported by the solid-phase carrier can be carried out through reaction usually used in the phosphoramidite method, for example, at 0° C. to room temperature for 10 minutes to 24 hours using a coupling reagent such as 1H-tetrazole, diisopropyl ammonium tetrazole, or 5-benzoylmercapto-1H-tetrazole in an appropriate organic solvent such as acetonitrile, dichloromethane, tetrahydrofuran, dioxane, or 1,2-dimethoxyethane. The subsequent oxidation reaction can be carried out using an oxidizing agent usually used in nucleic acid synthesis, such as halogen (e.g., iodine) alone, peroxide (e.g., t-butyl hydroperoxide or bis(trimethylsilyl) peroxide), or peroxide (e.g., m-chloroperbenzoic acid) in a single solvent such as pyridine, water, acetonitrile, tetrahydrofuran, or toluene or an arbitrary mixed solvent thereof.

Alternatively, the oligonucleic acid analog having a phosphorothioate bond in the binding pattern of the formula (h5) may be obtained by sulfuration reaction instead of the oxidation reaction. Sulfuration reaction usually used in the synthesis of modified nucleic acids having a phosphorothioate bond can be adopted as the sulfuration reaction. For example, the sulfuration reaction can be carried out using a 2,6-lutidine suspension of sulfur, a carbon disulfide solution of sulfur, tetraethylthiuram disulfide (TETD) (H. Vu et al., Tetrahedron Lett., 32, 3005-3008 (1991), a Beauge reagent (R. P. Lyer et al., J. Am. Chem. Soc., 112, 1253-254 (1990), a Lawesson's reagent, or the like.

If necessary, deprotection reaction can be performed in order to obtain the oligonucleic acid analog of interest or, for example, after the production of each oligonucleotide block. The same deprotection reaction as the deprotection reaction in the reaction scheme 5 can be adopted as the deprotection reaction. The finally produced oligonucleic acid analog can be excised from the solid-phase carrier, for example, by treatment with an alkaline aqueous solution such as concentrated ammonia water or an aqueous sodium hydroxide solution, as in the deprotection reaction.

(3) Production of Oligonucleic Acid Analog by Method Using Dichlorophosphine Derivative The production of the oligonucleic acid analog by the method using a dichlorophosphine derivative can be carried out, for example, by a method represented by the following reaction scheme 7:

Reaction scheme 7
[Formula 24]
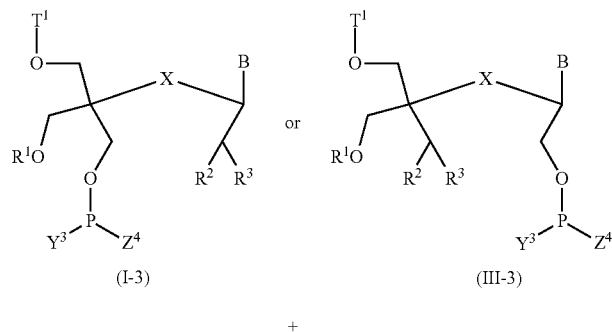
(I-3)    (III-3)
+
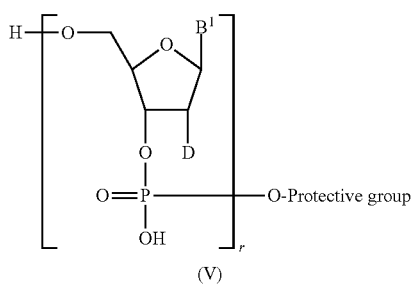
(V)
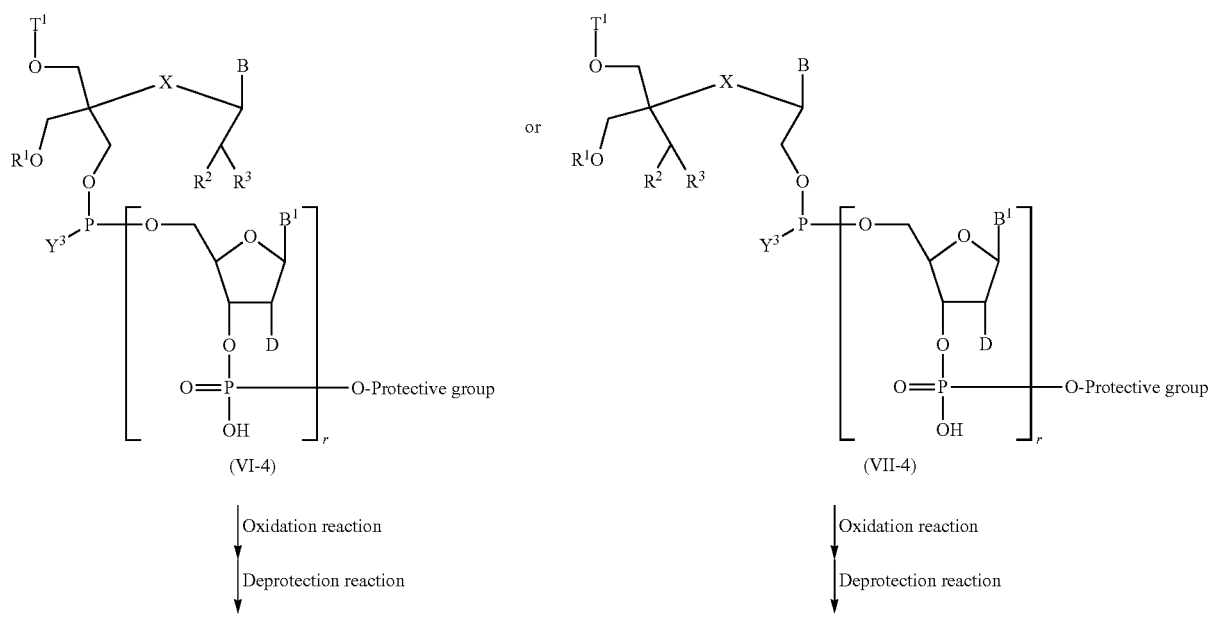
(VI-4)    (VII-4)
Oxidation reaction    Oxidation reaction
Deprotection reaction    Deprotection reaction

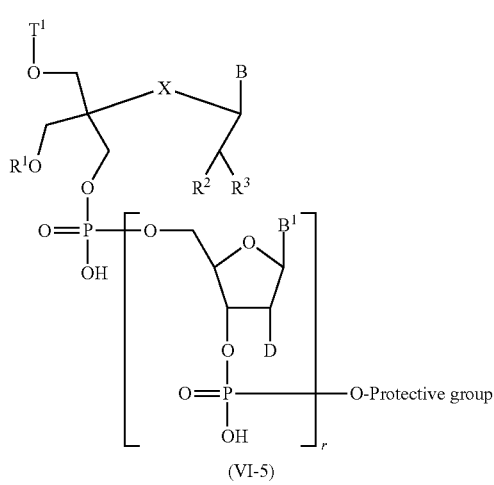
(VI-5)

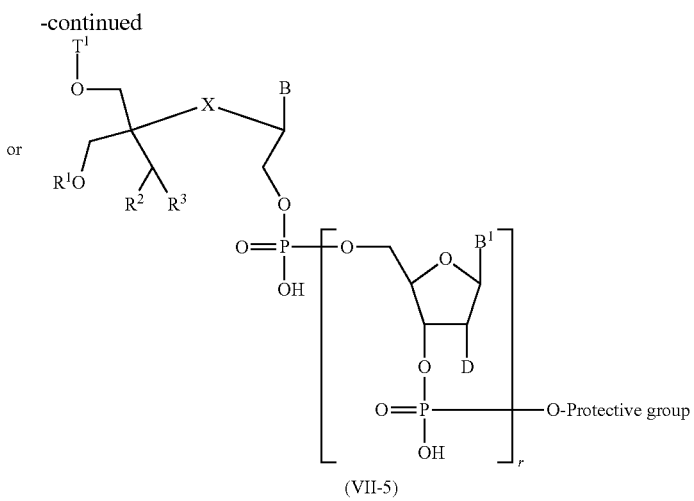
(VII-5)

wherein $Y^3$, $Z^4$, $B^1$, D, r, X, $T^1$, B, $R^1$, $R^2$, and $R^3$ are as defined above, and examples of the protective group include those exemplified as the protective group for a hydroxy group represented by $T^1$
or a method equivalent thereto. Specifically, a nucleotide unit of the formula (I-3) or (III-3) having the phosphorus-containing functional group represented by the formula (c) as $T^2$ of the compound (I) or (III) is bound to an oligonucleotide block of the formula (V) through reaction to prepare an oligonucleotide of the formula (VI-4) or (VII-4), which can then be converted to an oligonucleotide of the formula (VI-5) or (VII-5) through oxidation reaction and deprotection reaction to incorporate the partial structure of the formula (II) or (IV) as one of the subunits into the oligonucleic acid analog of the present invention. By repetitions of similar reaction, two or more partial structures of the formula (II) or (IV) can be incorporated as the subunits of the oligonucleic acid analog. The oligonucleic acid analog of the present invention of interest can be produced by repetitions of similar reaction using various nucleotide units or oligonucleotide blocks and, if necessary, the addition of other methods such as the triester method, the method using a dichlorophosphine derivative, and the H-phosphonate method.

The reaction of the nucleotide unit of the formula (I-3) or (III-3) with the oligonucleotide block of the formula (V) can be typically carried out using a reaction accelerator such as collidine or 2,6-lutidine, for example, by stirring at −78° C. to 0° C. for 5 minutes to 72 hours in a solvent that does not inhibit the reaction, such as tetrahydrofuran, N,N-dimethylformamide, acetone, chloroform, dioxane, 1,4-dioxane, acetonitrile, benzene, or toluene. The subsequent oxidation reaction and deprotection reaction can be carried out in the same way as in the phosphoramidite method described above.

Alternatively, the oligonucleic acid analog having a phosphorothioate bond in the binding pattern of the formula (h5) may be obtained by sulfuration reaction instead of the oxidation reaction, as in the phosphoramidite method.

(4) Production of Oligonucleic Acid Analog by H-Phosphonate Method

The production of the oligonucleic acid analog by the H-phosphonate method can be carried out, for example, by a method represented by the following reaction scheme 8:

Reaction scheme 8

[Formula 25]

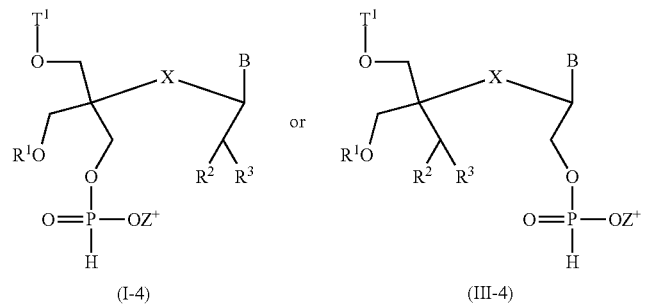

+

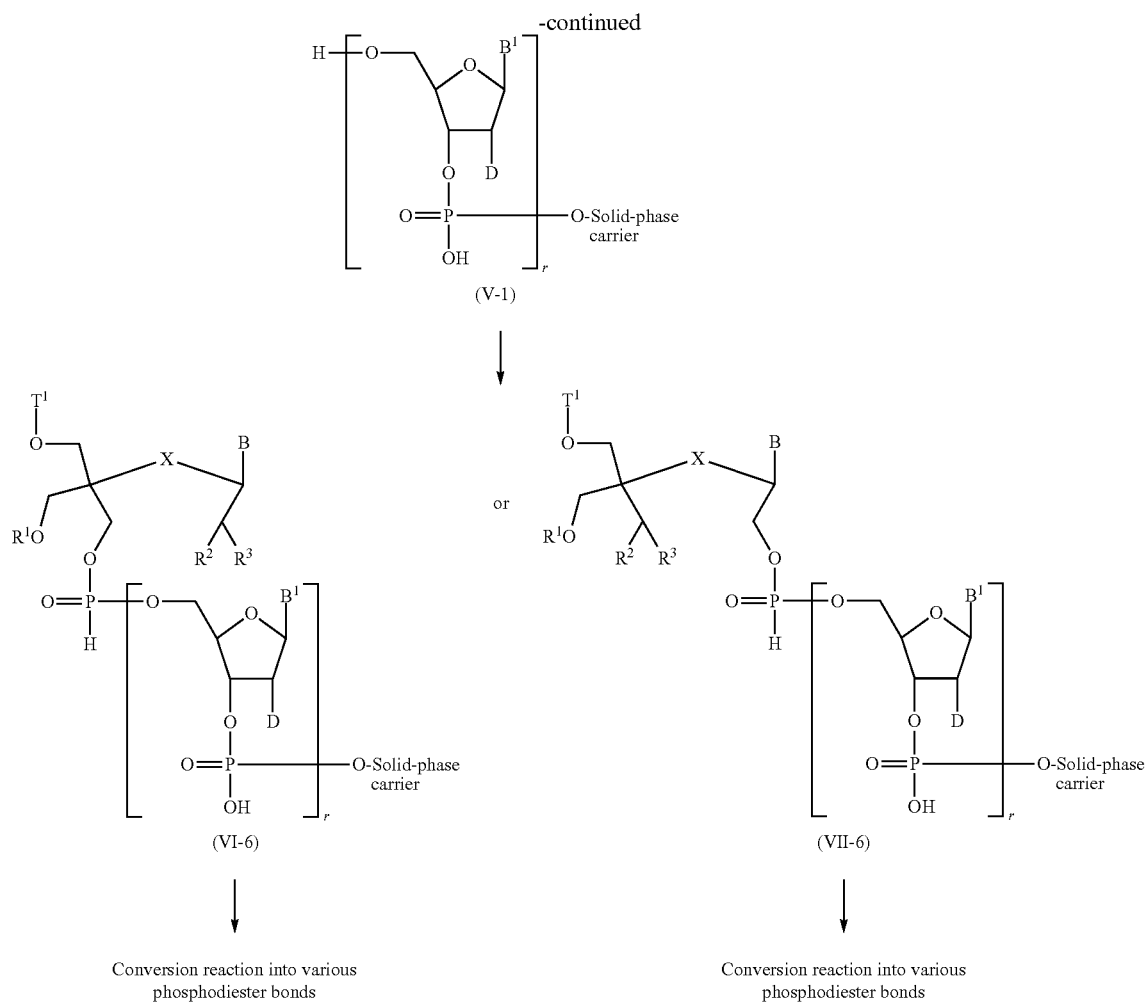

wherein $Z^+$, $B^1$, D, r, X, $T^1$, B, $R^1$, $R^2$, and $R^3$ are as defined above or a method equivalent thereto. Specifically, a nucleotide unit of the formula (I-4) or (III-4) having the phosphorus-containing functional group represented by the formula (h) as $T^2$ of the compound (I) or (III) is bound through reaction to an oligonucleotide block of the formula (V-1) supported by a solid-phase carrier in the same way as above to prepare an oligonucleotide of the formula (VI-6) or (VII-6). This reaction can be carried out by coupling reaction using a coupling reagent usually used in the H-phosphonate method, for example, pivaloyl chloride, 2-(benzoyltriazol-1-yloxy)-1,3-dimethyl-2-pyrrolidin-1-yl-1,3,2-diazaphospholidinium hexafluorate (BOMP), or N,N-bis(2-oxazolidinyl)phosphonic chloride (BopCl), at 0° C. to room temperature for 10 minutes to 24 hours in an appropriate organic solvent such as methylene chloride, tetrahydrofuran, dioxane, dimethoxyethane, N,N-dimethylformamide, acetonitrile, or pyridine.

Subsequently, the phosphorate bond in the oligonucleotide of the formula (VI-6) or (VII-6) can be converted, if necessary, to various phosphodiester bonds represented by the formulas (h) to (h9). These methods for conversion into various phosphodiester bonds can be carried out by use of reaction known per se in the art. For example, the phosphonate bond can be converted to the phosphorothioate bond of the formula (h1) through the same sulfuration reaction as above and further converted to the binding pattern of the formula (h2) through reaction with a $C_{1-6}$ alkyl halide compound, a $C_{1-6}$ alkenyl halide compound, a $C_{2-6}$ alkynyl halide compound, $C_{1-6}$ alkyl-carbonyl halide, or $C_{6-14}$ aryl-carbonyl halide. Also, the bond can be converted to the binding pattern of the formula (h3) through reaction with mono-$C_{1-6}$ alkylamine, mono-$C_{2-6}$ alkenylamine, mono-$C_{2-6}$ alkynylamine, $C_{1-6}$ alkyl-carbonylamide, or $C_{6-14}$ aryl-carbonylamide and converted to the binding pattern of the formula (h4) through reaction with di-$C_{1-6}$ alkylamine or di-$C_{2-6}$ alkenylamine. The bond can be converted to the binding pattern of the formula (h5) through reaction with $C_{1-6}$ alkyl alcohol, $C_{2-6}$ alkenyl alcohol, or the like. For a method for constructing the phosphorodithioate structure represented by the formula (h6), see the literature of Marshall et al. (Science 259: 1564-1570, 1993) or the literature of Caruthers and Nielsen (WO1989/011486). The phosphoroselenoate structure represented by the formula (h7) and the phosphorodiselenoate structure represented by the formula (h8) are also described in many literatures and generally summarized in, for example, Peyman and Ulmann, Chemical Reviews 90: 543-584 (1990); Milligan et al., J. Med. Chem., 36: 1923-1937 (1993); and the literature of Matteucci et al. (WO1992/005186). In addition, the bond can be converted to the binding pattern of the formula (h9) through reaction with borane-N,N-diisopropylethylamine, borane-pyridine, or the like.

In this way, the partial, structure of the formula (II) or (IV) cars be incorporated as one of the subunits into the oligonucleic acid analog of the present invention. By repetitions of similar reaction, two or more partial structures of the formula (II) or (IV) can be incorporated as the subunits of the oligonucleic acid analog. The oligonucleic acid analog of the present invention of interest can be produced by repetitions of similar reaction using various nucleotide units or oligonucleotide blocks and, if necessary, the addition of other methods such as the triester method, the phosphoramidite method, and the method using a dichlorophosphine derivative.

If necessary, deprotection reaction can be performed in order to obtain the oligonucleic acid analog of interest or, for example, after the production of each oligonucleotide block. The same deprotection reaction as the deprotection reaction in the reaction scheme 5 can be adopted as the deprotection reaction. The finally produced oligonucleic acid analog can be excised from the solid-phase carrier in the same way as in the reaction scheme 5.

The oligonucleic acid analog of the present invention containing one or more partial structures of the formula (II) or (IV) can be produced by the production methods described above.

The single-stranded oligonucleic acid analog thus obtained can be further prepared into a double-stranded oligonucleic acid analog. Specifically, for example, another single-stranded oligonucleic acid analog having a sequence complementary to the obtained single-stranded oligonucleic acid analog is first produced. This another single-stranded oligonucleic acid analog may be a naturally occurring oligonucleotide or may be an oligonucleotide containing one or more partial structures of the formula (II) or (IV) of the present invention. Alternatively, the single-stranded oligonucleic acid analog may be an oligonucleotide containing, as a constituent unit, a nucleoside in which the base moiety or sugar moiety of each nucleoside is a modified form thereof. For example, each of these single-stranded oligo analogs is dissolved in a usual buffer solution for annealing known to those skilled in the art, and these solutions can be mixed, heat-treated, and then cooled to produce a double-stranded oligonucleic acid analog.

The oligonucleic acid analog containing the open circular modified nucleic acid monomer compound of the present invention as at least one constituent unit is excellent in biological stability (e.g., stability in blood, more specifically, the amount of the oligonucleic acid analog remaining in serum) and suppressive activity against the expression of a target gene. Thus, the oligonucleic acid analog is expected to be useful as a "medicament for treating a disease by inhibiting the functions of a gene", including antitumor agents and antiviral agents, when used as, for example, siRNA. The oligonucleic acid analog can be used not only as siRNA but as antisense RNA, antisense DNA, a decoy nucleic acid, a nucleic acid aptamer, ribozyme, or the like. In addition, the oligonucleic acid analog can also be used a genetic analysis tool such as an RNA probe, a DNA probe, or a molecular beacon. The oligonucleic acid analog containing the open circular modified nucleic acid monomer compound of the present invention as at least one constituent unit can be supplemented with, for example, routine aids such as a buffer and/or a stabilizer to prepare a preparation for parenteral administration. Alternatively, the oligonucleic acid analog may be supplemented with routine pharmaceutical carriers to prepare a preparation for local application such as an ointment, a cream, a solution, or a plaster.

Hereinafter, the present invention will be described in more detail with reference to Examples and Reference Example. However, the present invention is not intended to be limited by these Examples.

EXAMPLES

In Examples and Reference Example, the following abbreviations or brevity codes are used.
Bn: benzyl
Me: methyl
Ac; acetyl
DMTr: 4,4'-dimethoxytrityl
Bz: benzoyl
TBDPS: teri-butyldiphenylsilyl
TBS: tert-butyldimethylsilyl
Ms: methanesulfonyl
THF: tetrahydrofuran Example 1

Synthesis of Compound Formula (I) Wherein X was Oxygen Atom, $T^1$ was Protective Group for Hydroxy Group, $R^1$ was Methyl Group, $T^2$ was Phosphoramidite Group, $R^2$ was Hydrogen Atom, $R^3$ was Benzoyloxy Group and B was Uracil The open circular modified nucleic acid monomer compound of the formula (I) of the present invention wherein X was an oxygen atom, $T^1$ was a protective group for a hydroxy group, $R^1$ was a methyl group, $T^2$ was a phosphoramidite group, $R^2$ was a hydrogen atom, $R^3$ was benzoyloxy group, and B was uracil was synthesized according to the synthesis route of Scheme 1 shown below.

Scheme 1

[Formula 26]

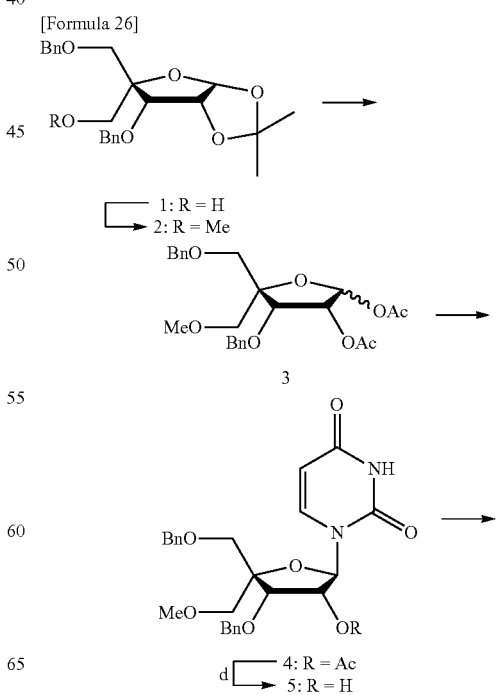

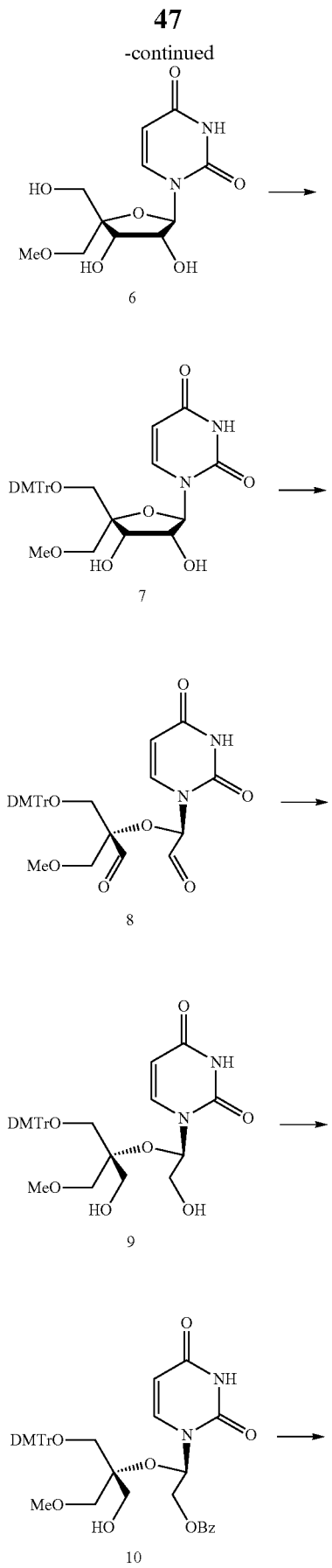

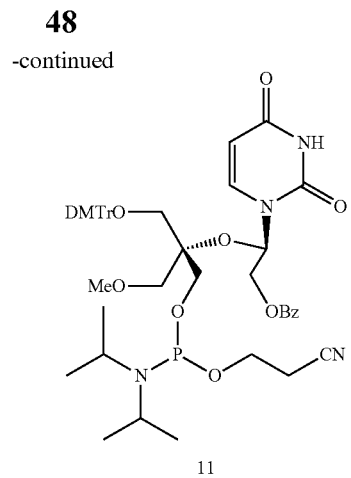

(1) Synthesis of Compound 2

Sodium hydride (60% oil mixture, 4 g) was added to a tetrahydrofuran solution (200 ml) of compound 1 (20 g), and the mixture was vigorously stirred for 20 minutes. Methane iodide (6.2 ml) was added to the reaction solution, and the mixture was stirred for 10 minutes. The reaction was stopped by the addition of ice to the reaction mixture, followed by extraction with ethyl acetate. The organic layer was washed with a saturated aqueous solution of ammonium chloride and saturated saline in this order and dried over anhydrous sodium sulfate. The desiccant was filtered off, then the filtrate was concentrated under reduced pressure, and the obtained residue was purified by silica gel column chromatography (ethyl acetate/hexane) to obtain the title compound (20 g) as a colorless oil.

$^1$H NMR (300 MHz, CDCl$_3$) δ: 1.34, 1.63 (each 3H, each s), 3.38 (3H, s), 3.52 (1H, d, J=10.4 Hz), 3.64 (2H, m), 3.91 (1H, d, J=10.8 Hz), 4.24 (1H, d, J=5.3 Hz), 4.53 (4H, m), 4.72 (1H, d, J=12.1 Hz), 5.76 (1H, d, J=3.6 Hz), 7.30 (10H, m)

(2) Synthesis of Compound 4

Acetic anhydride (25 ml) and sulfuric acid (50 µl) were added to an acetic acid solution (100 ml) of compound 2 (20 g), and the mixture was stirred at room temperature for 2.5 hours. A small amount of sodium hydroxide was added to the reaction solution, and the reaction solvent and excessive reagents were distilled off under reduced pressure. The residue was diluted with ethyl acetate, and the organic layer was washed with water, a saturated aqueous solution of sodium, bicarbonate, and saturated saline in this order and dried over anhydrous sodium sulfate. The desiccant was filtered off, then the filtrate was concentrated under reduced pressure, and the obtained crude compound 3 was subjected to azeotropy with toluene three times and then used directly in the next reaction. Uracil (8.4 g) and N,O-bis(trimethylsilyl)acetamide (37 ml) were added to an acetonitrile solution (250 ml) of the crude compound 3, and the reaction solution was heated to reflux for 30 minutes. Trimethylsilyl trifluoromethanesulfonate (10.9 ml, 60 mmol) was added to the reaction solution, and the mixture was further heated to reflux for 4 hours. The reaction was stopped by the addition of a saturated aqueous solution of sodium bicarbonate to the reaction solution, and then, the resulting reaction solution was diluted with ethyl acetate. The organic layer was washed with water, a saturated aqueous solution of sodium bicarbonate, and saturated saline in this order and dried over anhydrous sodium sulfate. The desiccant was filtered off, then the filtrate was concentrated under reduced pressure, and the obtained residue was purified by silica gel column chromatography (ethyl acetate/hexane) to obtain the title compound (24.1 g) as a white foam.

$^1$H NMR (300 MHz, CDCl$_3$) δ: 2.06 (3H, s), 3.33 (3H, s), 3.60 (3H, m), 3.84 (1H, d, J=10.2 Hz), 4.37 (1H, d, J=5.5 Hz), 4.53 (4H, m), 5.34 (2H, m), 6.28 (1H, d, J=6.4 Hz), 7.33 (10H, m), 7.71 (1H, d, J=8.1 Hz), 8.71 (1H, br s, exchangeable with D$_2$O)

(3) Synthesis of Compound 5

A 25% aqueous ammonia solution (56 ml) was added to a methanol solution (112 ml) of compound 4 (11.2 g), and the mixture was reacted at room, temperature for 4 hours. The reaction solution was concentrated under reduced pressure, and water was added to the obtained residue, followed by extraction with a mixed solvent of ethyl acetate and tetrahydrofuran. The organic layer was washed with saturated saline and derived over anhydrous magnesium, sulfate. The desiccant was filtered off then the filtrate was concentrated, under reduced pressure, and the obtained residue was suspended in ethyl acetate-hexane (2/8, v/v). The resulting solid was collected by filtration to obtain the title compound (9.8 g) as a white solid.

$^1$H NMR (300 MHz, CDCl$_3$) δ: 3.42 (3H, s), 3.48-3.70 (4H, m), 3.73-3.82 (1H, m), 4.21-4.34 (2H, m), 4.42-4.53 (2H, m), 4.59 (1H, d, J=11.4 Hz), 4.73 (1H, d, J=11.4 Hz), 5.36 (1H, d, J=8.1 Hz), 5.90 (1H, d, J=3.9 Hz), 7.20-7.42 (10H, m), 7.57 (1H, d, J=8.1 Hz), 7.95 (1H, br s)

(4) Synthesis of Compound 7

Palladium hydroxide-carbon (10 g, 20 wt %) and cyclohexene (200 ml) were added to an ethanol solution (200 ml) of compound 5 (8.0 g), and the mixture was heated to reflux for 12 hours. Insoluble matter was filtered off through celite and washed with methanol. The filtrate was concentrated under reduced pressure, and the obtained crude compound 6 was subjected to azeotropy with anhydrous pyridine twice and then used directly in the next reaction, 4,4'-Dimethoxytrityl chloride (8.7 g) was added to a pyridine solution (100 ml) of the crude compound 6, and the mixture was stirred at room temperature for 18 hours. The reaction was stopped by the addition of methanol, to the reaction solution, and then, the solvent was distilled off under reduced pressure. The residue was diluted with ethyl acetate, and the organic layer was washed with water and saturated saline in this order and then dried over anhydrous sodium sulfate. The desiccant was filtered off, then the filtrate was concentrated under reduced pressure, and the obtained residue was purified by column chromatography (ethyl acetate/hexane) to obtain the title compound (5.8 g) as a white foam.

$^1$H NMR (300 MHz, DMSO-d$_6$) δ: 3.13 (1H, d, J=9.6 Hz), 3.19 (3H, s), 3.22 (1H, m), 3.45 (1H, d, J=10.2 Hz), 3.55 (1H, d, J=10.2 Hz), 3.74 (6H, s), 4.16 (2H, m), 5.26 (1H, br d, exchangeable with D$_2$O), 5.39 (2H, m), 5.82 (1H, d, J=6.2 Hz), 6.92 (4H, d, J=8.9 Hz), 7.33 (10H, m), 11.34 (1H, br s, exchangeable with D$_2$O)

(5) Synthesis of Compound 9

Sodium periodate (2.4 g) was added to a tetrahydrofuran/water mixed solution (140 ml, 100/40 v/v) of compound 7 (5.5 g), and the mixture was vigorously stirred at room temperature for 4 hours. The reaction solution was diluted with ethyl acetate, and the organic layer was washed with water and saturated saline in this order and then dried over anhydrous sodium sulfate. The desiccant was filtered off then the filtrate was concentrated under reduced pressure, and the obtained crude compound 8 was used directly in the next reaction. The obtained crude compound 8 was dissolved in tetrahydrofuran (100 ml). Sodium tetrahydroborate (420 mg) was added to the reaction solution, and the mixture was stirred at room temperature for 45 minutes. The reaction solution was poured into ice water, followed by extraction with ethyl acetate. The organic layer was washed with saturated saline and then dried over anhydrous sodium sulfate. The desiccant was filtered off, then the filtrate was concentrated under reduced pressure, and the obtained residue was purified by column chromatography (ethyl acetate/hexane) to obtain the title compound (4.4 g) as a white foam, $^1$H NMR (300 MHz, DMSO-d$_6$) δ: 2.95 (1H, s), 3.13 (4H, m), 3.49 (6H, H), 3.74 (6H, s), 4.66, 5.11 (each 1H each br t, exchangeable with D$_2$O), 5.52 (1H, d, J=8.1 Hz), 6.07 (1H, m), 6.87 (d, 4H, J=8.9 Hz), 7.27 (9H, m), 7.50 (1H, d, J=8.1 Hz), 11.16 (1H, br s, exchangeable with D$_2$O)

(6) Synthesis of Compound 10

Triethylamine (42 μl, 0.30 mmol) and benzoyl chloride (28 μl, 0.24 mmol) were added to a tetrahydrofuran solution (2 ml) of compound 9 (120 mg, 0.20 mmol), and the mixture was stirred at room temperature for 3 hours. The reaction was stopped by the addition of ice to the reaction solution, and the resulting reaction solution was diluted with ethyl acetate. The organic layer was washed with water and saturated saline in this order and then dried over anhydrous sodium sulfate. The desiccant was filtered off, then the filtrate was concentrated under reduced pressure, and the obtained residue was purified by column chromatography (ethyl acetate/hexane) to obtain the title compound (90 mg) as a white foam.

$^1$H NMR (300 MHz, CDCl$_3$) δ: 3.26 (5H, m), 3.52 (2H, s), 3.80 (8H, m), 4.41 (2H, d, J=5.5 Hz), 5.67 (1H, d, J=8.1 Hz), 6.49 (1H, m), 6.81 (4H, m), 7.40 (13H, m), 7.94 (2H, m), 8.02 (1H, br s)

(7) Synthesis of Compound 11

3-(Bis(diisopropylamino)phosphinooxy)propanenitrile (1.23 ml) and 1H-imidazole-4,5-dicarbonitrile (0.34 g) were added to an acetonitrile solution (9.0 ml) of compound 10 (1.8 g) at room temperature, and the mixture was stirred at room temperature for 2 hours. The reaction mixture was added to a saturated aqueous solution of sodium bicarbonate, followed by extraction with ethyl acetate. The organic layer was washed with saline, dried over anhydrous magnesium sulfate, then filtered, and concentrated under reduced pressure. The obtained residue was purified by silica gel column chromatography (ethyl acetate/hexane, supplemented with 0.5% triethylamine) and silica gel column chromatography (diol silica gel, acetone/hexane, supplemented with 0.5% triethylamine). The obtained oil compound was dissolved in ethyl acetate (6.0 ml), and the solution was added drop wise to hexane (200 ml). The deposit was collected by filtration to obtain the title compound, i.e., the open circular modified nucleic acid monomer compound of the formula (I) of the present invention wherein X was an oxygen atom, T$^1$ was a protective group for a hydroxy group, R$^1$ was a methyl group, T$^2$ was a phosphoramidite group, R$^2$ was a hydrogen atom, R$^3$ was a benzoyloxy group, and B was uracil (1.18 g).

$^1$H NMR (300 MHz, CDCl$_3$) δ: 1.07-1.19 (12H, m), 2.52-2.59 (2H, m), 3.11-3.34 (5H, m), 3.43-3.60 (4H, m), 3.63-3.90 (4H, m), 3.78 (6H, s), 4.34-4.42 (2H, m), 5.66 (1H, dd, J=8.1, 2.4 Hz), 6.49-6.62 (1H, m), 6.76-6.83 (4H, m), 7.15-7.60 (13H, m), 7.90-7.98 (3H, m).

Example 2

Synthesis of Diastereomer of Compound Synthesized in Example 1

The diastereomer of the compound synthesized in Example 1 was synthesized according to the synthesis route of Scheme 2 shown below.

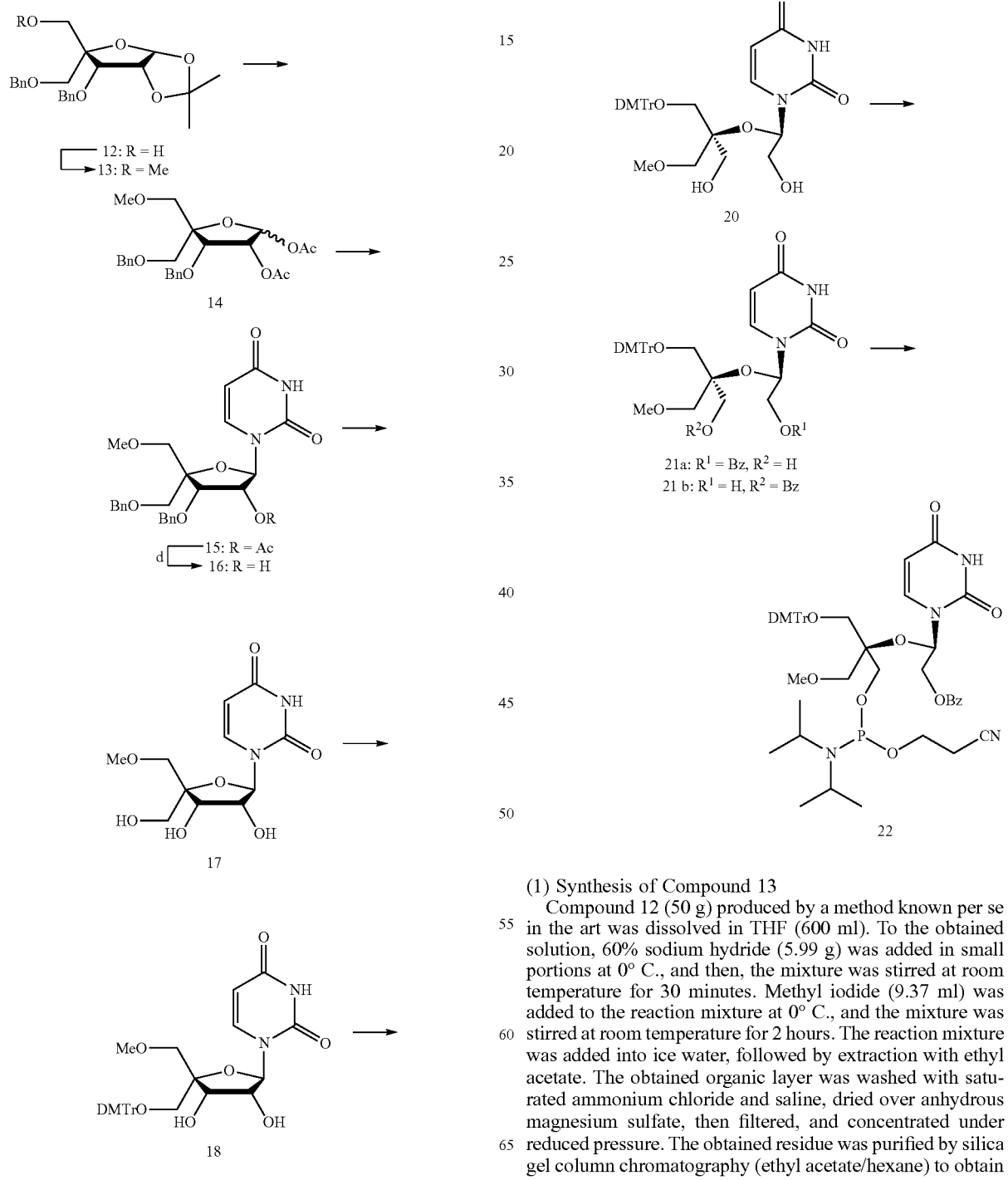

(1) Synthesis of Compound 13

Compound 12 (50 g) produced by a method known per se in the art was dissolved in THF (600 ml). To the obtained solution, 60% sodium hydride (5.99 g) was added in small portions at 0° C., and then, the mixture was stirred at room temperature for 30 minutes. Methyl iodide (9.37 ml) was added to the reaction mixture at 0° C., and the mixture was stirred at room temperature for 2 hours. The reaction mixture was added into ice water, followed by extraction with ethyl acetate. The obtained organic layer was washed with saturated ammonium chloride and saline, dried over anhydrous magnesium sulfate, then filtered, and concentrated under reduced pressure. The obtained residue was purified by silica gel column chromatography (ethyl acetate/hexane) to obtain the title compound (50.1 g).

$^1$H NMR (300 MHz, CDCl$_3$) δ: 1.32 (3H, s), 1.50 (3H, s), 3.30 (3H, s), 3.39 (1H, d, J=10.5 Hz), 3.63 (1H, d, J=10.5 Hz), 3.76 (1H, d, J=11.0 Hz), 3.98 (1H, d, J=11.0 Hz), 4.19 (1H, d, J=5.1 Hz), 4.52-4.61 (3H, m), 4.66 (1H, d, J=12.0 Hz), 4.75 (1H, d, J=12.3 Hz), 5.76 (1H, d, J=3.9 Hz), 7.20-7.38 (10H, m).

(2) Synthesis of Compound 15

Acetic anhydride (68.3 ml) and sulfuric acid (0.32 ml) were added to an acetic acid solution (200 ml) of compound 13 (50 g) at room temperature, and the mixture was stirred at room temperature for 2 hours. The reaction mixture was added to an ethyl acetate/water mixed solution, and the mixture was neutralized with sodium bicarbonate, followed by extraction with ethyl acetate. The organic layer was washed with a saturated aqueous solution of sodium bicarbonate and saline, dried over anhydrous magnesium sulfate, then filtered, and concentrated under reduced pressure. The obtained residue was purified by silica gel column chromatography (ethyl acetate/hexane) to obtain compound 14 as an oil compound (42.4 g). Uracil (0.37 g) and trimethylsilyl N-(trimethylsilyl)acetimidate (1.60 ml) were added to an acetonitrile solution (15 ml) of the obtained oil compound (1.0 g) at room temperature, and the mixture was stirred at 70° C. for 1 hour in a nitrogen atmosphere. After cooling to room temperature, trimethylsilyl trifluoromethanesulfonate (0.47 ml) was added thereto, and the mixture was stirred at 40° C. for 2 hours in a nitrogen atmosphere. The reaction mixture was cooled to room temperature and then neutralized by the addition of a saturated aqueous solution of sodium bicarbonate, followed by extraction with ethyl acetate. The organic layer was washed with water and saline, dried over anhydrous magnesium sulfate, then filtered, and concentrated under reduced pressure. The obtained residue was purified by silica gel column chromatography (ethyl acetate/hexane) to obtain the title compound (0.99 g).

$^1$H NMR (300 MHz, CDCl$_3$) δ: 2.03 (3H, s), 3.40 (3H, s), 3.56 (1H, d, 1-10.2 Hz), 3.58 (1H, d, J=10.0 Hz), 3.68 (1H, d, J=10.2 Hz), 3.71 (1H, d, J=10.0 Hz), 4.32 (1H, d, J=5.4 Hz), 4.44-4.62 (4H, m), 5.32 (1H, dd, J=6.6, 5.4 Hz), 5.73 (1H, dd, J=8.3, 2.3 Hz), 6.26 (1H, d, J=6.6 Hz), 7.23-7.39 (10H, m), 7.76 (1H, d, J=8.3 Hz), 8.08 (1H, s).

(3) Synthesis of Compound 16

A 25% aqueous ammonia solution (110 ml) was added to a methanol solution (220 ml) of compound 15 (22.1 g), and the mixture was stirred at room temperature for 4 hours. The reaction mixture was concentrated into about half of the volume under reduced pressure, followed by extraction with ethyl acetate/THF. The organic layer was washed with saline, then dried over anhydrous magnesium sulfate, filtered, and concentrated under reduced pressure. The obtained residue was purified by silica gel column chromatography (ethyl acetate/hexane) to obtain the title compound (18.6 g).

$^1$H NMR (300 MHz, CDCl$_3$) δ: 3.35 (3H, s), 3.50-3.53 (2H, m), 3.60-3.70 (2H, m), 3.87 (1H, d, J=11.4 Hz), 4.22 (1H, d, J=6.4 Hz), 4.31-4.43 (1H, m), 4.50-4.66 (3H, m), 4.73 (1H, d, J=11.4 Hz), 5.69 (1H, d, J=8.1 Hz), 5.81 (1H, d, J=3.9 Hz), 7.25-7.42 (10H, m), 7.54 (1H, d, J=8.1 Hz), 8.05 (1H, brs).

(4) Synthesis of Compound 18

Acetic acid (1.0 ml), cyclohexene (9.0 ml), and 20% by weight of palladium hydroxide/carbon (0.75 g) were added to an ethanol solution (10 ml) of compound 16 (0.5 g), and the mixture was heated to reflux overnight. After cooling to room temperature, insoluble matter was removed with celite and washed with ethanol/THF. The filtrate was concentrated under reduced pressure, md the residue was subjected to azeotropy with pyridine twice, 4,4'-(Chloro(phenyl)methylene)bis(methoxybenzene) (0.54 g) was added to a pyridine solution (7.0 ml) of the obtained crude compound 17, and the mixture was stirred overnight at room temperature. The reaction mixture was concentrated under reduced pressure, and ethyl acetate and water were added to the residue, followed by extraction with ethyl acetate. The organic layer was washed with saline, then dried over anhydrous magnesium sulfate, filtered, and concentrated under reduced pressure. The obtained residue was purified by silica gel column chromatography (ethyl acetate/hexane) to obtain the title compound (0.41 g).

$^1$H NMR (300 MHz, CDCl$_3$) δ: 3.16 (1H, brs), 3.28-3.39 (2H, m), 3.39 (3H, s), 3.41-3.56 (1H, m), 3.55 (1H, d, J=10.2 Hz), 3.63 (1H, d, J=10.0 Hz), 3.80 (6H, s): 4.32 (2H, brs), 5.75 (1H, d, J=8.4 Hz), 5.94 (1H, d, J=5.7 Hz), 6.86 (4H, d, J=8.9 Hz), 7.18-7.46 (9H, m), 7.69 (1H, d, J=8.4 Hz), 8.34 (1H, brs).

(5) Synthesis of Compound 20

Sodium periodate (0.44 g) was added to a THF/water solution (20/7.0 ml) of compound 18 (1.0 g) at room temperature, and the mixture was stirred for 4 hours. The reaction mixture was added into water, followed by extraction with ethyl acetate/THF. The organic layer was dried over anhydrous magnesium sulfate, filtered, and concentrated under reduced pressure. Sodium borohydride (77 mg) was added to a THF solution (20 ml) of the obtained crude compound 19 at room temperature, and the mixture was stirred at room temperature for 40 minutes. The reaction mixture was added into water, followed by extraction with ethyl acetate/THF. The organic layer was washed with saline, dried over anhydrous magnesium sulfate, then filtered, and concentrated under reduced pressure. The obtained residue was purified, by silica gel column chromatography (ethyl acetate/hexane) to obtain the title compound (0.44 g).

$^1$H NMR (300 MHz, DMSO-d$_6$) δ: 3.00-3.20 (2H, m), 3.14 (3H, s), 3.35-3.54 (6H, m), 3.74 (6H, s), 4.69 (1H, t, J=5.4 Hz), 5.02 (1H, t, J=5.9 Hz), 5.51 (1H, d, J=8.0 Hz), 6.04-6.11 (1H, m), 6.87 (4H, d, J=8.9 Hz), 7.17-7.41 (9H, m), 7.50 (1H, d, J=8.0 Hz), 11.14 (1H, s).

(6) Synthesis of Compound 21a and Compound 21b

Triethylamine (1.41 ml) and benzoyl chloride (0.94 ml) were added to a THF solution (60 ml) of compound 20 (4.0 g) at 0° C., and the mixture was stirred at room temperature for 2 hours. Triethylamine (1.41 ml) and benzoyl chloride (0.94 ml) were added to the reaction mixture, and the mixture was further stirred at room temperature for 4 hours. The reaction mixture was added into ice water, followed by extraction with ethyl acetate. The organic layer was washed with saline, dried over anhydrous magnesium sulfate, then filtered, and concentrated under reduced pressure. The obtained residue was purified by silica gel column chromatography (ethyl acetate/hexane) to obtain the title compounds 21a (1.16 g) and 21b (1.07 g).

Compound 21a $^1$H NMR (300 MHz, CDCl$_3$) δ: 2.16 (1H, J=6.6 Hz), 3.21-3.33 (2H, m), 3.27 (3H, s), 3.54 (1H, d, J=10.5 Hz), 3.62 (1H, d, J=10.5 Hz), 3.64-3.81 (2H, m), 3.78 (6H, s), 4.36 (2H, d, J=5.4 Hz), 5.69 (1H, d, J=8.3 Hz), 6.52 (1H, t, J=5.4 Hz), 6.82 (4H, d, J=9.0 Hz), 7.16-7.64 (13H, m), 7.81-7.99 (3H, m).

Compound 21b $^1$H NMR (300 MHz, CDCl$_3$) δ: 2.10-2.23 (1H, m), 3.21-3.38 (2H, m), 3.30 (3H, s), 3.52 (1H, d, J=10.5 Hz), 3.61-3.81 (3H, m), 3.75 (6H, s), 4.38-4.45 (21H, m), 5.82

(1H, d, J=8.3 Hz), 6.57 (1H, t, J=5.7 Hz), 6.76-6.85 (4H, m), 7.15-7.43 (9H, m), 7.55-7.65 (3H, m), 7.81-7.98 (4H, m).

(7) Synthesis of Compound 22

Compound 21a (1.05 g) was subjected to azeotropy with toluene twice. 3-(Bis(diisopropylammo)phosphinooxy)propanenitrile (0.72 ml) and 1H-imidazole-4,5-dicarbonitrile (0.20 g) were added to an acetonitrile solution (10.5 ml) of the obtained residue at room temperature, and the mixture was stirred at room temperature for 2 hours. The reaction mixture was added to a saturated aqueous solution of sodium bicarbonate, followed by extraction with ethyl acetate. The organic layer was washed with saline, dried over anhydrous magnesium sulfate, then filtered, and concentrated under reduced pressure. The obtained residue was purified by silica gel column chromatography (ethyl acetate/hexane, supplemented with 0.5% triethylamine) and silica gel column chromatography (diol silica gel, acetone/hexane, supplemented with 0.5% triethylamine). The obtained oil compound was dissolved in ethyl acetate (6.0 ml), and the solution was added dropwise to hexane (200 ml). The deposit was collected by filtration to obtain the title compound, i.e., the diastereomer of the compound synthesized in Example 1 (763 mg).

$^1$H NMR (300 MHz, CDCl$_3$) δ: 1.02-1.18 (12H, m), 2.47-2.57 (2H, m), 3.20-3.37 (5H, m), 3.44-3.87 (8H, m), 3.77 (6H, s), 4.29-4.34 (1H, m), 5.66 (1H, d, J=7.8 Hz), 6.56 (1H, t, J=5.4 Hz), 6.81 (4H, d, J=8.7 Hz), 7.15-7.32 (7H, m), 7.36-7.60 (6H, m), 7.84-8.00 (3H, m).

Reference Example 1

Synthesis of Analogous Compound of Compound of Formula (I) Wherein X was Oxygen Atom, T$^1$ was Protective Group for Hydroxy Group, R$^1$ was Tert-Butylchlorodiphenylsilyl Group, T$^2$ was Phosphoramidite Group, R$^2$ was Hydrogen Atom, R$^3$ was Benzoyloxy Group, and B was Uracil An analogous compound of the compound of the formula (I) wherein X was an oxygen atom, T$^1$ was a protective group for a hydroxy group, R$^1$ was a tert-butylchlorodiphenylsilyl group, T$^2$ was a phosphoramidite group, R$^2$ was a hydrogen atom, R$^3$ was a benzoyloxy group, and B was uracil was synthesized according to the synthesis route of Scheme 3 shown below.

Scheme 3.

[Formula 28]

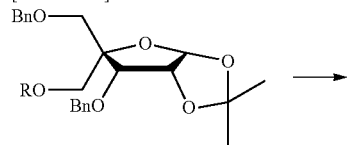

1: R = H
23: R = TBDPS

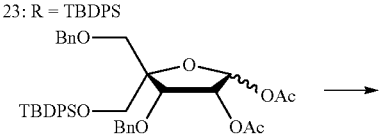

24

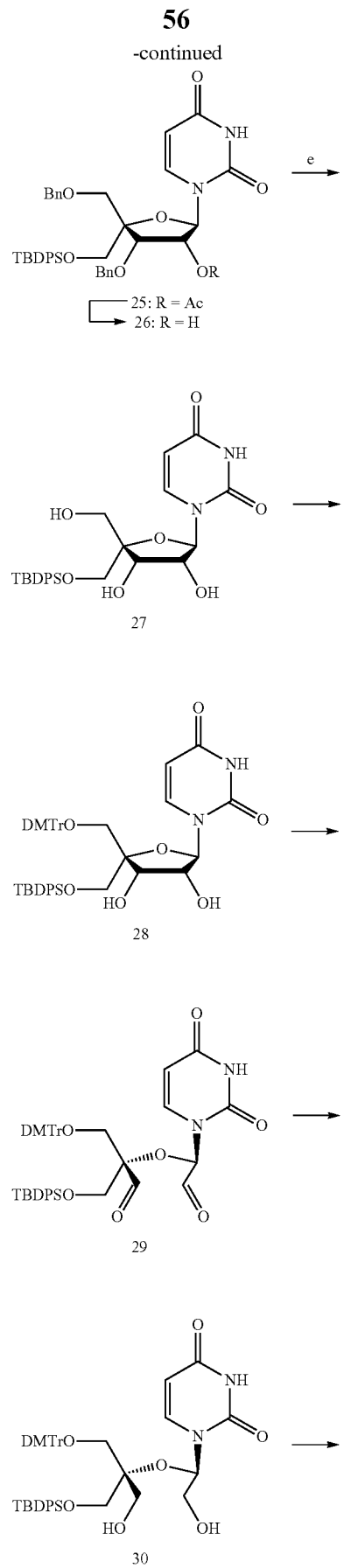

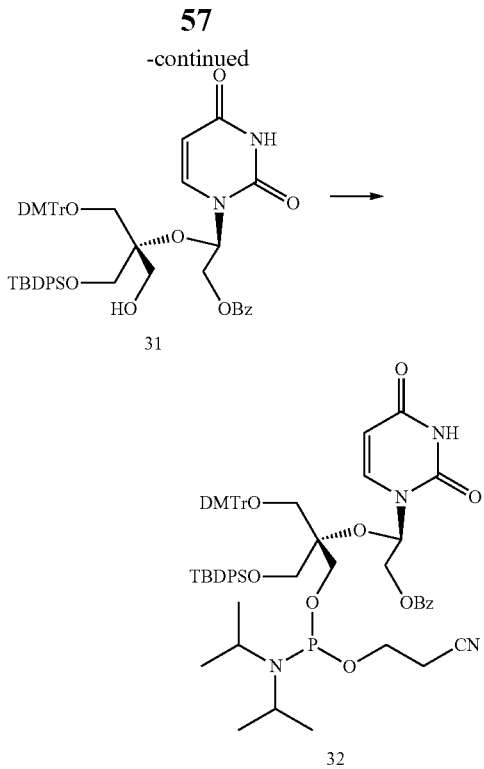

(1) Synthesis of Compound 23

Imidazole (12.8 g) and tert-butylchlorodiphenylsilane (48.7 ml) were added to an anhydrous DMF (250 ml) solution of compound 1 (50.0 g). The reaction mixture was stirred at room temperature for 3 days. Ethyl acetate was added to the reaction mixture, and the mixture was washed with an aqueous sodium bicarbonate solution and saline in this order. The solvent was distilled off under reduced pressure, and the residue was purified by silica gel column chromatography (ethyl acetate/hexane) to obtain the title compound (76.7 g).

$^1$H NMR (300 MHz, CDCl$_3$) δ: 1.03 (9H, s), 1.28 (3H, s), 1.29 (3H, s), 3.60-3.66 (1H, m), 3.70-3.76 (1H, m), 4.01-4.11 (2H, m), 4.20 (1H, d, J=5.3 Hz), 4.42-4.70 (5H, m), 5.76 (1H, d, J=3.9 Hz), 7.20-7.43 (16H, m), 7.62-7.72 (4H, m).

(2) Synthesis of Compound 24

Acetic anhydride (69.8 ml) and concentrated sulfuric acid (0.141 ml) were added to an acetic acid (277 ml) solution of compound 23 (76.7 g). The reaction mixture was stirred at room temperature for 2 hours. A 2 N aqueous sodium hydroxide solution (2 ml) was added to the reaction mixture under ice cooling, and the solvent was distilled offender reduced pressure at a hath temperature of 25° C. Ethyl acetate was added to the residue, and the mixture was washed with an aqueous sodium bicarbonate solution and saline in this order. The solvent was distilled off under reduced pressure, and the residue was purified by silica gel column chromatography (ethyl acetate/hexane) to obtain the title compound (76.1 g).

$^1$H NMR (300 MHz, CDCl$_3$) δ: 1.03 (9H, s), 1.80 (3H, s), 1.91 (3H, s), 3.64 (1H, d, J=9.8 Hz), 3.82-3.90 (2H, m), 3.95-4.00 (1H, m), 4.38-4.63 (5H, m), 5.26 (1H, d, J=4.9 Hz), 6.07 (1H, s), 7.13-7.43 (16H, m), 7.68 (4H, dd, J=11.4, 7.5 Hz).

(3) Synthesis of Compound 25

Uracil (15.0 g) and N,O-bis(trimethylsilyl)acetamide (68.1 ml) were added to an anhydrous acetonitrile (500 ml) solution of compound 24 (76.1 g). The reaction mixture was stirred at 90° C. for 1 hour in a nitrogen atmosphere. The reaction mixture was allowed to cool to 60° C., and then, trimethylsilyl trifluoromethanesulfonate (24.2 ml) was added thereto. The reaction mixture was stirred at 90° C. for 6 hours in a nitrogen atmosphere. The reaction mixture was cooled to room temperature, and ethyl acetate and hexane were added thereto. The reaction mixture was washed with an aqueous sodium bicarbonate solution. The solvent was distilled off under reduced pressure, and the residue was purified by silica gel column chromatography (ethyl acetate/hexane) to obtain the title compound (38.4 g).

$^1$H NMR (300 MHz, CDCl$_3$) δ: 1.04 (9H, s), 1.93 (3H, s), 3.64-3.81 (3H, m), 3.92 (1H, d, J=11.0 Hz), 4.35 (1H, d, J=5.5 Hz), 4.46-4.59 (4H, m), 5.27-5.36 (2H, m), 6.08 (1H, d, J=5.6 Hz), 7.17-7.47 (16H, m), 7.60 (4H, dd, J=9.5, 7.5 Hz), 7.72 (1H, d, J=8.2 Hz), 8.94 (1H, s).

(4) Synthesis of Compound 26

28% ammonia water (84.9 ml) was added to a methanol (106 ml) solution of compound 25 (10.6 g), and the mixture was stirred at room temperature for 24 hours. The solvent was distilled off under reduced pressure, and the residue was subjected to extraction with a mixture of ethyl acetate and THF. The extract was washed with saturated saline, and the solvent was distilled off under reduced pressure. The residue was purified by silica gel column chromatography (ethyl acetate/hexane) to obtain the title compound (9.97 g).

$^1$H NMR (300 MHz, CDCl$_3$) δ: 1.06 (9H, s), 3.51-3.62 (2H, m), 3.72-3.83 (3H, m), 4.25-4.48 (4H, m), 4.58-4.66 (1H, m), 4.69-4.76 (1H, m), 5.38 (1H, d, J=7.9 Hz), 5.94 (1H, d, J=4.5 Hz), 7.14-7.47 (17H, m), 7.59-7.68 (4H, m), 8.92 (1H, brs).

(5) Synthesis of Compound 27

20% palladium hydroxide (containing 50% water) (10.1 g) was added to an ethanol (288 ml) solution of compound 26 (9.97 g). The reaction mixture was stirred at room temperature for 16 hours in a hydrogen atmosphere, and then, insoluble matter was filtered off using celite. The filtrate was concentrated under reduced pressure to obtain the title compound (7.19 g).

$^1$H NMR (300 MHz, DMSO-d$_6$) δ: 0.97 (9H, s), 3.61-3.86 (4H, m), 4.09 (1H, d, J=5.3 Hz), 4.22 (1H, dd, J=7.6, 5.3 Hz), 5.71 (1H, dd, J=7.9, 2.3 Hz), 5.88 (1H, d, J=7.6 Hz), 7.36-7.49 (6H, m), 7.65-7.74 (4H, m), 7.90 (1H, d, J=8.3 Hz), 11.35 (1H, d, J=1.9 Hz).

(6) Synthesis of Compound 28

4,4'-Dimethoxytrityl chloride (4.99 g) was added to air anhydrous pyridine (94 ml) solution of compound 27 (7.19 g). The reaction mixture was stirred at room temperature for 18 hours, and then, the solvent was distilled off under reduced pressure. Ethyl acetate was added to the residue, and the mixture was washed with a 1.0% aqueous citric acid solution and an aqueous sodium bicarbonate solution in this order. The solvent was distilled off under reduced pressure, and the residue was purified by silica gel column chromatography (ethyl acetate/hexane) to obtain the title compound (8.63 g).

$^1$H NMR (300 MHz, CDCl$_3$) δ: 0.99 (9H, s), 3.18 (1H, d, J=10.2 Hz), 3.51 (1H, d, J=10.6 Hz), 3.55 (1H, d, J=4.2 Hz), 3.68 (1H, d, J=10.6 Hz), 3.77 (6H, s), 3.95 (2H, d, J=10.6 Hz), 4.42-4.50 (1H, m), 4.50-4.56 (1H, m), 5.41 (1H, d, J=8.3 Hz), 5.93 (1H, d, J=5.7 Hz), 6.76-6.84 (4H, m), 7.17-7.62 (20H, m), 8.85 (1H, brs).

(7) Synthesis of Compound 30

Water (17.5 ml) and sodium periodate (2.72 g) were added to a THF (175 ml) solution of compound 28 (8.63 g). The reaction mixture was stirred at room temperature for 24 hours and then poured to water, followed by extraction with ethyl acetate. The extract was dried over anhydrous magnesium sulfate, and the solvent was distilled off under reduced pressure. Sodium borohydride (0.481 g) was added to an aqueous THF (175 ml) solution of the obtained crude compound 29. The reaction mixture was stirred at room temperature for 16 hours and then poured to water, followed by extraction with ethyl acetate. The extract was concentrated under reduced pressure, and the residue was purified by silica gel column chromatography (ethyl acetate/hexane) to obtain the title compound (4.35 g).

$^1$H NMR (300 MHz, DMSO-d$_6$) δ: 0.86 (9H, s), 3.15 (1H, d, J=9.8 Hz), 3.28 (1H, d, J=9.8 Hz), 3.42-3.52 (2H, m), 3.62-3.76 (10H, m), 4.71 (1H, t, J=4.7 Hz), 5.03-5.09 (1H, m), 5.47 (1H, dd, J=7.9, 1.9 Hz), 6.20 (1H, t, J=5.1 Hz), 6.82 (4H, dd, J=9.1, 1.9 Hz), 7.15-7.58 (20H, m), 11.15 (1H, d, J=1.9 Hz).

(8) Synthesis of Compound 31

Benzoyl chloride (0.729 g) was added dropwise to an anhydrous THF (43.2 ml) solution of compound 30 (3.53 g) and triethylamine (0.656 g) at 0° C. The reaction mixture was stirred at 0° C. for 2 hours and at room temperature for 18 hours. The reaction mixture was poured to ice water, followed by extraction with ethyl acetate. The extract was washed with saturated saline, and the solvent was distilled off under reduced pressure. The residue was purified by silica gel column chromatography (ethyl acetate/hexane) to obtain the title compound (2.08 g).

$^1$H NMR (300 MHz, DMSO-d$_6$) δ: 0.86 (9H, s), 3.16-3.32 (2H, m), 3.61-3.81 (10H, m), 4.35 (2H, d, J=5.7 Hz), 4.88 (1H, t, J=4.5 Hz), 5.52 (1H, dd, J=8.1, 2.1 Hz), 6.64 (1H, t, J=5.5 Hz), 6.79 (4H, dd, J=9.1, 1.1 Hz), 7.16-7.69 (23H, m), 7.82-7.89 (2H, m), 11.29 (1H, d, J=1.9 Hz).

(9) Synthesis of Compound 32

2-Cyanoethyl N,N-diisopropylchlorophosphoramidite (0.386 g) was added to an anhydrous THF (15.5 ml) solution of compound 31 (1.43 g) and N,N-diisopropylethylamine (0.301 g) at −78° C. The reaction mixture was gradually heated to room temperature and stirred at room temperature for 3 hours. Ethyl acetate was added to the reaction mixture, and the mixture was washed with an aqueous sodium bicarbonate solution and saline in this order. The solvent was distilled off under reduced pressure, and the residue was purified by aminopropylsilane-bound silica gel column chromatography (ethyl acetate/hexane) to obtain the title compound, i.e., the analogous compound of the compound of the formula (I) wherein X was an oxygen atom, T$^1$ was a protective group for a hydroxy group, R$^1$ was a tert-butylchlorodiphenylsilyl group, T$^2$ was a phosphoramidite group, R$^2$ was a hydrogen atom, R$^3$ was a benzoyloxy group, and B was uracil (1.30 g).

$^1$H NMR (300 MHz, CDCl$_3$) δ: 0.97 (9H, d, J=4.3 Hz), 1.07 (6H, dd, J=6.7, 2.8 Hz), 1.14 (6H, d, J=6.7 Hz), 2.43-2.55 (2H, m), 3.28-4.38 (18H, m), 5.56 (1H, dd, J=8.1, 2.0 Hz), 6.55-6.69 (1H, m), 6.76 (4H, d, J=8.7 Hz), 7.16-7.61 (23H, m), 7.88 (2H, d, J=7.6 Hz), 7.99-8.15 (1H, m).

Example 3

Synthesis of Compound of Formula (I) Wherein X was Oxygen Atom, T$^1$ was Protective Group for Hydroxy Group, R$^1$ was Methyl Group, T$^2$ was Phosphoramidite Group, R$^2$ was Hydrogen Atom, R$^3$ was Trifluoroacetylamino Group, and B was Uracil The open circular modified nucleic acid monomer compound of the formula (I) of the present invention wherein X was an oxygen atom, T$^1$ was a protective group for a hydroxy group, R$^1$ was a methyl group, T$^2$ was a phosphoramidite group, R$^2$ was a hydrogen atom, R$^3$ was a trifluoroacetylamino group, and B was uracil was synthesized according to the synthesis route of Scheme 4 shown below.

Scheme 4

[Formula 29]

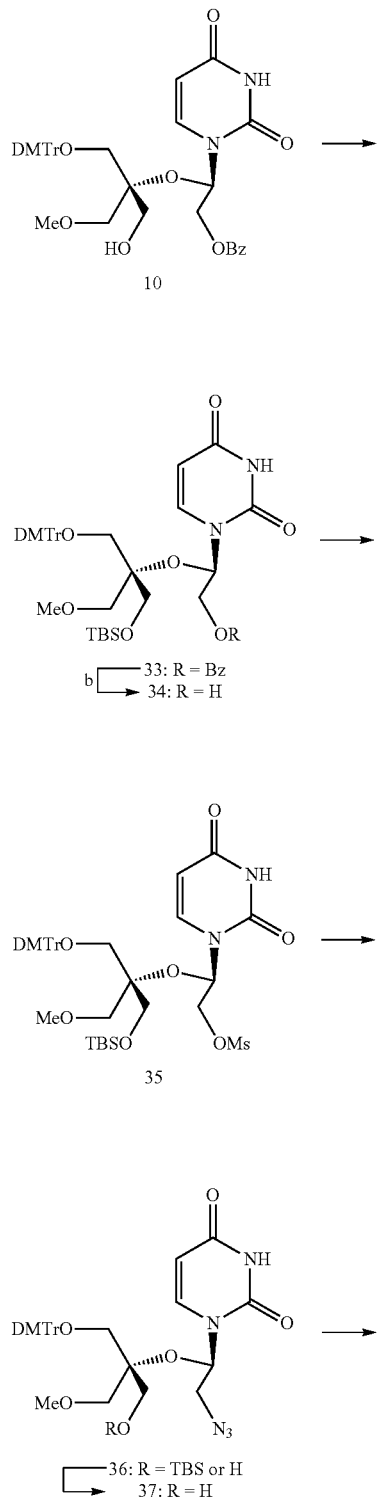

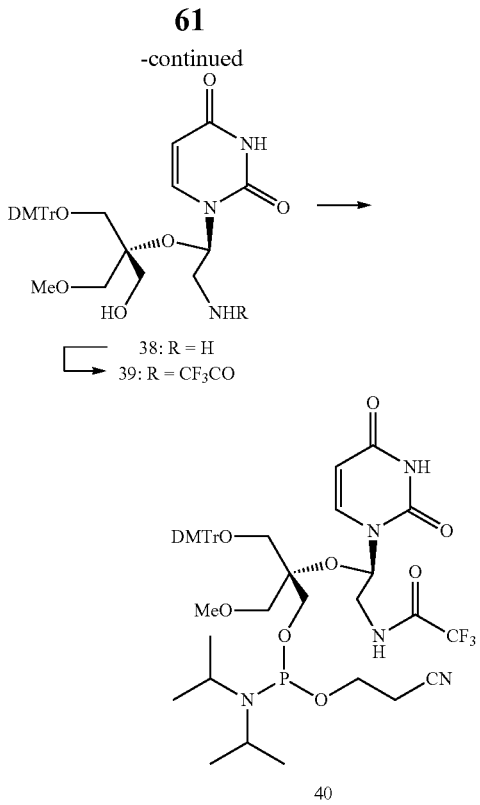

(1) Synthesis of Compound 34 tert-Butylchlorodimethylsilane (1.30 g) was added to an anhydrous pyridine (15 ml) solution of compound 10 (3.00 g). The reaction mixture was stirred at room temperature for 2 days, and then, water (3 ml) and methanol (60 ml) were added thereto. An 8 N aqueous sodium hydroxide solution (2.69 ml) was added to the reaction mixture (containing compound 33) at 0° C., and the mixture was stirred at 0° C. for 2.5 hours. A saturated aqueous solution of sodium chloride (30 ml) was added to the reaction mixture, and the mixture was stirred at room temperature for 1.0 minutes. The reaction mixture was poured to water (300 ml), followed by extraction with ethyl acetate. The extract was washed with a 10% aqueous citric acid solution (100 ml) and a saturated aqueous solution of sodium bicarbonate in this order, and the solvent was concentrated under reduced pressure. The residue was purified by silica gel column chromatography (ethyl, acetate/hexane) to obtain the title compound (3.00 g).

$^1$H NMR (300 MHz, CDCl$_3$) δ: −0.04 (3H, s), 0.00 (3H, s), 0.82 (9H, s), 2.93 (1H, dd, J=9.3, 3.2 Hz), 3.17-3.30 (5H, m), 3.40-3.55 (2H, m), 3.58-3.82 (10H, m), 5.60 (1H, d, J=7.9 Hz), 6.11 (1H, dd, J=7.2, 3.8 Hz), 6.79-6.85 (4H, m), 7.18-7.39 (9H, m), 7.49 (1H, d, J=7.9 Hz), 8.80 (1H, s).

(2) Synthesis of Compound 35

Methanesulfonyl chloride (0.65 ml) was added dropwise to an anhydrous pyridine (85 ml) solution of compound 34 (3.00 g) at 0° C. The reaction mixture was stirred at room temperature for 2 days, then anhydrous ethanol (3 ml) was added thereto, and the mixture was stirred at room temperature for 10 minutes. The solvent was concentrated under reduced pressure, and ethyl acetate was added to the residue. Insoluble matter was filtered off. The filtrate was concentrated under reduced pressure, and the residue was purified by silica gel column chromatography (ethyl acetate/hexane) to obtain the title compound (2.93 g).

$^1$H NMR (300 MHz, CDCl$_3$) δ: −0.01 (3H, s), 0.01 (3H, s), 0.83 (9H, s), 2.92 (3H, s), 3.11-3.30 (5H, m), 3.53 (2H, s), 3.72 (2H, s), 3.80 (6H, s), 4.18-4.29 (2H, m), 5.67 (1H, dd, J=7.9, 2.3 Hz), 6.42 (1H, t, J=4.3 Hz), 6.79-6.87 (4H, m), 7.18-7.41 (9H, m), 7.50 (1H, d, J=8.3 Hz), 8.46 (1H, d, J=1.5 Hz).

(3) Synthesis of Compound 37

Sodium azide (0.728 g) was added to an anhydrous DMF (37.3 ml) solution of compound 35 (2.93 g), and the mixture was stirred at 80° C. for 16 hours. The reaction mixture was cooled to room temperature. Ethyl acetate was added thereto, and the mixture was washed with saline twice. The solvent was concentrated under reduced pressure, and the residue was purified by silica gel column chromatography (ethyl acetate/hexane) to obtain compound 36 (1.03 g) and the title compound (0.39 g). 1 M tetrabutylammonium fluoride (4.22 ml) was added to a THF (14.1 ml) solution of the compound 36 (1.03 g), and the mixture was stirred at room temperature for 1.6 hours. The solvent was concentrated under reduced pressure, and the residue was purified by silica, gel column chromatography (ethyl acetate/hexane) to obtain the title compound (0.80 g).

$^1$H NMR (300 MHz, CDCl$_3$) δ: 2.28 (1H, t, J=6.2 Hz), 3.18-3.39 (6H, m), 3.51 (3H, d, J=3.0 Hz), 3.69-3.87 (8H, m), 5.67 (1H, d, J=8.3 Hz), 6.22 (1H, dd, J=5.7, 4.2 Hz), 6.80-6.88 (4H, m), 7.20-7.33 (7H, m), 7.36-7.41 (2H, m), 7.50 (1H, d, J=7.9 Hz), 8.37 (1H, brs), (4) Synthesis Compound 39

Triphenylphosphine (0.408 g) was added to an anhydrous THF (1.3.0 ml) solution of compound 37 (0.80 g), and the mixture was stirred at room temperature for 2 hours. Water (0.257 ml) was added to the reaction mixture, and the mixture was stirred at room temperature for 24 hours. The solvent was concentrated under reduced pressure, and anhydrous methanol (13.0 ml) was added to the obtained crude compound 38. 4-Dimethylaminopyridine (0.079 g) and trifluoroethyl acetate (0.462 ml) were added to the reaction mixture, and the mixture was stirred at room temperature for 2 days. The solvent was concentrated under reduced pressure, and the residue was purified by silica gel column chromatography (ethyl acetate/hexane) to obtain the title compound (0.72 g).

$^1$H NMR (300 MHz, CDCl$_3$) δ: 3.21 (3H, s), 3.24 (2H, s), 3.31 (1H, dd, J=13.4, 8.9 Hz), 3.44 (2H, s), 3.64 (1H, d, J=12.8 Hz), 3.70-3.77 (1H, m), 3.80 (6H, s), 3.85-3.91 (1H, m), 5.68 (1H, d, J=7.9 Hz), 6.17 (1H, dd, J=8.9, 3.6 Hz), 6.80-6.87 (4H, m), 7.19-7.42 (1H, m), 8.16 (1H, brs).

(5) Synthesis of Compound 40

N,N-Diisopropylethylamine (0.395 ml) was added to an anhydrous THF (15.1 ml) solution of compound 39 (1.04 g), and the mixture was cooled to −78° C. 2-Cyanoethyl N,N-diisopropylchlorophosphoramidite (0.430 g) was added to the reaction mixture, and the mixture was stirred at −78° C. for 2 hours. The reaction mixture was gradually heated to room temperature and stirred at room temperature for 2 hours. The solvent was distilled off under reduced pressure, and the residue was purified by silica gel column chromatography (ethyl acetate/hexane) and further purified by aminopropylsilane-bound silica gel column chromatography (ethyl acetate/methanol) to obtain the title compound, i.e., the open circular modified nucleic acid monomer compound of the formula (I) of the present invention wherein X was an oxygen atom, T$^1$ was a protective group for a hydroxy group, R$^1$ was a methyl group, T$^2$ was a phosphoramidite group, R$^2$ was a hydrogen atom, R$^3$ was a trifluoroacetylamino group, and B was uracil (1.02 g).

$^1$H NMR (300 MHz, DMSO-d$_6$) δ: 1.03 (6H, dd, J=6.6, 2.5 Hz), 1.11 (6H, d, J=6.8 Hz), 2.67 (2H, t, J=5.9 Hz), 3.01 (1H, dd, J=9.1, 3.0 Hz), 3.13-3.22 (4H, m), 3.35-3.72 (10H, m), 3.74 (6H, s), 5.55 (1H, dd, J=7.9, 2.6 Hz), 6.16 (1H, t, J=4.7 Hz), 6.86 (4H, d, J=8.7 Hz), 7.17-7.38 (9H, m), 7.45 (1H, dd, J=7.9, 4.2 Hz), 9.55 (1H, q, J=5.7 Hz), 11.24 (1H, s).

MS (ESI+): [M-H]$^+$ 886.3.

Example 4

Synthesis of Compound of Formula (I) Wherein X was Oxygen Atom, T$^1$ was Protective Group for Hydroxy Group, R$^1$ was Methyl Group, T$^2$ was Phosphoramidite Group, R$^2$ was Hydrogen Atom, R$^3$ was Tert-Butyldimethylsilyloxy Group, and B was Adenine The open circular modified nucleic acid monomer compound of the formula (I) of the present invention wherein X was an oxygen atom, T$^1$ was a protective group for a hydroxy group, R$^1$ was a methyl group, T$^2$ was a phosphoramidite group, R$^2$ was a hydrogen atom, R$^3$ was a tert-butyldimethylsilyloxy group, and B was adenine was synthesized according to the synthesis route of Scheme 5 shown below.

Scheme 5.

[Formula 30]

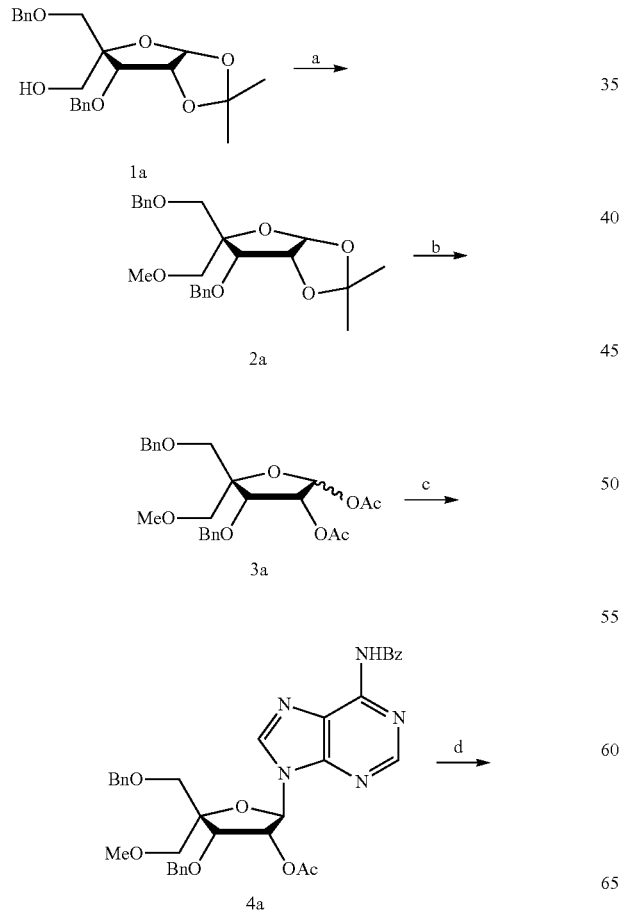

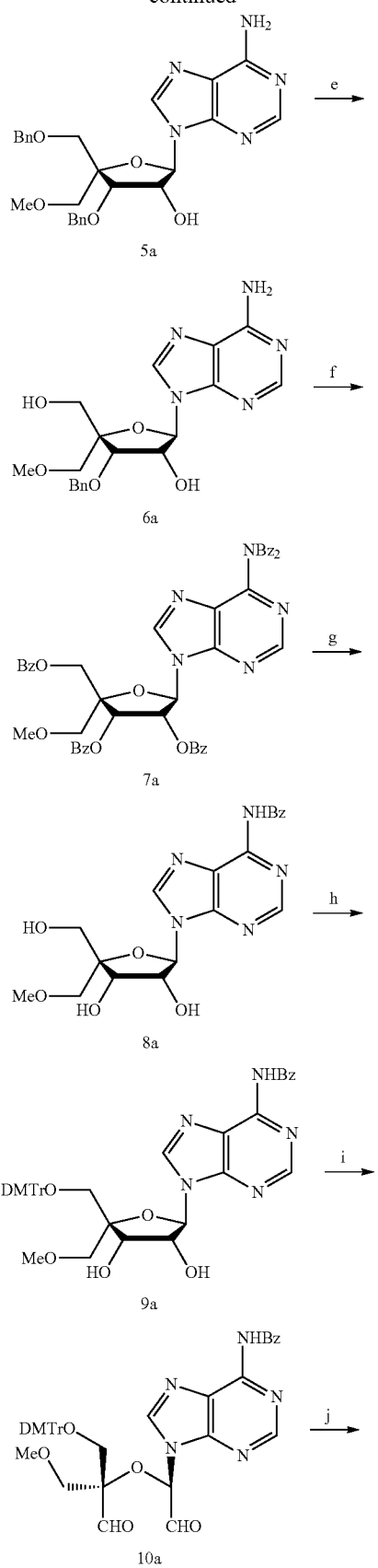

-continued

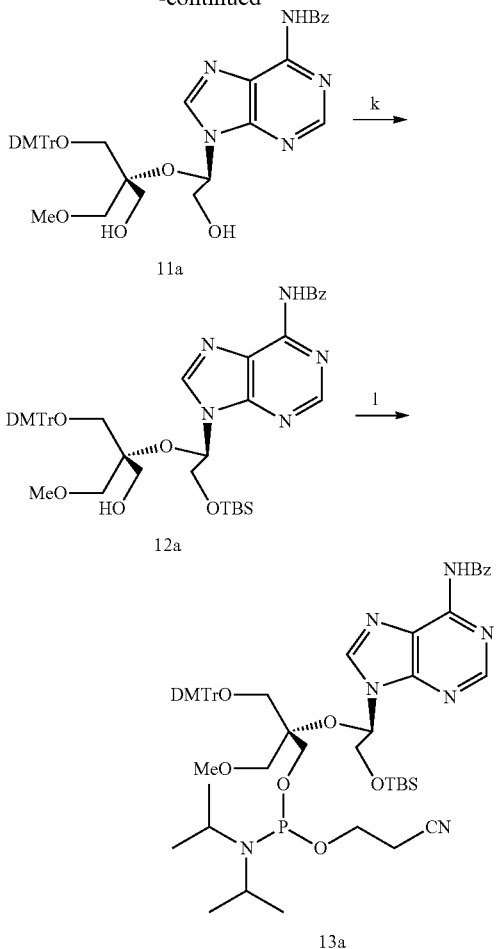

*Synthesis route of compound 13a: *reagents and conditions: a) MeI, NaH, THF, room temperature; b) Ac₂O, H₂SO₄, AcOH, room temperature; c) N⁶-benzoyladenine, BSA, TMSOTf, MeCN, reflux; d) MeNH₂, MeOH, room temperature; e) HCO₂H, Pd(OH)₂C, MeOH, room temperature; f) BzCl, pyridine, room temperature; g) NaOH, aq. THF, room temperature; h) DMTrCl, pyridine, room temperature; i) NaIO₄, aq. THF, room temperature; j) NaBH(HFIP)₃, LiCl, THF, 50° C.; k) TBSCl, pyridine, room temperature; l) (iPr₂N)₂P(OCH₂CH₂CN), 4,5-dicyanoimidazole, MeCN, room temperature Abbreviations
BSA: N,O-bis(trimethylsilyl)acetamide
HFIP: 1,1,1,3,3,3-hexafluoroisopropanol
DMTr: 4,4'-dimethoxytrityl
TBS: t-butyldimethylsilyl (1) Synthesis of Compound 2a Compound 1a (24.0 g), sodium hydride (2.9 g, 60% mineral oil mixture), and methyl iodide (4.5 ml) were mixed into tetrahydrofuran (200 ml), and the reaction solution was stirred at room temperature for 17 hours. The reaction was stopped by the addition of ice to the reaction solution, and then, the mixture was partitioned with ethyl acetate and water. The organic layer was washed with saturated saline and then dried over sodium sulfate. The desiccant was filtered off and then, the filtrate was concentrated. In order to remove the reagent-derived mineral oil, the residue was simply purified by silica gel column chromatography (hexane-ethyl acetate) to obtain crude compound 2a as an oil compound. The crude compound 2a was used in the next reaction without being further purified.

(2) Synthesis of Compound 3a

The aforementioned crude compound 2a, acetic anhydride (20 ml), and sulfuric acid (40 µl) were mixed into acetic acid (80 ml), and the reaction solution was stirred at room temperature for 2 hours. The solvent and excessive reagents were distilled off under reduced pressure, and the residue was diluted with ethyl acetate. The organic layer was washed with a saturated aqueous solution of sodium bicarbonate twice, water once, and saturated saline once, and then dried over sodium sulfate. The desiccant was filtered off, and then, the filtrate was concentrated. The residue was subjected to azeotropy with toluene twice. The obtained crude compound 3a was used in the next reaction without being further purified.

(3) Synthesis of Compound 4a

The aforementioned crude compound 3a, N⁶-benzoyladenine (16.9 g), and N,O-bis(trimethylsilyl)acetamide (34.5 ml) were mixed into acetonltrile (200 ml), and the reaction solution was refluxed for 20 minutes. Trimethylsilyl trifluoromethanesulfonate (1.6 ml) was added to the reaction solution, and the mixture was further refluxed for 2 hours. The reaction was stopped by the addition of a saturated aqueous solution of sodium bicarbonate, and then, the mixture was partitioned with ethyl acetate and a saturated aqueous solution of sodium bicarbonate. The organic layer was washed with saturated saline and then dried over sodium sulfate. The desiccant was filtered off and then, the filtrate was concentrated. The residue was purified by silica gel column chromatography (hexane-ethyl acetate) to obtain compound 4a (24 g) as a foamy compound.

$^1$H NMR (300 MHz, DMSO-$d_6$) δ 11.24 (br s, 1H, exchangeable with $D_2O$), 8.71, 8.58 (each s, each 1H), 8.04 (d, 2H, J=7.0 Hz), 7.67-7.53 (m, 3H), 7.39-7.28 (m, 10H), 6.35 (d, 1H, J=6.0 Hz), 6.11 (t, 1H, J=5.7 Hz), 4.70 (d, 1H, J=5.5 Hz), 4.64 (d, 1H, J=11.5 Hz), 4.59 (d, 1H, J=11.5 Hz), 4.53 (m, 2H), 3.70 (s, 2H), 3.65 (d, 1H, J=10.4 Hz), 3.59 (d, 1H, J=10.4 Hz), 3.28 (s, 3H), 2.02 (d, 3H).

(4) Synthesis of Compound 5a

Compound 4a (13.0 g) was dissolved in a methanol solution (120 ml) of 33% methylamine, and the reaction solution was left standing at room temperature for 15 hours. The solvent and excessive methylamine were distilled off under reduced pressure, and then, the resulting solid was collected by filtration. The filtrate was concentrated, and the obtained solid was also further collected by filtration. The solids were dried to obtain compound 5 (9.0 g) as a white solid.

$^1$H NMR (300 MHz, DMSO-$d_6$) δ 8.23, 8.12 (each s, each 1H), 7.42-7.27 (m, 10H), 5.97 (d, 1H, J=6.8 Hz), 5.62 (d, 1H, J=6.6 Hz), 5.05 (m, 1H), 4.88 (d, 1H, J=11.7 Hz), 4.50 (d, 1H, J=10.9 Hz), 4.53 (s, 2H), 4.25 (d, 1H, 1-4.9 Hz), 3.66 (br s, 2H), 3.60 (d, 1H, J=10.2 Hz), 3.55 (d, 1H, J=10.2 Hz), 3.28 (s, 1H), 3.25 (s, 3H).

(5) Synthesis of Compound 6a

Compound 5a (2.4 g), formic acid (10 ml), and 20% palladium hydroxide-carbon (50 wt %, 1.2 g) were mixed into methanol (1.00 ml), and the reaction solution was stirred at room temperature for 2 days. Insoluble matter was filtered off through celite, and the filtrate was concentrated. The residue was subjected to azeotropy with ethanol and toluene to remove the remaining formic acid. The obtained crude compound 6a was used in the next reaction without being further purified.

(6) Synthesis of Compound 7a

Crude compound 6a (1.8 g) and benzoyl chloride (5.4 ml) were dissolved in pyridine (1.00 ml) under ice cooling, and the reaction solution was stirred for 5 minutes. The reaction solution was gradually brought back to room temperature and further stirred for 18 hours. The reaction was stopped by the addition of methanol, and the solvent was distilled off under reduced pressure. The residue was diluted with ethyl acetate, and the organic layer was washed with water and saturated saline in this order. Combined aqueous layers were subjected to back extraction with ethyl acetate. All organic layers were combined and dried over sodium sulfate. The desiccant was filtered off and then, the filtrate was concentrated. The residue was purified by silica gel comma chromatography (hexane-ethyl acetate) to obtain compound 7a (4.3 g) as a foamy compound.

$^1$H NMR (300 MHz. DMSO-$d_6$) δ 8.85, 8.44 (each s, each 1H), 7.99 (m, 4H), 7.82-7.40 (m, 21H), 6.82 (d, 1H, J=5.5 Hz), 6.64 (t, 1H, J=6.0 Hz), 6.38 (d, 1H, J=6.4 Hz), 4.76 (d, 1H, J=11.7 Hz), 4.67 (d, 1H, J=11.7 Hz), 3.93 (s, 2H), 3.33 (s, 3H).

(7) Synthesis of Compound 8a

Compound 7a (4.3 g) was dissolved in a mixed solvent of tetrahydrofuran (48 ml) and methanol (16 ml). To the solution, a 1 M aqueous sodium hydroxide solution (8 ml) was added, and the reaction solution was stirred at room temperature for 30 minutes. The reaction was stopped by the addition of an aqueous citric acid solution, and the mixture was partitioned with ethyl acetate-methanol-water. The organic layer was separated, and the aqueous layer was subjected to back extraction with ethyl acetate-methanol three times and ethyl acetate-tetrahydrofuran once. All organic layers were combined and dried over sodium sulfate. The desiccant was filtered off, and then, the filtrate was concentrated. The residue was purified by silica gel column chromatography (ethyl acetate-methanol) to obtain compound 8a (2.0 g) as a foamy compound.

$^1$H NMR (300 MHz, DMSO-$d_6$) δ 11.21 (br s, 1H), 8.76, 8.71 (each s, each 1H), 8.05 (d, 2H, J=7.2 Hz), 7.65 (t, 1H, J=7.6 Hz), 7.55 (t, 2H, J=7.6 Hz), 6.05 (d, 1H, J=7.7 Hz), 5.45 (d, 1H, J=7.2 Hz), 5.25 (d, 1H, J=4.5 Hz), 5.17 (m, 1H), 4.93 (m, 1H), 4.19 (m, 1H), 3.60 (m, 1H), 3.59 (d, 1H, J=10.4 Hz), 3.26 (s, 3H), 2.76, 2.65 (each d, each 1H, J=15.1 Hz).

(8) Synthesis of Compound 9a

Compound 8a (700 mg) and 4,4'-dimethoxytrityl chloride (850 mg) were dissolved in pyridine (10 ml), and the reaction solution was stirred at room temperature for 16 hours. The reaction was stopped by the addition of ice, and the mixture was partitioned with ethyl acetate and water. The organic layer was washed with saturated saline. Combined aqueous layers were subjected to back extraction with ethyl acetate. All organic layers were combined and dried over sodium sulfate. The desiccant was filtered off, and then, the filtrate was concentrated. The residue was purified by diol silica gel column chromatography (hexane-ethyl acetate) to obtain compound 9a (690 mg) as a foamy compound.

$^1$H NMR (300 MHz, DMSO-$d_6$) δ 11.18 (brs, 1H), 8.57, 8.46 (each s, each 1H), 8.04 (d, 2H, J=7.2 Hz), 7.64 (m, 1H), 7.54 (m, 2H), 7.40 (m, 2H), 7.32-7.22 (m, 7H), 6.88 (m, 4H), 6.59 (d, 1H, J=7.4 Hz), 5.46 (d, 1H, J=7.0 Hz), 5.37 (d, 1H, J=4.9 Hz), 4.95 (m, 1H), 4.29 (m, 1H), 3.74 (d, 1H, J=10.4 Hz), 3.74 (s, 6H), 3.63 (d, 1H, J=10.4 Hz), 3.29 (d, 1H, J=9.4 Hz), 3.27 (s, 3H), 3.22 (d, 1H, J=9.4 Hz).

(9) Synthesis of Compound 10a

Compound 9a (530 mg) and sodium periodate (173 mg) were mixed in tetrahydrofuran (22.5 ml) and water (4.5 ml), and the reaction solution was stirred at room temperature for 17 hours. The reaction solution was partitioned with ethyl acetate and water, and the organic layer was washed with a saturated aqueous solution of sodium bicarbonate and saturated saline in this order. Combined aqueous layers were subjected to back extraction with ethyl acetate. All organic layers were combined and dried over sodium sulfate. The desiccant was filtered off, and then, the filtrate was concentrated. The obtained crude compound 10a was an equilibrium, mixture with aldehyde hydrate and was used in the next reaction without being further purified.

(10) Synthesis of Compound 11a

Sodium borohydride (378 mg) was suspended in tetrahydrofuran (10 ml). To the suspension, 1,1,1,3,3,3-hexafluoroisopropanol (6.2 ml) was added in an argon atmosphere, and the mixture was stirred at room temperature for 15 hours. This solution (15.8 ml) was transferred to another container. The aforementioned crude compound 10a, lithium chloride (63 mg), and tetrahydrofuran (7.4 ml) were added thereto, and the reaction solution was stirred at 50° C. for 18 hours. The reaction was stopped by the addition of a saturated aqueous solution of ammonium chloride, and the mixture was partitioned with ethyl acetate and water. The organic layer was washed with a saturated aqueous solution of sodium bicarbonate and saturated saline in this order. Combined aqueous layers were subjected to back extraction with ethyl acetate. All organic layers were combined and dried over sodium sulfate. The desiccant was filtered off, and then, the filtrate was concentrated. The residue was subjected to azeotropy with ethanol and then purified by amino silica gel column chromatography (ethyl acetate-methanol) to obtain compound 11a (444 mg) as a foamy compound.

$^1$H NMR (300 MHz, DMSO-$d_6$) δ 11.13 (br s, 1H, exchangeable with D$_2$O), 8.66, 8.42 (each s, each 1H), 8.06 (d, 2H, J=7.2 Hz), 7.67-7.53 (m, 3H), 7.33-7.14 (m, 9H), 6.85 (d, 4H, J=8.7 Hz), 6.37 (dd, 1H, J=5.5, 6.2 Hz), 5.19 (t, 1H, J=5.7 Hz, exchangeable with D$_2$O), 4.70 (t, 1H, J=5.5 Hz, exchangeable with D$_2$O), 3.80 (m, 2H), 3.73 (s, 6H), 3.61 (m, 1H), 3.50 (m, 1H), 3.41 (s, 2H), 3.09 (d, 1H, J=8.9 Hz), 2.89 (d, 1H, J=8.9 Hz), 2.85 (s, 3H).

(11) Synthesis of Compound 12a

Compound 11a (140 mg) was dissolved in pyridine (2 ml). To the solution, t-butyldimethylsilane chloride (88 mg) was added under ice cooling, and the reaction solution was stirred for 15 hours while gradually brought back to room temperature. The reaction was stopped by the addition of methanol, and the solvent was distilled off under reduced pressure. The residue was diluted with ethyl acetate, and the organic layer was washed with a saturated aqueous solution of sodium bicarbonate and saturated saline in this order. Combined aqueous layers were subjected to back extraction with ethyl acetate. All organic layers were combined and dried over sodium sulfate. The desiccant was filtered off, and then, the filtrate was concentrated. The residue was purified by amino silica gel column chromatography (ethyl acetate-methanol) to obtain compound 12a (68 mg) as a foamy compound.

$^1$H NMR (300 MHz, DMSO-$d_6$) δ 11.10 (br s, 1H, exchangeable with D$_2$O), 8.67, 8.43 (each s, each 1H), 8.05 (d, 2H, J=8.5 Hz), 7.67-7.52 (m, 3H), 7.35-7.17 (m, 9H), 6.86 (d, 4H, J=8.9 Hz), 6.43 (dd, 1H, J=4.9, 6.3 Hz), 4.75 (t, 1H, J=4.9 Hz, exchangeable with D$_2$O), 3.96 (m, 2H), 3.73 (s, 6H), 3.61 (m, 1H), 3.50 (m, 1H), 3.42 (s, 2H), 3.13 (d, 1H, J=9.1 Hz), 2.93 (d, 1H, J=9.1 Hz), 2.89 (s, 3H), 0.63 (s, 9H), =0.11, =0.20 (each s, each 3H).

(12) Synthesis of Compound 13a

Compound 12a (160 mg), 2-cyanoethyl N,N,N',N'-tetraisopropylphosphordiamidite (79 μl), and 4,5-dicyano-1H-imidazole (27 mg) were dissolved in acetonitrile (2 ml), and the reaction solution was stirred at room temperature for 6 hours. The reaction was stopped by the addition of a saturated aqueous solution of sodium bicarbonate, and the mixture was partitioned with ethyl acetate and a saturated aqueous solution of sodium bicarbonate. The organic layer was washed with saturated saline and then dried over sodium sulfate. The desiccant was filtered off and then, the filtrate was concentrated. The residue was purified by amino silica gel column chromatography (hexane-ethyl acetate) to obtain compound 13a (102 mg, diastereomeric mixture) as a foamy compound.

$^{31}$P NMR (121 MHz, DMSO-d$_6$) δ 146.91, 146.78 (each s)

Example 5

Synthesis of siRNA Having Partial Structure of Formula (II) Wherein X was Oxygen Atom, R$^1$ was Methyl Group, R$^2$ was Hydrogen Atom, R$^3$ was Hydroxy Group, and B was Uracil siRNA having the partial structure of the formula (II) wherein X was an oxygen atom, R$^1$ was a methyl group, R$^2$ was a hydrogen atom, R$^3$ was a hydroxy group, and B was uracil was synthesized by the phosphoramidite method using each of the compounds 11 and 22 synthesized as the open circular modified nucleic acid monomer compounds of the formula (I) of the present invention in Examples 1 and 2.

(1) Synthesis of Oligonucleotide

The oligonucleotide was synthesized by a general solid-phase phosphoramidite method using an automatic DNA synthesizer (model H-8 synthesizer). Commercially available products were used as each phosphoramidite block serving as a building unit, and a solid-phase carrier except for the compounds 11 and 22 synthesized as amidite blocks in Examples 1 and 2, respectively. For example, after 1 micromole-scale synthesis, an aqueous methylamine solution (0.5 ml) was added to the oligonucleotide supported by the solid-phase carrier, and the mixture was heated at 50 to 60° C. for 1.5 hours. The solid-phase carrier was filtered off and washed with dimethyl sulfoxide (1.0 ml). A hydrogen trifluoride-triethylamine complex (0.5 ml) was added to combined filtrates, and the mixture was heated at 40 to 50° C. for 1.5 hours. The reaction solution was gel-filtrated or salted out to separate a crude oligonucleotide, which was then purified using an ion-exchange column or a reverse-phase column.

(2) Synthesis of siRNA

The siRNA was synthesized by: adding both strands in equimolar amounts into a PBS buffer solution; heating the mixture at 90° C. for 5 minutes; and then slowly cooling the mixture to room temperature. Specifically, siRNA (1) was synthesized to consist of a sense strand (SEQ ID NO: 1) shown below and an antisense strand (SEQ ID NO: 2) containing one partial structure of the formula (II) induced from the compound 11 synthesized in Example 1, wherein X was an oxygen atom, R$^1$ was a methyl group, R$^2$ was a hydrogen atom, R$^3$ was a hydroxy group, and B was uracil.

siRNA (1):

Sense strand (5' → 3' direction):
(SEQ ID NO: 1)
C(M)U(M)U(M)AC(M)GC(M)U(M)GAGU(M)AC(M)U(M)U(M)C(M)

GAtt

Antisense strand (5' → 3' direction):
(SEQ ID NO: 2)
UCGAAGU(K)ACUC(M)AGCGU(M)AAGtt In this context, the capital letters represent RNAs; the lower-case letters represent DNAs; N(M) represents 2'-OMeRNA; and U(K) represents a nucleotide unit, incorporated in an oligomer, of the partial structure induced from the compound 11 synthesized in Example 1.

Similarly, siRNA (2) was synthesized to consist of a sense strand (SEQ ID NO: 1) and an antisense strand (SEQ ID NO: 3) containing one partial structure of the formula (II) induced from the compound 22 synthesized in Example 2, wherein X was an oxygen atom, R$^1$ was a methyl group, R$^2$ was a hydrogen atom, R$^3$ was a hydroxy group, and B was uracil.

siRNA (2):

Sense strand (5' → 3' direction):
(SEQ ID NO: 1)
C(M)U(M)U(M)AC(M)GC(M)U(M)GAGU(M)AC(M)U(M)U(M)C(M)

GAtt

Antisense strand (5' → 3' direction):
(SEQ ID NO: 3)
UCGAAGU(K2)ACUC(M)AGCGU(M)AAGtt In this context, the capital letters represent RNAs; the lower-case letters represent DNAs; N(M) represents 2'-OMeRNA; and U(K2) represents a nucleotide unit. Incorporated in an oligomer, of the partial structure induced from the compound 22 synthesized in Example 2.

Comparative Example

Control siRNA consisting of sense and antisense strands given below was synthesized by the phosphoramidite method in almost the same way as above except that uridine was used in the control siRNA, instead of the compound 11 or 22 synthesized in Example 1 or 2.

Control siRNA

Sense strand (5' → 3' direction):
(SEQ ID NO: 4)
C(M)U(M)U(M)AC(M)GC(M)U(M)GAGU(M)AC(M)U(M)U(M)C(M)

GAtst

Antisense strand (5' → 3' direction):
(SEQ ID NO: 5)
UCGAAGU(M)ACUC(M)AGCGU(M)AAGtst In this context, the capital letters represent RNAs; the lower-case letters represent DNAs; N(M) represents 2'-OMeRNA: and the lower-case letter "s" represents a phosphorothioate bond.

Test Example

Each siRNA was evaluated using a Dual-Luc reporter system as described below.

1) Preparation of Dual-Loc Reporter Vector

A restriction enzyme sequence was added to a sequence containing a 19-base sequence complementary to the antisense strand of siRNA against the GL3 luciferase gene (Elbashir S M et al., Nature, Vol. 411, 24 May 2001, 494-498), and its 5'-flanking 10 bases and 3'-flanking 10 bases. The resulting sequence was incorporated into the XhoI/NotI site of a psiCHECK2 plasmld (Promega KK) either in a forward direction (sequence A) or in a reverse direction (sequence B) to construct vectors for the expression of firefly luciferase and *Renilla* luciferase, OFF#085 and OFF#086, respectively.

Sequence A

Sense strand:
(SEQ ID NO: 6)
5'-TCGAGGTGGACATCACTTACGCTGAGTACTTCGAAATGTCCGTTGCTAGCGC-3'

Antisense strand:
(SEQ ID NO: 7)
5'-GGCCGCGCTAGCAACGGACATTTCGAAGTACTCAGCGTAAGTGATGTCCACC-3'

Sequence B

Sense strand:
(SEQ ID NO: 8)
5'-TCGAGAACGGACATTTCGAAGTACTCAGCGTAAGTGATGTCCACGCTAGCGC-3'

Antisense strand:
(SEQ ID NO: 9)
5'-GGCCGCGCTAGCGTGGACATCACTTACGCTGAGTACTTCGAAATGTCCGTTC-3'

2) Evaluation of each siRNA using Dual-Luc Reporter System

Human colon cancer cell line HCT116 cells (ATCC) were inoculated at a density of $3 \times 10^6$ cells/10 ml/75 cm$^2$ flask. After overnight culture at 37° C. in 5% $CO_2$, the cells were transfected with the vector OFF#085 or OFF#086 obtained in the preceding paragraph 1) using FuGENE 6 (F. Hoffmann-La Roche Ltd.) and further cultured overnight. Each siRNA synthesized in Example 5 and Comparative Example was diluted with PBS into two serial dilutions of 3.3 nM (final) and 0.0043 nM or 12 serial dilutions from 10 nM to 56 fM and used in reverse transfection of $1.6 \times 10^4$ cells/100 µL/well using Lipofectamine RNAiMAX reagent (Invitrogen Corp.). After two-night culture, firefly luciferase activity and *Renilla* luciferase activity were measured using Dual-Glo Luc Assay kit (Promega KK) according to the attached document. When the luciferase activity (*Renilla*/firefly) of cells reverse-transfected with 10 nM BLOCK-iT™ Alexa Fluor® Red Fluorescent Oligo (Invitrogen Corp.) was defined as 100%, the luciferase activity of the cells transfected with each siRNA was calculated. The $IC_{50}$ value was calculated using GraphPad Prism 5.

The obtained results are shown in Table 1.

TABLE 1

| Expression-suppressive activity of each siRNA | |
|---|---|
| siRNA | 50% inhibition concentration (pM) |
| siRNA (1) | 7 |
| Control RNA | 24 |

TABLE 1-continued

| Expression-suppressive activity of each siRNA | |
|---|---|
| siRNA | 50% inhibition concentration (pM) |
| siRNA (2) | 9 |
| Control RNA | 12 |

As is evident from the results of Table 1, the siRNA (1) containing one partial structure induced from the compound 11 obtained in Example 1 as the open circular modified nucleic acid monomer compound of the formula (I) of the present invention and the siRNA (2) containing one partial structure induced from the compound 22 obtained in Example 2 exerted higher suppressive activity against luciferase expression than that of the control RNA free from these compounds.

INDUSTRIAL APPLICABILITY

When an oligonucleic acid analog containing the open circular modified nucleic acid monomer compound of the present invention as at least one partial structure is used as, for example, siRNA, the resulting siRNA is excellent in biological stability and suppressive activity against the expression of a target gene. In addition, such an oligonucleic acid analog can also be used as antisense RNA, antisense DNA, a decoy nucleic acid, a nucleic acid aptamer, a ribozyme, or the like. The oligonucleic acid analog may be further used as a genetic analysis tool such as an RNA probe, a DNA probe, or a molecular beacon.

Free Text for Sequence Listing

SEQ ID NO: 1; sense strand RNAs of siRNA (1) and siRNA (2) constructed in Example 5:

SEQ ID NO: 2: antisense strand RNA of the siRNA (1) constructed in Example 5, wherein the antisense strand RNA has one partial structure induced from compound 11 synthesized in Example 1;

SEQ ID NO: 3: antisense strand RNA of the siRNA (2) constructed in Example 5, wherein the antisense strand RNA has one partial structure induced from compound 22 synthesized in Example 1;

SEQ ID NO: 4: sense strand RNA of control siRNA constructed in Comparative Example;

SEQ ID NO: 5: antisense strand RNA of the control siRNA constructed in Comparative Example;

SEQ ID NO: 6: sense strand DNA incorporated in Dual-Luc reporter vector OFF#085;

SEQ ID NO: 7: antisense strand DNA incorporated in the Dual-Luc reporter vector OFF#085;

SEQ ID NO: 8: sense strand DNA incorporated in Dual-Luc reporter vector OFF#086; and SEQ ID NO: 9: antisense strand DNA incorporated in the Dual-Luc reporter vector OFF#086.

The invention claimed is:

1. A compound represented by the following formula (I):

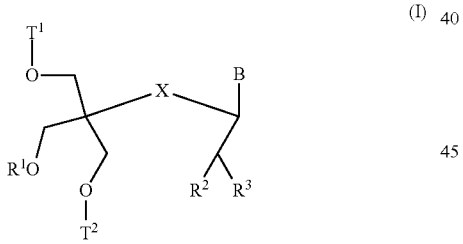

wherein

B represents a group selected from adenine-derived groups which are adenine, 2-fluoroadenine, 2-methyladenine, 2-propyladenine, 2-aminoadenine, 2-aminomethyladenine, 2-aminopropyladenine, 2-methylthio-$N^6$-isopentenyladenine, $N^6$-propyladenine, $N^6$-methyladenine, 7-deazaadenine, 8-aza-7-deazaadenine, 8-vinyladenine, 8-methyladenine, 8-ethynyladenine, 8-phenyladenine, 8-aminoadenine, 8-fluoroadenine, 8-hydroxyladenine, 8-methoxyadenine, 8-methylthioadenine, 8-mercaptoadenine, $N^6$-isopentyladenine, or $N^6,N^6$-dimethyladenine; guanine-derived groups which are guanine, 2-methylguanine, 2-propylguanine, $O^6$-methylguanine, $O^5$-ethylguanine, 7-methylguanine, 7-ethylguanine, 7-deazaguanine, 8-methylguanine, 8-vinylguanine, 8-ethynylguanine, 8-phenylguanine, 8-aminoguanine, 8-fluoroguanine, 8-hydroxyguanine, 8-methoxyguanine, 8-methylthioguanine, 8-mercaptoguanine, and $N^2$-methylguanine; cytosine-derived groups which are cytosine, 2-thiocytosine, 3-deaza-5-azacytosine, 3-methylcytosine, 3-ethylcytosine, 5-methylcytosine, 5-vinylcytosine, 5-ethynylcytosine, 5-fluorocytosine, 5-methylcytosine, 5-propenylcytosine, 5-ethynylcytosine, 5-trifluoromethylcytosine, 6-azacytosine, or $N^4$-acetylcytosine; uracil-derived groups which are uracil, 3-(3-aminocarboxypropyl)uracil, 2-thiouracil, 5-methyl-2-thiouracil, 5-methylaminomethyl-2-thiouracil, 4-thiouracil, 5-methyl-4-thiouracil, 5-methylaminomethyl-4-thiouracil, 5-methyl-2,4-dithiouracil, 5-methylaminomethyl-2,4-dithiouracil, 5-(2-aminopropyl)uracil, 5-guanidinoalkyluracil, 5-(1,3-diazo-1-yl-alkyl)uracil, 5-cyanomethyluracil, 5-dimethylaminoethyluracil, 5-dimethylaminoethyluracil, 5-fluorouracil, 5-methoxyuracil, uracil-5-oxyacetic acid, 5-methoxycarbonylmethyl-2-thiouracil, thiouracil, 5-methoxycarbonylmethyluracil, 5-propynyluracil, 5-propynyluracil, 5-ethynyluracil, 5-trifluoromethyluracil, 6-azauracil, 5,6-dihydrouracil, $N^3$-methyluracil, uracil-5-yl (pseudouracil), 2-thiopseudouracil, 4-thiopseudouracil, 2,4-dithiopseudouracil, 1-methylpseudouracil, 1-methylpseudouracil, 1-methyl-2-thiopseudouracil, 1-methyl-4-thiopseudouracil, 1-methyl-2,4-dithiopseudouracil, 1-ethyl-2-thiopseudouracil, 1-ethyl-4-thiopseudouracil, 1-methyl-2,4-dithiopseudouracil, 1-aminocarbonylethylenyl-2-thiopseudouracil, 1-aminocarbonylethylenyl-4-thiopseudouracil, or 1-aminocarbonylethylenyl-2,4-dithiopseudouracil; phenoxazine-derived groups which are 1,3-diaza-2-oxophenoxazin- 1-yl, 1-aza-2-thio-3-azaphenoxazin-1-yl, 7-aminomethylhydroxy-1,3-diaza-2-thio-phenoxazin-1-yl, 7-aminomethylhydroxy-1,3-diaza-2-oxophenoxazin-1-yl, 7-guanidiummethylhydroxy-1,3-diaza-2-oxophenoxazin-1-yl, or 7-guanidiummethylhydroxy-1,3-diaza-2-thiophenoxazin-1-yl; phenothiazine-derived groups which are 1,3-diaza-2-oxophenothiazin-1 yl, 1-aza-2-thio-3-azaphenothiazin-1-yl or 7-aminoalkyl-hydroxy-1,3-diaza-2-thiophenothiazine; naphthalene-derived groups which are 1,3,5-triaza-2,6-dioxanaphthalene; xanthine-derived groups which are xanthine or hypoxanthine; imidazolyl-derived groups which are nitroimidazolyl or nitrobenzimidazolyl; indazolyl-derived groups which is nitropyrazolylnitroimidazolyl; indolyl-derived groups which are aminoindolyl, 7-azaindolyl, 6-methyl-7-azaindolyl, or 4,6-dimethyl-indolyl; pyrimidinyl-derived groups which are pyrrolopyrimidinyl or 9-methyl-imidazopyrimidinyl; pyridinyl-derived groups which is pyrrolopyridinyl: carbostyril-derived groups which are 3-methylisocarbostyril, 5-methylisocarbostyril, 3-methyl-7-propynylisocarbostyril, isocarbostyril, 7-propynylisocarbostyril, 3-methylisocarbostyril, 5-methylisocarbostyril, or 3-methyl-7-propynylisocarbostyril; pyridinyl-derived groups which are imidazopyridinyl or pyrrolopyridinyl; imidazolyl-derived groups which are 4-fluoro-6-methylbenzimidazolyl or 4-methylbenzimidazolyl; thymine-derived groups which is 6-azothymine; pyridinone-derived groups which is 2-pyridinone; indole-derived groups which is 5-nitroindole; pyrrole-derived groups which is 3-nitropyrrole; pyrimidine-derived groups which are 6-azapyrimidine, pyrrolopyrimidin-2-on-3-yl, 6-phenyl-pyrrolopyrimidin-2-on-3-yl, p-fluoro-6-phenyl-pyrrolopyrimidin-2-on-3-yl, o-fluoro-6-phenyl-pyrrolopyrimidin-2-on-3-yl, bis-o-fluoro-6-phenyl-pyrrolopyrimidin-2-on-3-yl, p-aminoalkylhydroxy-6-phenyl-pyrrolopyrimidin-2-on-3-yl, o-aminoalkylhydroxy-6-phenyl-pyrrolopyrimidin-2-on-3-yl, bis-o-di-aminoalkylhydroxy-6-phenyl-pyrrolopyrimidin-2-on-3-yl, pyridopyrimidin-3-yl, 2-oxo-7-aminopyridopyrimidin-3-yl, or 2-oxo-pyridopyrimidin-3-yl; or purine-derived groups which are 2-aminopurine or 2,6-diaminopurine;

$T^1$ represents a protective group for a hydroxy group, or a hydrogen atom;

$T^2$ represents a phosphorus-containing functional group, a protective group for a hydroxy group, or a hydrogen atom;

X represents an oxygen atom, a sulfur atom, —C($E^1$)($E^2$)-, —C(=O)—, —C(=S)—, —C(=C($E^1$)($E^2$))-, —N($E^3$)-, or —C(=N$E^3$)—;

$E^1$ and $E^2$ each independently represent a hydrogen atom, a halogen atom, an optionally substituted hydroxy group, an optionally substituted $C_{1-6}$ alkyl group, an optionally substituted $C_{2-6}$ alkenyl group, or an optionally substituted amino group;

$E^3$ represents a hydrogen atom, an optionally substituted $C_{1-6}$ alkyl group, or an optionally substituted $C_{2-6}$ alkenyl group;

$R^1$ represents an optionally substituted $C_{1-6}$ alkyl group, an optionally substituted $C_{2-6}$ alkenyl group, or an optionally substituted amino group;

$R^2$ represents an optionally substituted hydroxy group, an optionally substituted amino group, a hydrogen atom, an optionally substituted $C_{1-6}$ alkyl group, an optionally substituted $C_{2-6}$ alkenyl group, an optionally substituted $C_{2-6}$ alkynyl group, or a halogen atom; and $R^3$ represents a hydrogen atom, an optionally substituted hydroxy group, an optionally substituted amino group, an optionally substituted $C_{1-6}$ alkyl group, an optionally substituted $C_{2-6}$ alkenyl group, an optionally substituted $C_{2-6}$ alkynyl group, or a halogen atom, or a salt thereof.

2. An oligonucleic acid analog comprising one or more partial structures each represented by the following formula (II):

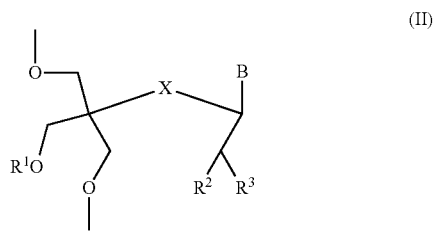

wherein

B represents a group selected from adenine-derived groups which are adenine, 2-fluoroadenine, 2-methyladenine, 2-propyladenine, 2-aminoadenine, 2-aminomethyladenine, 2-aminopropyladenine, 2-methylthio-$N^6$-isopentenyladenine, $N^6$-propyladenine, $N^6$-methyladenine, 7-deazaadenine, 8-aza-7-deazaadenine, 8-vinyladenine, 8-methyladenine, 8-ethynyladenine, 8-phenyladenine, 8-aminoadenine, 8-fluoroadenine, 8-hydroxyladenine, 8-methoxyadenine, 8-methylthioadenine, 8-mercaptoadenine, $N^6$-isopentyladenine, or $N^6,N^6$-dimethyladenine; guanine-derived groups which are guanine, 2-methylguanine, 2-propylguanine, $O^6$-methylguanine, $O^6$-ethylguanine, 7-methylguanine, 7-ethylguanine, 7-deazaguanine, 8-methylguanine, 8-vinylguanine, 8-ethynylguanine, 8-phenylguanine, 8-aminoguanine, 8-fluoroguanine, 8-hydroxylguanine, 8-methoxyguanine, 8-methylthioguanine, 8-mercaptoguanine, and $N^2$-methylguanine; cytosine-derived group which are cytosine, 2-thiocytosine, 3-deaze-5-azacytosine, 3-methylcytosine, 3-ethylcytosine, 5-methylcytosine, 5-vinylcytosine, 5-ethynylcytosine, 5-fluorocytosine, 5-methylcytosine, 5-propenylcytosine, 5-ethynylcytosine, 5-trifluoromethylcytosine, 6-azacytosine, or $N^4$-acetylcytosine; uracil-derived groups which are uracil, 3-(3-amino-carboxypropyl)uracil, 2-thiouracil, 5-methyl-2-thiouracil, 5-methylaminomethyl-2-thiouracil, 4-thiouracil, 5-methyl-4-thiouracil, 5-methylaminomethyl-4-thiouracil, 5-methyl-2,4-dithiouracil, 5-methylaminomethyl-2,4-dithiouracil, 5-(2-aminopropyl)uracil, 5-guanidinoalkyluracil, 5-(1,3-diazo-1-yl-alkyl)uracil, 5-cyanomethyluracil, 5-dimethylaminoethyluracil, 5-dimethylaminoethyluracil, 5-fluorouracil, 5-methoxyuracil, uracil-5-oxyacetic acid, 5-methoxycarbonylmethyl-2-thiouracil, 5-methoxycarbonylmethyluracil, 5-propynyluracil, 5-propynyluracil, 5-ethynyluracil, 5-trifluoromethyluracil, 6-azauracil, 5,6-dihydrouracil, $N^3$-methyluracil, uracil-5-yl (pseudouracil), 2-thiopseudouracil, 4-thiopseudouracil, 2,4-dithiopseudouracil, 1-methylpseudouracil, 1-methylpseudouracil, 1-methyl-2-thiopseudouracil, 1-methyl-4-thiopseudouracil, 1-methyl-2,4-dithiopseudouracil, 1-ethyl-2-thiopseudouracil, 1-ethyl-4-thiopseudouracil, 1-ethyl-2,4-dithiopseudouracil, 1-aminocarbonylethylenyl-2-thiopseudouracil, 1-aminocarbonylethylenyl-4-thiopseudouracil, or 1-aminocarbonylethylenyl-2,4-dithiopseudouracil; phenoxazine-derived groups which are 1,3-diaza-2-oxophenoxazin-1-yl, 1-aza-2-thio-3-azaphenoxazin-1-yl, 7-aminomethylhydroxy-1,3-diaza-2-thio-phenoxazin-1-yl, 7-aminomethylhydroxy-1,3-diaza-2-oxophenoxazin-1-yl, 7-guanidiummethylhydroxy-1,3-diaza-2-oxophenoxazin-1-yl, or 7-guanidiummethylhydroxy-1,3-diaza-2-thiophenoxazin-1-yl; phenothiazine-derived groups which are 1,3-diaza-2-oxophenothiazin-1-yl, 1-aza-2-thio-3-azaphenothiazin-1-yl or 7-aminoalkylhydroxy-1,3-diaza-2-thiophenothiazine; naphthalene-derived groups which is 1,3,5-triaza-2,6-dioxanaphthalene; xanthine-derived groups which are xanthine or hypoxanthine; imidazolyl-derived groups which are nitroimidazolyl or nitrobenzimidazolyl; imidazolyl-derived groups which is nitropyrazolylnitroindazolyl; indolyl-derived groups which are aminoindolyl, 7-azaindolyl, 6-methyl-7-azaindolyl, or 4,6-dimethylindolyl; pyrimidinyl-derived groups which are pyrrolopyrimidinyl or 9-methylimidazopyrimidinyl; pyridinyl-derived groups which is pyrrolopyridinyl; carbostyril-derived groups which are 3-methylisocarbostyril, 5-methylisocarbostyril, 3-methy-7-propynylisocarbostyril, isocarbostyril, 7-propynylisocarbostyril, 3-methylisocarbostyril, 5-methylisocarbostyril, or 3-methyl-7-propynylisocarbostyril; pyridinyl-derived groups which are imidazopyridinyl or pyrrolopyridinyl; imidazolyl-derived groups which are 4-fluoro-6-methylbenzimidazolyl or 4-methylbenzimidazolyl; thymine-derived groups which is 6-azothymine; pyridinone-derived groups which is 2-pyridinone; indole-derived groups which is 5-nitroindole; pyrrole-derived groups which is 3-nitropyrrole; pyrimidine-derived groups which are 6-azapyrimidine, pyrrolopyrimidin-2-on-3-yl, 6-phenyl-pyrrolopyrimidin-2-on-3-yl, p-fluoro-6-phenyl-pyrrolopyrimidin-2-on-3-yl, o-fluoro-6-phenyl-pyrrolopyrimidin-2-on-3-yl, bis-o-fluoro-6-phenyl-pyrrolopyrimidin-2-on-3-yl, p-aminoalkylhydroxy-6-phenyl-pyrrolopyrimidin-2-on-3-yl, o-aminoalkylhydroxy-6-phenyl-pyrrolopyrimidin-2-on-3-yl, bis-o-di-aminoalkylhydroxy-6-phenyl-pyrrolopyrimidin-2-on-3-yl, pyridopyrimidin-3-yl, 2-oxo-7-aminopyridopyrimidin-3-yl, or 2-oxo-pyridopyrimidin-3-yl; or purin-derived groups which are 2-aminopurine or 2,6-diaminopurine;

X represents an oxygen atom, a sulfur atom, —C(E$^1$)(E$^2$)-, —C(=O)—, —C(=S)—, —C(=C(E$^1$)(E$^2$))-, —N(E$^3$)-, or —C(=NE$^3$)-;

E$^1$ and E$^2$ each independently represent a hydrogen atom, a halogen atom, an optionally substituted hydroxy group, an optionally substituted $C_{1-4}$ alkyl group, an optionally substituted $C_{2-6}$ alkenyl group, or an optionally substituted amino group;

E$^3$ represents a hydrogen atom, an optionally substituted $C_{1-6}$ alkyl group, or an optionally substituted $C_{2-6}$ alkenyl group;

R$^1$ represents an optionally substituted $C_{1-6}$ alkyl group, an optionally substituted $C_{2-6}$ alkenyl group, or an optionally substituted amino group;

R$^2$ represents an optionally substituted hydroxy group, an optionally substituted amino group, a hydrogen atom, an optionally substituted $C_{1-6}$ alkyl group, an optionally substituted $C_{2-6}$ alkenyl group, an optionally substituted $C_{2-6}$ alkynyl group, or a halogen atom; and R$^3$ represents a hydrogen atom, an optionally substituted hydroxy group, an optionally substituted amino group, an optionally substituted $C_{1-6}$ alkyl group, an optionally substituted $C_{2-6}$ alkenyl group, an optionally substituted $C_{2-6}$ alkynyl group, or a halogen atom, or a salt thereof, provided that when the oligonucleic acid analog or the salt thereof comprises two or more of the partial structures, B, R$^1$, R$^2$, and R$^3$ may each be the same or different between or among the partial structures.

3. A compound represented by the following formula (III):

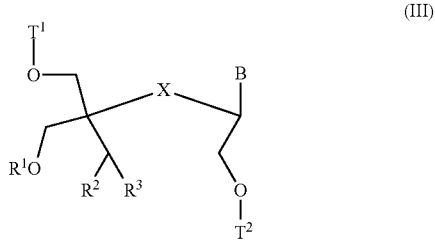

(III)

wherein

B represents a group selected from adenine-derived groups which are adenine, 2-fluoroadenine, 2-methyladenine, 2-propyladenine, 2-aminoadenine, 2-aminomethyladenine, 2-aminopropyladenine, 2-methylthio-N$^6$-isopentenyladenine, N$^6$-propyladenine, N$^6$-methyladenine, 7-deazaadenine, 8-aza-7-deazaadenine, 8-vinyladenine, 8-methyladenine, 8-ethynyladenine, 8-phenyladenine, 8-aminoadenine, 8-fluoroadenine, 8-hydroxyladenine, 8-methoxyadenine, 8-methylthioadenine, 8-mercaptoadenine, N$^6$-isopentyladenine, or N$^6$,N$^6$-dimethyladenine; guanine-derived groups which are guanine, 2-methylguanine, 2-propylguanine, O$^6$-methylguanine, O$^6$-ethylguanine, 7-methylguanine, 7-ethylguanine, 7-deazaguanine, 8-methylguanine, 8-vinylguanine, 8-ethynylguanine, 8-phenylguanine, 8-aminoguanine, 8-fluoroguanine, 8-hydroxylguanine, 8-methoxyguanine, 8-methylthioguanine, 8-mercaptoguanine, and N$^2$-methylguanine; cytosine-derived groups which are cytosine, 2-thiocytosine, 3-deaza-5-azacytosine, 3-methylcytosine, 3-ethylcytosine, 5-methylcytosine, 5-vinylcytosine, 5-ethynylcytosine, 5-fluorocytosine, 5-methylcytosine, 5-propenylcytosine, 5-ethynylcytosine, 5-trifluoromethylcytosine, 6-azacytosine, or N$^4$-acetylcytosine; uracil-derived groups which are uracil, 3-(3-amino-carboxypropyl)uracil, 2-thiouracil, 5-methyl-2-thiouracil, 5-methylaminomethyl-2-thiouracil, 4-thiouracil, 5-methyl-4-thiouracil, 5-methylaminomethyl-4-thiouracil, 5-methyl-2,4-dithiouracil, 5-methylaminomethyl-2,4-dithiouracil, 5-(2-aminopropyl)uracil, 5-guanidinoalkyluracil, 5-(1,3-diazo-1-yl-alkyl)uracil, 5-cyanomethyluracil, 5-dimethylaminoethyluracil, 5-dimethylaminoethyluracil, 5-fluorouracil, 5-methoxyuracil, uracil-5-oxyacetic acid, 5-methoxycarbonylmethyl-2-thiouracil, 5-methoxycarbonylmethyluracil, 5-propynyluracil, 5-propynyluracil, 5-ethynyluracil, 5-trifluoromethyluracil, 6-azauracil, 5,6-dihydrouracil, $N^3$-methyluracil, uracil-5-yl (pseudouracil), 2-thiopseudouracil, 4-thiopseudouracil, 2,4-dithiopseudouracil, 1-methylpseudouracil, 1-methylpseudouracil, 1-methyl-2-thiopseudouracil, 1-methyl-4-thiopseudouracil, 1-methyl-2,4-dithiopseudouracil, 1-ethyl-2-thiopseudouracil, 1-ethyl-4-thiopseudouracil, 1-ethyl-2,4-dithiopseudouracil, 1-aminocarbonylethylenyl-2-thiopseudouracil, 1-aminocarbonylethylenyl-4-thiopseudouracil, or 1-aminocarbonylethylenyl-2,4-dithiopseudouracil; phenoxazine-derived groups which are 1,3-diaza-2-oxophenoxazin-1-yl, 1-aza-2-thio-3-azaphenoxazin-1-yl, 7-aminomethylhydroxy-1,3-diaza-2-thio-phenoxazin-1-yl, 7-aminomethylhydroxy-1,3-diaza-2-oxophenoxazin-1-yl, 7-guanidiummethylhydroxy-1,3-diaza-2-oxophenoxazin-1-yl, or 7-guanidiummethylhydroxy-1,3-diaza-2-thiophenoxazin-1-yl; phenothiazine-derived groups which are 1,3-diaza-2-oxophenothiazin-1-yl, 1-aza-2-thio-3-azaphenothiazin-1-yl or 7-aminoalkylhydroxy-1,3-diaza-2-thiophenothiazine; naphthalene-derived groups which is 1,3,5-triaza-2,6-dioxanaphthalene; xanthine-derived groups which are xanthine or hypoxanthine; imidazolyl-derived groups which are nitroimidazolyl or nitrobenzimidazolyl; indazolyl-derived groups which is nitropyrazolylnitroindazolyl; indolyl-derived groups which is aminoindolyl, 7-azaindolyl, 6-methyl-7-azaindolyl, or 4,6-dimethylindolyl; pyrimidinyl-derived groups which are pyrrolopyrimidinyl or 9-methyl-imidazopyrimidinyl; pyridinyl-derived groups which is pyrrolopyridinyl; carbostyril-derived groups which are 3-methylisocarbostyril, 5-methylisocarbostyril, 3-methyl-7-propynylisocarbostyril, isocarbostyril, 7-propynylisocarbostyril, 3-methylisocarbostyril, 5-methylisocarbostyril, or 3-methyl-7-propynylisocarbostyril; pyridinyl-derived groups which are imidazopyridinyl or pyrrolopyridinyl; imidazolyl-derived groups which are 4-fluoro-6-methylbenzimidazolyl or 4-methylbenzimidazolyl; thymine-derived groups which is 6-azothymine; pyridinone-derived groups which is 2-pyridinone; indole-derived groups which is 5-nitroindole; pyrrol-derived groups which is 3-nitropyrrole; pyrimidine-derived groups which are 6-azapyrimidine, pyrrolopyrimidin-2-on-3-yl, 6-phenyl-pyrrolopyrimidin-2-on-3-yl, p-fluoro-6-phenyl-pyrrolopyrimidin-2-on-3-yl, o-fluoro-6-phenyl-pyrrolopyrimidin-2-on-3-yl, bis-o-fluoro-6-phenyl-pyrrolopyrimidin-2-on-3-yl, p-aminoalkylhydroxy-6-phenyl-pyrrolopyrimidin-2-on-3-yl, o-aminoalkylhydroxy-6-phenyl-pyrrolopyrimidin-2-on-3-yl, bis-o-di-aminoalkylhydroxy-6-phenyl-pyrrolopyrimidin-2-on-3-yl, pyridopyrimidin-3-yl, 2-oxo-7-aminopyridopyrimidin-3-yl, or 2-oxo-pyridopyrimidin-3-yl; or purine-derived groups which are 2-aminopurine or 2,6-diaminopurine;

$T^1$ represents a protective group for a hydroxy group, or a hydrogen atom;

$T^2$ represents a phosphorus-containing functional group, a protective group for a hydroxy group, or a hydrogen atom;

X represents an oxygen atom, a sulfur atom, —C($E^1$)($E^2$)-, —C(=O)—, —C(=S)—, —C(=C($E^1$)($E^2$))-, —N($E^3$)-, or —C(=N$E^3$)-;

$E^1$ and $E^2$ each independently represent a hydrogen atom, a halogen atom, an optionally substituted hydroxy group, an optionally substituted $C_{1-6}$ alkyl group, an optionally substituted $C_{2-6}$ alkenyl group, or an optionally substituted amino group;

$E^3$ represents a hydrogen atom, an optionally substituted $C_{1-6}$ alkyl group, or an optionally substituted $C_{2-6}$ alkenyl group;

$R^1$ represents an optionally substituted $C_{1-6}$ alkyl group, an optionally substituted $C_{2-6}$ alkenyl group, or an optionally substituted amino group;

$R^2$ represents an optionally substituted hydroxy group, an optionally substituted amino group, a hydrogen atom, an optionally substituted $C_{1-6}$ alkyl group, an optionally substituted $C_{2-6}$ alkenyl group, an optionally substituted $C_{2-6}$ alkynyl group, or a halogen atom; and $R^3$ represents a hydrogen atom, an optionally substituted hydroxy group, an optionally substituted amino group, an optionally substituted $C_{1-6}$ alkyl group, an optionally substituted $C_{2-6}$ alkenyl group, an optionally substituted $C_{2-6}$ alkynyl group, or a halogen atom, or a salt thereof.

4. An oligonucleic acid analog comprising one or more partial structures each represented by the following formula (IV):

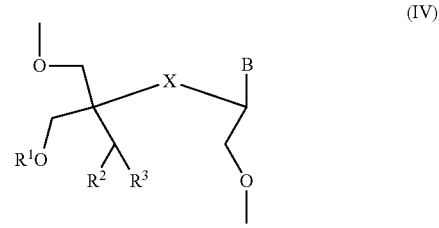

wherein

B represents a group selected from adenine-derived groups, which are adenine, 2-fluoroadenine, 2-methyladenine, 2-propyladenine, 2-aminoadenine, 2-aminomethyladenine, 2-aminopropyladenine, 2-methylthio-$N^6$-isopentenyladenine, $N^6$-propyladenine, $N^6$-methyladenine, 7-deazaadenine, 8-aza-7-deazaadenine, 8-vinyladenine, 8-methyladenine, 8-ethynyladenine, 8-phenyladenine, 8-aminoadenine, 8-fluoroadenine, 8-hydroxyladenine, 8-methoxyadenine, 8-methylthioadenine, 8-mercaptoadenine, $N^5$-isopentyladenine, or $N^6,N^6$-dimethyladenine; guanine-derived groups which are guanine, 2-methylguanine, 2-propylguanine, $O^6$-methylguanine, $O^6$-ethylguanine, 7-methylguanine, 7-ethylguanine, 7-deazaguanine, 8-methylguanine, 8-vinylguanine, 8-ethynylguanine, 8-phenylguanine, 8-aminoguanine, 8-fluoroguanine, 8-hydroxylguanine, 8-methoxyguanine, 8-methylthioguanine, 8-mercaptoguanine, and $N^2$-methylguanine; cytosine-derived groups which are cytosine, 2-thiocytosine, 3-deaza-5-azacytosine, 3-methylcytosine, 3-ethylcytosine, 5-methylcytosine, 5-vinylcytosine, 5-ethynylcytosine, 5-fluorocytosine, 5-methylcytosine, 5-propenylcytosine, 5-ethynylcytosine, 5-trifluoromethylcytosine, 6-azacytosine, or $N^4$-acetylcytosine; uracil-derive groups which are uracil, 3-(3-amino-carboxypropyl)uracil, 2-thiouracil, 5-methyl-2-thiouracil, 5-methylaminomethyl-2-thiouracil, 4-thiouracil, 5-methyl-4-thiouracil, 5-methylaminomethyl-4-thiouracil, 5-methyl-2,4-dithiouracil, 5-methylaminomethyl-2,4-dithiouracil, 5-(2-aminopropyl)uracil, 5-guanidinoalkyluracil, 5-(1,3-diazo-1-yl-alkyl)uracil, 5-cyanomethyluracil, 5-dimethylaminoethyluracil, 5-dimethylaminoethyluracil, 5-fluorouracil, 5-methoxyuracil, uracil-5-oxyacetic acid, 5-methoxycarbonylmethyl-2-thiouracil, 5-methoxycarbonylmethyluracil, 5-propynyluracil, 5-propynyluracil, 5-ethynyluracil, 5-trifluoromethyluracil, 6-azauracil, 5,6-dihydrouracil, $N^3$-methyluracil, uracil-5-yl (pseudouracil), 2-thiopseudouracil, 4-thiopseudouracil, 2,4-dithiopseudouracil, 1-methylpseudouracil, 1-methylpseudouracil, 1-methyl-2-thiopseudouracil, 1-methyl-4-thiopseudouracil, 1-methyl-2,4-dithiopseudouracil, 1-ethyl-2-thiopseudouracil, 1-ethyl-4-thiopseudouracil, 1-ethyl-2,4-dithiopseudouracil, 1-aminocarbonylethylenyl-2-thiopseudouracil, 1-aminocarbonylethylenyl-4-thiopseudouracil, or 1-aminocarbonylethylenyl-2,4-dithiopseudouracil; phenoxazine-derive groups which are 1,3-diaza-2-oxophenoxazin-1-yl, 1-aza-2-thio-3-azaphenoxazin-1-yl, 7-aminomethylhydroxy-1,3-diaza-2-thio-phenoxazin-1-yl, 7-aminomethylhydroxy-1,3-diaza-2-oxophenoxazin-1-yl, 7-guanidiummethylhydroxy-1,3-diaza-2-oxophenoxazin-1-yl, or 7-guanidiummethylhydroxy-1,3-diaza-2-thiophenoxazin-1-yl; phenothiazine-derived groups which are 1,3-diaza-2-oxophenothiazin-1-yl, 1-aza-2-thio-3-azaphenothiazin-1-yl or 7-aminoalkylhydroxy-1,3-diaza-2-thiophenothiazine; naphthalene-derived groups which is 1,3,5-triaza-2,6-dioxanaphthalene; xanthine-derived groups which are xanthine or hypoxanthine; imidazolyl-derived groups which are nitroimidazolyl or nitrobenzimidazolyl; indazolyl-derived groups which is nitropyrazolylnitroindazolyl; indolyl-derived groups which are aminoindolyl, 7-azaindolyl, 6-methyl-7-azaindolyl, or 4,6-dimethylindolyl; pyrimidinyl-derived groups which are pyrrolopyrimidinyl or 9-methylimidazopyrimidinyl; pyridinyl-derived groups which is pyrrolopyridinyl; carbostyril-derived groups which are 3-methylisocarbostyril, 5-methylisocarbostyril, 3-methyl-7-propynylisocarbostyril, isocarbostyril, 7-propynylisocarbostyril, 3-methylisocarbostyril, 5-methylisocarbostyril, or 3-methyl-7-propynylisocarbostyril; pyridinyl-derived groups which are imidazopyridinyl or pyrrolopyridinyl; imidazolyl-derived groups which are 4-fluoro-6-methylbenzimidazolyl or 4-methylbenzimidazolyl; thymine-derived groups which is 6-azothymine; pyridinone-derived groups which is 2-pyridinone; indole-derived groups which is 5-nitroindole; pyrrole-derived groups which is 3-nitropyrrole; pyrimidine-derived groups which are 6-azapyrimidine, pyrrolopyrimidin-2-on-3-yl, 6-phenyl-pyrrolopyrimidin-2-on-3-yl, p-fluoro-6-phenyl-pyrrolopyrimidin-2-on-3-yl, o-fluoro-6-phenyl-pyrrolopyrimidin-2-on-3-yl, bis-o-fluoro-6-phenyl-pyrrolopyrimidin-2-on-3-yl, p-aminoalkylhydroxy-6-phenyl-pyrrolopyrimidin-2-on-3-yl, o-aminoalkylhydroxy-6-phenyl-pyrrolopyrimidin-2-on-3-yl, bis-o-di-aminoalkylhydroxy-6-phenyl-pyrrolopyrimidin-2-on-3-yl, pyridopyrimidin-3-yl, 2-oxo-7-aminopyridopyrimidin-3-yl, or 2-oxo-pyridopyrimidin-3-yl; or purine-derived groups which are 2-aminopurine or 2,6-diaminopurine;

X represents an oxygen atom, a sulfur atom, —C($E^1$)($E^2$)-, —C(=O)—, —C(=S)—, —C(=C($E^1$)($E^2$))-, —N($E^3$)-, or —C(=N$E^3$)-;

$E^1$ and $E^2$ each independently represent a hydrogen atom, a halogen atom, an optionally substituted hydroxy group, an optionally substituted $C_{1-6}$ alkyl group, an optionally substituted $C_{2-6}$ alkenyl group, or an optionally substituted amino group;

$E^3$ represents a hydrogen atom, an optionally substituted $C_{1-6}$ alkyl group, or an optionally substituted $C_{2-6}$ alkenyl group;

$R^1$ represents an optionally substituted $C_{1-6}$ alkyl group, an optionally substituted $C_{2-6}$ alkenyl group, or an optionally substituted amino group;

$R^2$ represents an optionally substituted hydroxy group, an optionally substituted amino group, a hydrogen atom, an optionally substituted $C_{1-6}$ alkyl group, an optionally substituted $C_{2-6}$ alkenyl group, an optionally substituted $C_{2-6}$ alkynyl group, or a halogen atom; and $R^3$ represents a hydrogen atom, an optionally substituted hydroxy group, an optionally substituted amino group, an optionally substituted $C_{1-6}$ alkyl group, an optionally substituted $C_{2-6}$ alkenyl group, an optionally substituted $C_{2-6}$ alkynyl group, or a halogen atom, or a salt thereof, provided that when the oligonucleic acid analog or the salt thereof comprises two or more of the partial structures, B, $R^1$, $R^2$, and $R^3$ may each be the same or different between or among the partial structures.

5. The compound according to claim 1 or 3, wherein B is an adenine-derived group or a guanine-derived group, or a salt thereof.

6. The compound according to claim 1 or 3, wherein $R^1$ is a $C_{1-6}$ alkyl group, or a salt thereof.

7. The oligonucleic acid analog according to claim 2 or 4, wherein B is an adenine-derived group or a guanine-derived group, or a salt thereof.

8. The oligonucleic acid analog according to claim 2 or 4, wherein $R^1$ is a $C_{1-6}$ alkyl group, or a salt thereof.

* * * * *

UNITED STATES PATENT AND TRADEMARK OFFICE
CERTIFICATE OF CORRECTION

PATENT NO. : 9,725,474 B2  Page 1 of 1
APPLICATION NO. : 14/439460
DATED : August 8, 2017
INVENTOR(S) : Shumpei Murata et al.

It is certified that error appears in the above-identified patent and that said Letters Patent is hereby corrected as shown below:

In the Claims

Claim 1, Column 79, Line 64, "$O^5$ ethylguanine," should read -- $O^6$ ethylguanine, --.

Claim 2, Column 82, Lines 46-47, "cytosine-derived group" should read -- cytosine-derived groups --.

Claim 4, Column 86, Line 58, "$N^5$-isopentyladenine" should read -- $N^6$-isopentyladenine --.

Signed and Sealed this
Thirty-first Day of October, 2017

Joseph Matal
*Performing the Functions and Duties of the
Under Secretary of Commerce for Intellectual Property and
Director of the United States Patent and Trademark Office*